United States Patent
Gao et al.

(10) Patent No.: US 12,134,615 B2
(45) Date of Patent: Nov. 5, 2024

(54) COMPOUND, ELECTRON TRANSPORT MATERIAL, DISPLAY PANEL AND DISPLAY APPARATUS

(71) Applicants: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Lu Zhai, Shanghai (CN); Lei Zhang, Shanghai (CN); Quan Ran, Shanghai (CN); Wenpeng Dai, Shanghai (CN); Yuyang Guo, Shanghai (CN); Xia Li, Shanghai (CN)

(73) Assignee: WUHAN TIANMA MICRO-ELECTRONICS CO., LTD., Wuhan (CN)

( * ) Notice: Subject to any disclaimer, the term of this patent is extended or adjusted under 35 U.S.C. 154(b) by 807 days.

(21) Appl. No.: 17/147,085

(22) Filed: Jan. 12, 2021

(65) Prior Publication Data
US 2021/0130355 A1     May 6, 2021

(30) Foreign Application Priority Data

Oct. 30, 2020    (CN) .......................... 202011193784.6

(51) Int. Cl.
*C07D 471/14*    (2006.01)
*C07D 519/00*    (2006.01)
(Continued)

(52) U.S. Cl.
CPC ......... *C07D 471/14* (2013.01); *C07D 519/00* (2013.01); *H10K 50/125* (2023.02);
(Continued)

(58) Field of Classification Search
None
See application file for complete search history.

(56) References Cited

U.S. PATENT DOCUMENTS

| 2011/0095282 A1* | 4/2011 | Pflumm | H10K 85/624 |
| | | | 548/310.7 |
| 2016/0155959 A1* | 6/2016 | Kaiser | H10K 85/6572 |
| | | | 252/301.16 |

(Continued)

FOREIGN PATENT DOCUMENTS

| CN | 106986870 A | | 7/2017 | |
| CN | 108424420 A | * | 8/2018 | ............ C07F 7/0812 |

(Continued)

OTHER PUBLICATIONS

Youn, Kyu Man, et al. "Blue thermally activated delayed fluorescence emitters with a δ-pyridoindole donor moiety." New Journal of Chemistry 42.7 (2018): 5532-5539. (Year: 2018).*

(Continued)

*Primary Examiner* — Dawn L Garrett
(74) *Attorney, Agent, or Firm* — CHRISTENSEN O'CONNOR JOHNSON KINDNESS PLLC

(57) ABSTRACT

The present disclosure provides a compound having a structure represented by Formula 1, where $X_1$-$X_4$ are each independently selected from a carbon atom or a nitrogen atom, and at least two of $X_1$-$X_4$ are each a nitrogen atom; $R_1$-$R_4$ are independently absent or selected from hydrogen, C1-C20 alkyl, C1-C20 alkoxy, C1-C20 alkylthio, C1-C20 alkylamino, C6-C30 aryl, or C2-C30 heteroaryl; m is 1 or 2; n and q are each independently selected from 0, 1, or 2, n+q≥1, and m+n+q=3; Ar is C6-C30 aryl. The molecular structure of the compound has a nitrogen-containing multidentate ligand suitable to form complexes with metal Yb or LiQ to form a metal organic complex having multidentate (Continued)

bondings. When applied to an OLED device, it can effectively lower the turn-on voltage and operating voltage, improve the efficiency, and prolong lifetime of the OLED device.

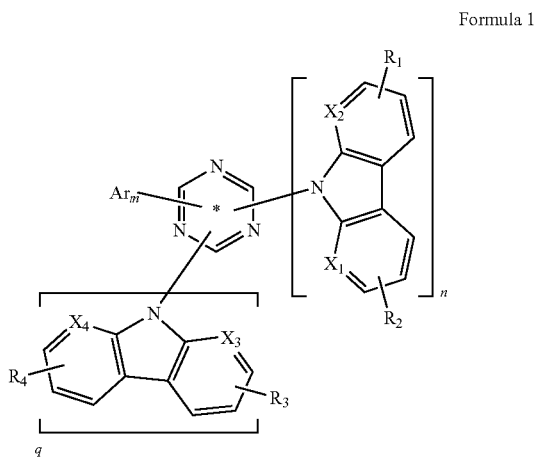

Formula 1

15 Claims, 4 Drawing Sheets

(51) Int. Cl.
*H10K 50/125* (2023.01)
*H10K 50/13* (2023.01)
*H10K 50/165* (2023.01)
*H10K 50/17* (2023.01)
*H10K 50/18* (2023.01)
*H10K 50/19* (2023.01)
*H10K 85/40* (2023.01)
*H10K 85/60* (2023.01)

(52) U.S. Cl.
CPC ........... *H10K 50/131* (2023.02); *H10K 85/40* (2023.02); *H10K 85/615* (2023.02); *H10K 85/654* (2023.02); *H10K 85/6572* (2023.02); *H10K 85/6574* (2023.02); *H10K 85/6576* (2023.02); *H10K 50/165* (2023.02); *H10K 50/171* (2023.02); *H10K 50/18* (2023.02); *H10K 50/19* (2023.02)

(56) References Cited

U.S. PATENT DOCUMENTS

2019/0198790 A1* 6/2019 Kim .................. H10K 59/38
2019/0305227 A1* 10/2019 Yoon .................. H10K 85/626

FOREIGN PATENT DOCUMENTS

| | | |
|---|---|---|
| CN | 111224005 A | 6/2020 |
| KR | 20150124637 A | 11/2015 |
| KR | 20180063708 A | 6/2018 |
| WO | 2020/091521 A1 | 5/2020 |

OTHER PUBLICATIONS

Machine translation for CN 108424420 A (publication date Aug. 2018). (Year: 2018).*
First Office Action mailed May 28, 2021, in corresponding Chinese Patent Application No. 202011193784.6, 126 pages (with English translation).

* cited by examiner

COMPOUND, ELECTRON TRANSPORT MATERIAL, DISPLAY PANEL AND DISPLAY APPARATUS

CROSS-REFERENCE TO RELATED APPLICATIONS

The present application claims priority to Chinese Patent Application No. 202011193784.6, filed on Oct. 30, 2020, the content of which is incorporated herein by reference in its entirety.

TECHNICAL FIELD

The present disclosure relates to the field of organic light-emitting device (OLED device) technology, and particularly, to a compound that can be used as an electron transport material, and an electron transport material, a display panel and a display apparatus including the compound.

BACKGROUND

Alq3 is an electron transport material used in traditional electroluminescent devices, but Alq3 has low electron mobility (about $10^{-6}$ cm$^2$/Vs), causing an imbalance between the electron transport and the hole transport of the devices. With the commercialization and practical application of electroluminescent devices, it is desirable to obtain electronic transport materials having higher transport efficiency and better performance over conventionally used materials. Researchers have done a lot of exploratory work in this field.

Materials used for electron transport layer should avoid absorbing visible light. In order to receive electrons from the cathode, approximately 2.4 to 3.0 eV of lowest unoccupied molecular orbital (LUMO) energy is required (where the result is calculated under mass production conditions is 1.4-2.0 eV).

At present, as shown below, the major structure of the material used for the metal-containing electron transport layer is a bi-dentate structure that has two non-shared electron pairs and is bonded to a metal via two coordinate bonds.

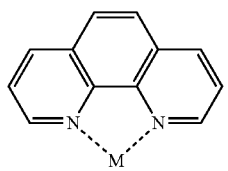

Bonding of this structure to the metal is relatively strong, which can suppress the occurrence of the following situations: heat and electric field generated during the driving of the device will cause the metal to move, thus causing an arrangement change of the electron transport layer at an initial driving stage and changing the characteristics of electron injection and movement. Eventually, a lifetime of the device is shortened.

Compared with a mono-dentate electron transport layer material or an electron transport layer material that is incapable of coordinately bonding, the bi-dentate electron transport layer material has higher stability and longer lifetime. Nevertheless, there is still an issue of increased drift voltage, and also a need for further improvement in terms of lifetime.

In addition, as for the most-used phenanthroline, it is difficult to control the evaporation rate due to its small molecular weight. Further, its flat-plane molecular structure leads to strong intermolecular attraction forces, which may cause blocking of the entrance of the crucible during the evaporation process or cause accumulation of substantial materials on the baffle on the inner wall of the chamber, which is disadvantageous to the manufacturing process.

Therefore, there is presently a need to design and develop stable and efficient electron transport materials having high electron mobility and high glass transition temperature to improve the luminous efficiency of the device and prolong the lifetime of the device.

SUMMARY

In view of the above, the present disclosure provides a compound suitable for use as an electron transport material, the compound having a structure according to general formula 1:

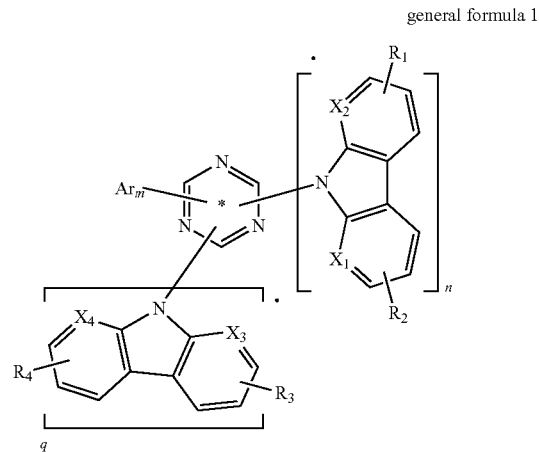

general formula 1 wherein $X_1$-$X_4$ are each independently selected from a carbon atom or a nitrogen atom, and at least two of $X_1$-$X_4$ are each a nitrogen atom;

$R_1$-$R_4$ are each independently absent or selected from the group consisting of a hydrogen atom, a C1-C20 alkyl group, a C1-C20 alkoxy group, a C1-C20 alkylthio group, a C1-C20 alkylamino group, a C6-C30 aryl group, and a C2-C30 heteroaryl group;

m is 1 or 2;

n and q are each independently selected from 0, 1, or 2, n+q≥1, and m+n+q=3; and Ar is a C6-C30 aryl group.

The compound of the present disclosure is suitable for use as an electron transport material of an OLED device. The molecular structure of the present disclosure has a multidentate nitrogen-containing ligand which can be complexed with metal Yb or LiQ to form an organometallic complex with multidentate bonded metal. Therefore, the heat and electric field generated during the device driving process that cause movement of the metal can be effectively alleviated. Meanwhile, in the molecule of the present disclosure, the triazine skeleton structure cooperates with multiple substituents having large steric hindrance, in such a manner that the organic compound of the present disclosure has large rigid twist, and avoids increases in intermolecular attraction resulting from an excessively planar structure of conventional triazine compounds. The organic compound of the present disclosure has a spatial structure and an appropriate molecular weight in the range of 600-1200 g/mol suitable to control the evaporation rate and inhibit the accumulation caused by the increase of intermolecular attraction. These factors work together to lower a turn-on voltage of the OLED device, reduce an operating voltage of the OLED device, and improve a luminous efficiency of the OLED device, while prolonging lifetime of the OLED device.

In addition, the present disclosure further provides a display panel and a display apparatus including the compound as mentioned above.

DESCRIPTION OF EMBODIMENTS

Figure 1:
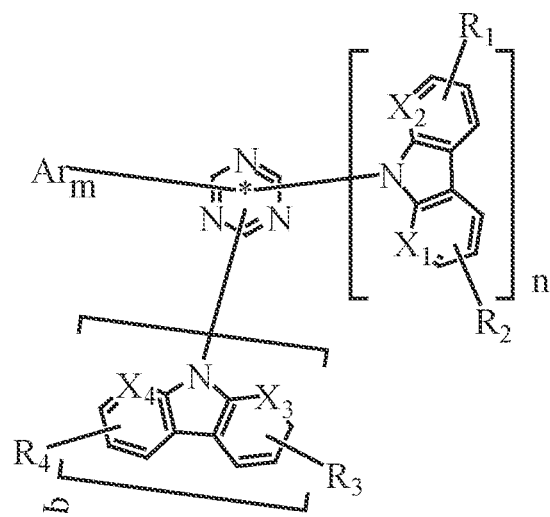
FIG. 1 is a general formula of a compound, according to the present disclosure.
Figure 2:
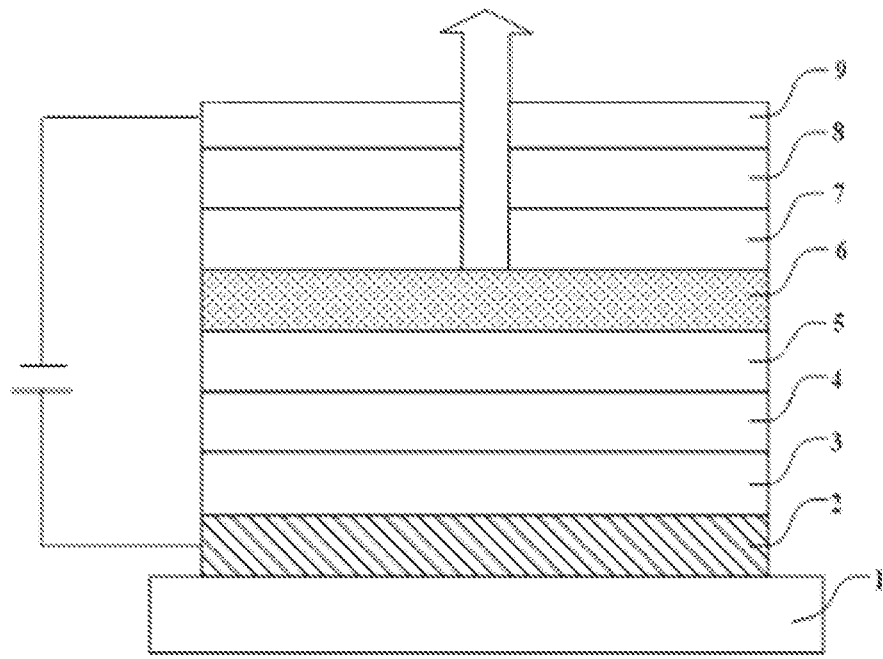
FIG. 2 is a schematic diagram of an OLED device, according to an embodiment of the present disclosure.

The present disclosure will be further described below with reference to embodiments and comparative examples. It should be understood that the present disclosure is not limited the following embodiments. Without departing from the scope of the technical solutions of the present disclosure, any modifications or equivalent substitutions to the technical solutions of the present disclosure shall fall within the protection scope of the present disclosure.

In one aspect, the present disclosure provides a compound having a structure according to general formula 1:

general formula 1

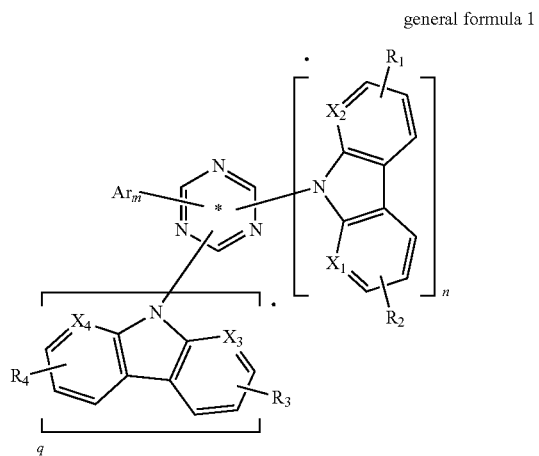

in which, $X_1$-$X_4$ are each independently selected from a carbon atom or a nitrogen atom, and at least two of $X_1$-$X_4$ are each a nitrogen atom;

$R_1$-$R_4$ are each independently absent or selected from the group consisting of a hydrogen atom, a C1-C20 alkyl group, a C1-C20 alkoxy group, a C1-C20 alkylthio group, a C1-C20 alkylamino group, a C6-C30 aryl group, and a C2-C30 heteroaryl group;

m is an integer selected from 1 or 2;

n and q are each integers independently selected from 0, 1, or 2, n+q≥1, and m+n+q=3; and Ar is a C6-C30 aryl group.

The compound of the present disclosure is suitable for use as an electron transport layer material suitable to form a tri-dentate or tetra-dentate bond with Liq or metal ytterbium, which improves the bonding strength between the metal and the organic compound. The compound of the present disclosure forms robust bonding with the metal, which alleviates disadvantageous metal migration inside the device due to the heat and electric field generated during long-term operation of the device. At present, conventional electron transport materials used in OLED devices generally contain a chemical structure of triazine. This chemical structure, due to its good planarity, leads to increased intermolecular interaction forces, which causes adverse effects, such as a rise in vapor-deposition temperature and an increase in energy consumption of vapor-deposition equipment. Meanwhile, the increase in vapor-deposition temperature makes the material become less stable, resulting in a reduction in lifetime of the device. In order to overcome the above shortcomings, in the compound molecules of the present disclosure, multiple substituents with large steric hindrance are connected to the triazine skeleton structure so that the organic compound of the present disclosure has large rigid twist, and avoids or reduces increased intermolecular attraction of conventional materials resulting from the excessively planar structure of traditional triazine compounds. Meanwhile, the organic compound of the present disclosure has a spatial structure and an appropriate molecular weight in the range of 600-1200 g/mol suitable to control the vapor-deposition rate and inhibit the accumulation caused by the increase of intermolecular attraction. These factors work together to lower the turn-on voltage of the OLED device, reduce the operating voltage of the OLED device, and improve the luminous efficiency of the OLED device, while prolonging lifetime of the OLED device compared to conventional OLED devices.

In the present disclosure, the compound used as the electron transport layer material has any one of the following structures:

Formula 2-1

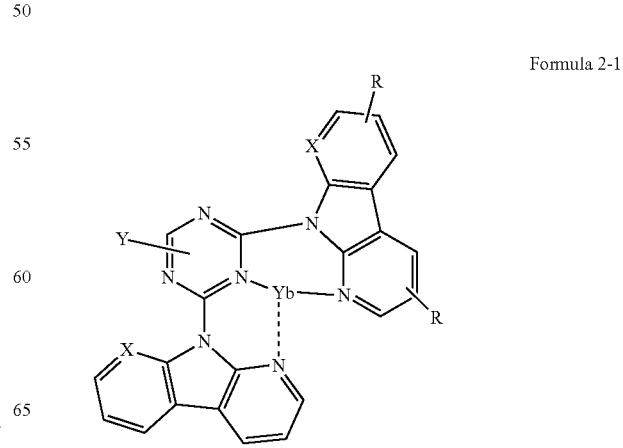

-continued

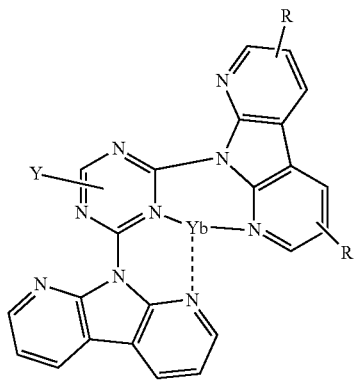
Formula 2-2

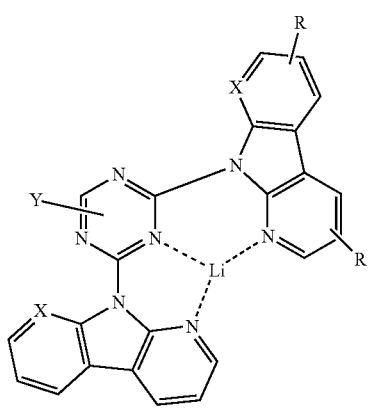
Formula 2-3

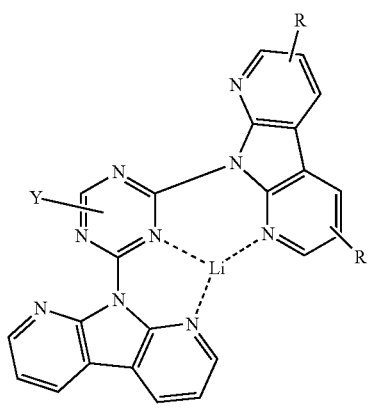
Formula 2-4

In an embodiment of the compound according to the present disclosure, two, three or four of $X_1$-$X_4$ are nitrogen atoms. In order to bond with metals more firmly, in certain embodiments, it is preferable to design and develop materials for electron transport layer that can be tri-dentate or tetra-dentate bonded with metal lithium, lithium organic complexes, or metal ytterbium. Generally, the greater the number of nitrogen atoms, the stronger the bonding force with the metal, and the easier it is to improve the electron transport capacity.

In an embodiment of the compound according to the present disclosure, m is 1, n is 1, and q is 1.

In an embodiment of the compound according to the present disclosure, m is 2, n is 1, and q is 0.

In an embodiment of the compound according to the present disclosure, Ar is selected from the group consisting of a biphenyl group, a phenanthrenyl group, an anthracenyl group, a fluoranthenyl group, a triphenylene group, a pyrenyl group, and the following groups:

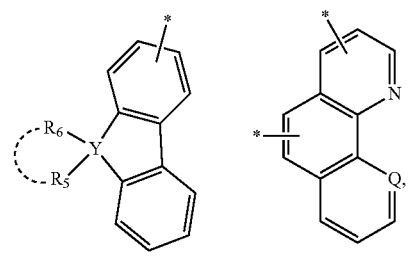

in which, $R_5$ and $R_6$ are each independently absent or selected from the group consisting of a hydrogen atom, a C1-C20 alkyl group, a C1-C20 alkoxy group, a C1-C20 alkylthio group, a C1-C20 alkylamino group, a C6-C30 aryl group, and a C2-C30 heteroaryl group;

$R_5$ and $R_6$ are capable of forming a ring;

Y is selected from the group consisting of a carbon atom, an oxygen atom, a sulfur atom, a boron atom, a phosphorus atom, a P═O group, a silicon atom, and a germanium atom; and when Y is selected from an oxygen atom or a sulfur atom, $R_5$ and $R_6$ are absent;

Q is selected from a carbon atom or a nitrogen atom; and

* indicates a possible bonding position.

In an embodiment of the compound according to the present disclosure, Ar is selected from the following groups:

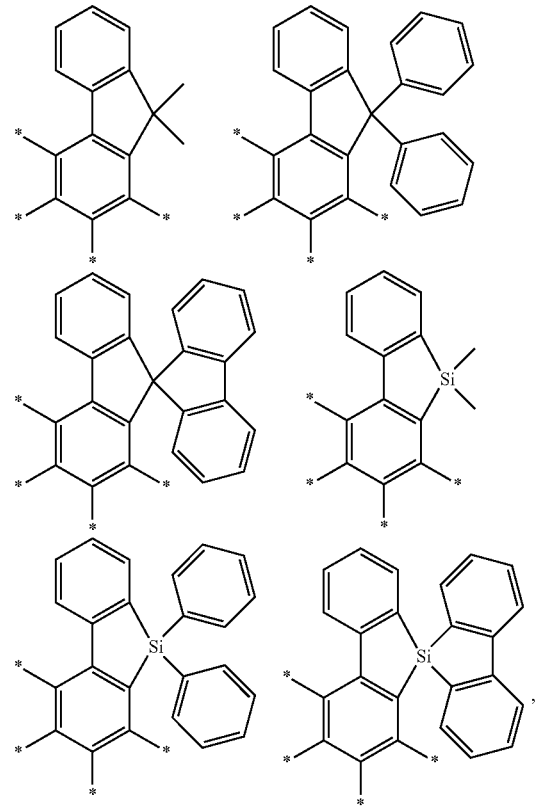

in which, * indicates a possible bonding position.

In an embodiment of the compound according to the present disclosure, Ar is selected from the following groups:

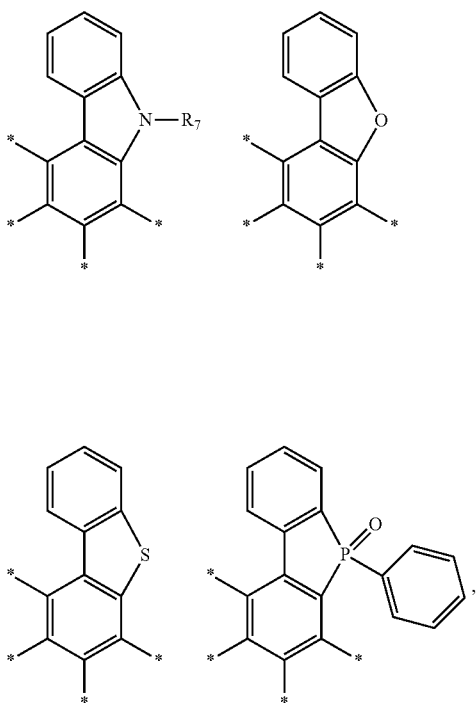

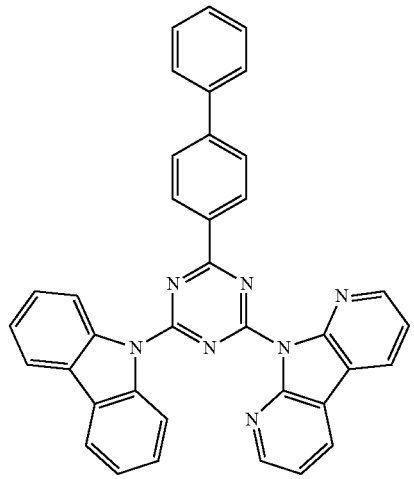

M001 in which $R_7$ is selected from the group consisting of a hydrogen atom, a C1-C6 alkyl group, a C6-C18 aryl group, and a C4-C20 heteroaryl group; and

* indicates a possible bonding position.

In an embodiment of the compound according to the present disclosure, Ar is selected from any one of the following groups:

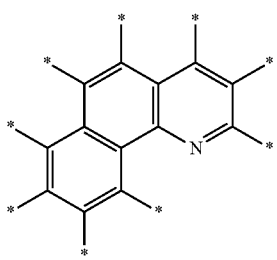

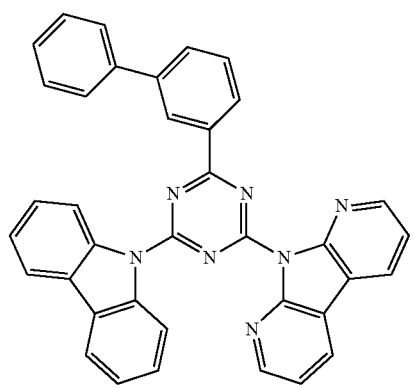

M002

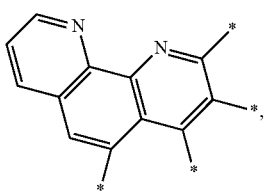

in which * indicates a possible bonding position.

In an embodiment of the compound according to the present disclosure, the compound is any one of the following compounds:

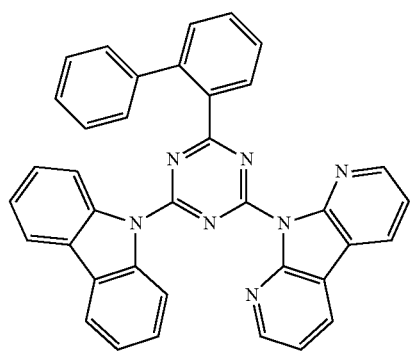

M003

M004
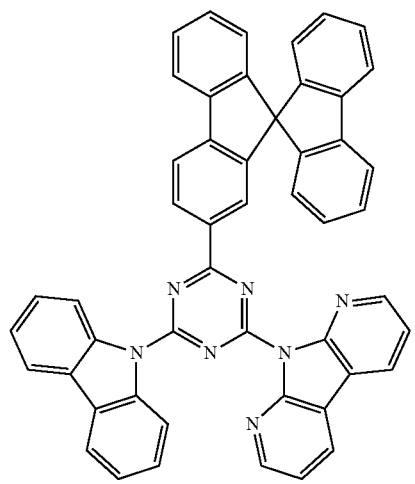
M005
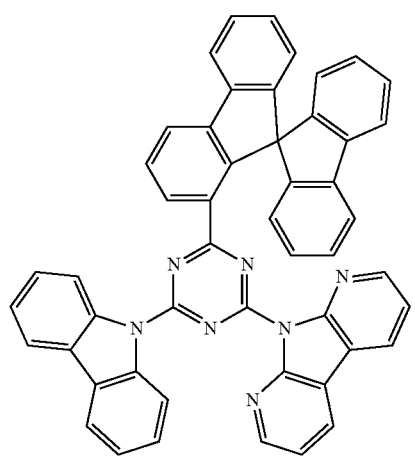
M006
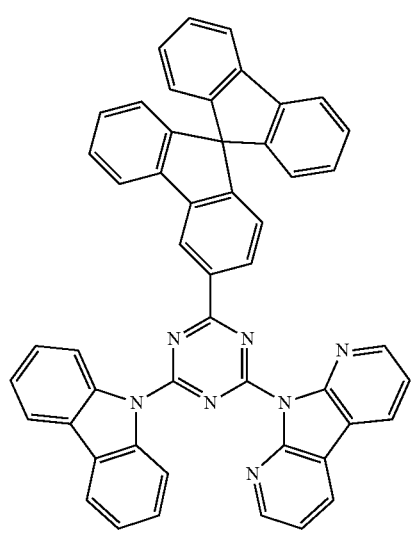
M007
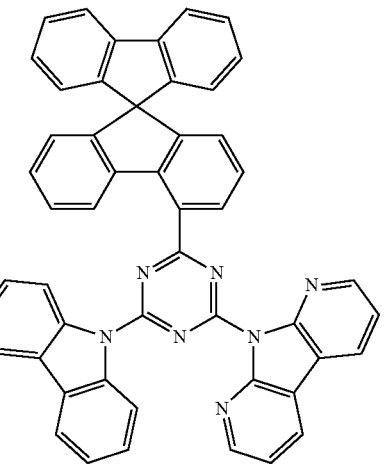
M008
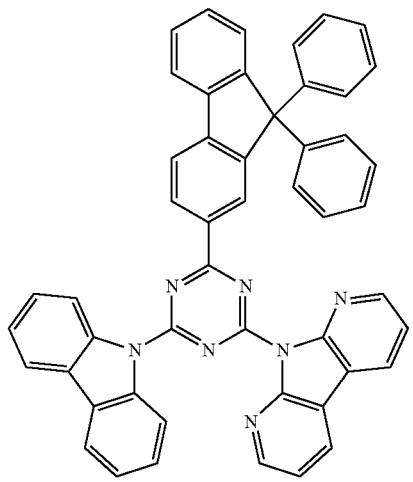
M009
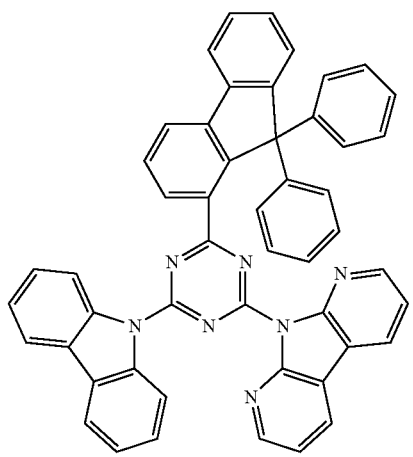

M010
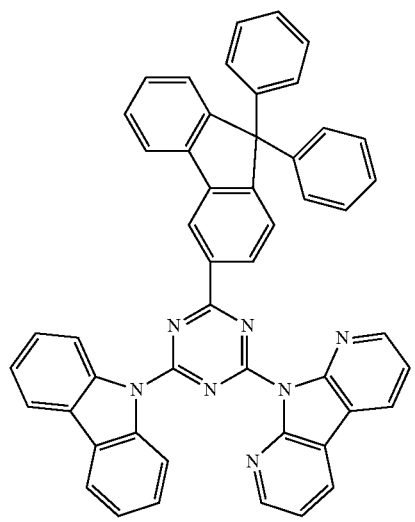
M013
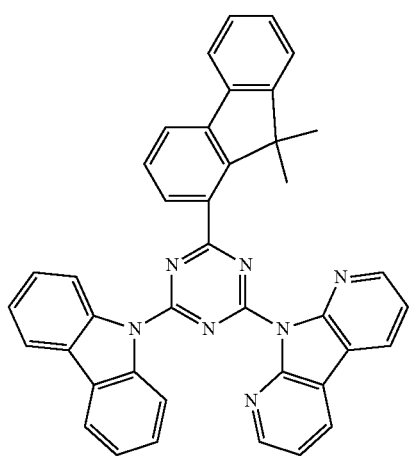
M011
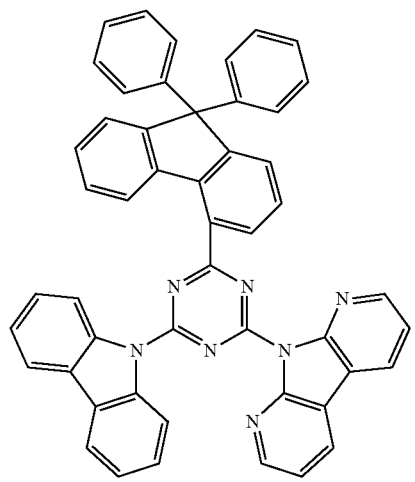
M014
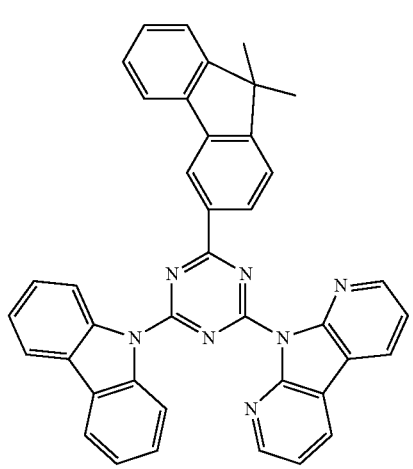
M012
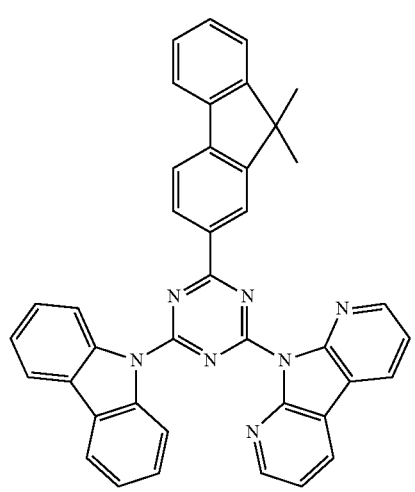
M015
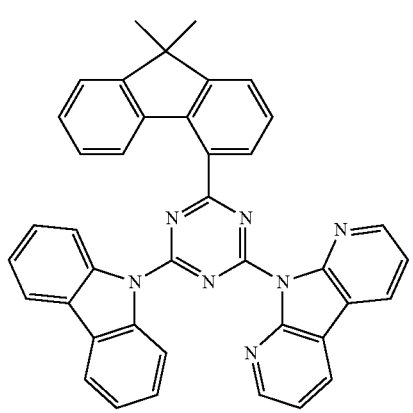

M016
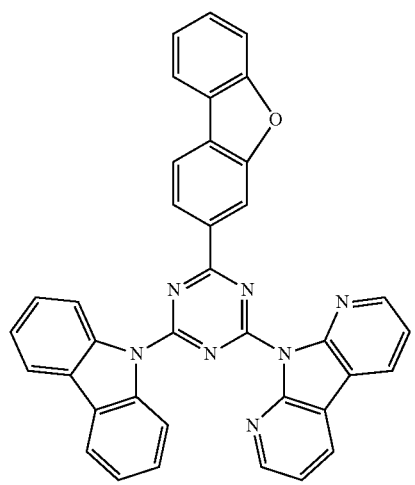
M017
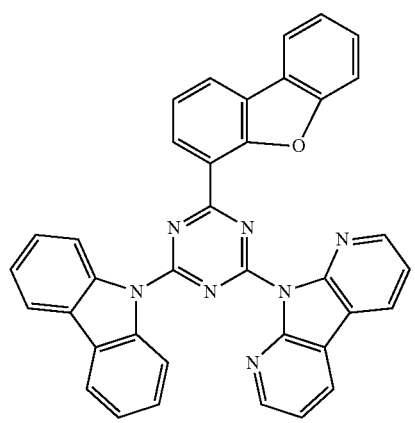
M018
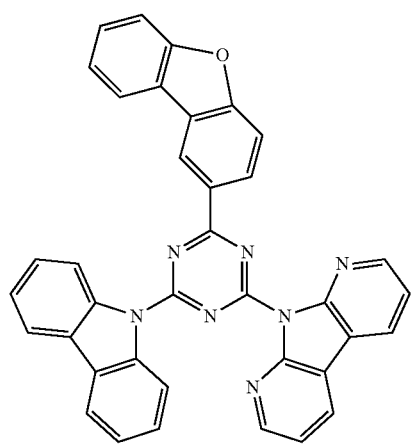
M019
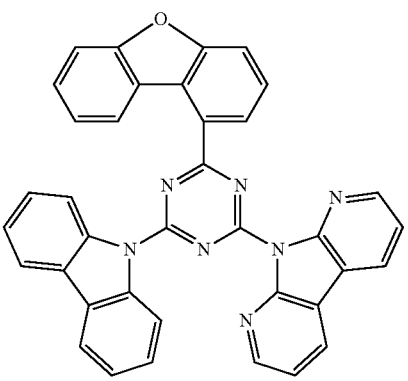
M020
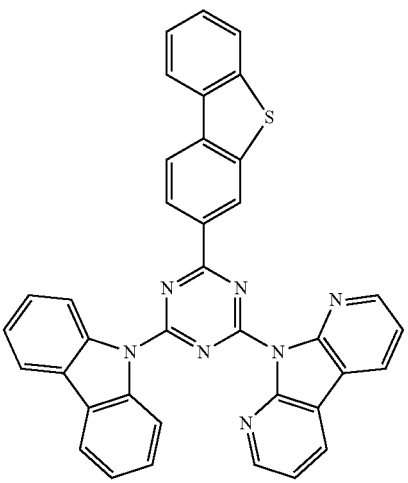
M021
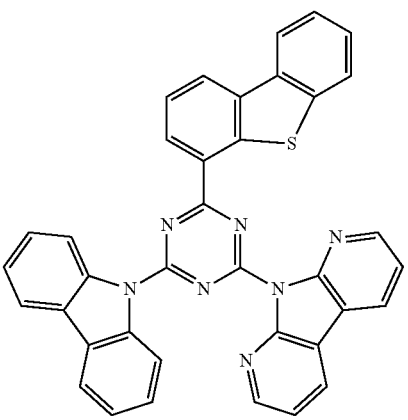

M022
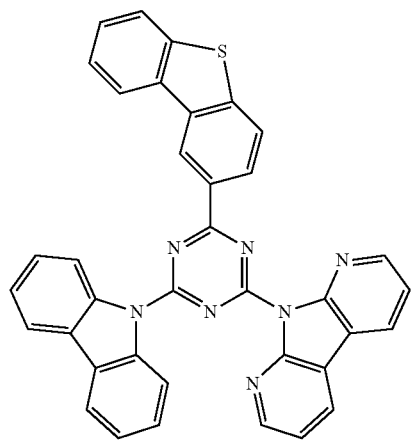
M023
M024
M025
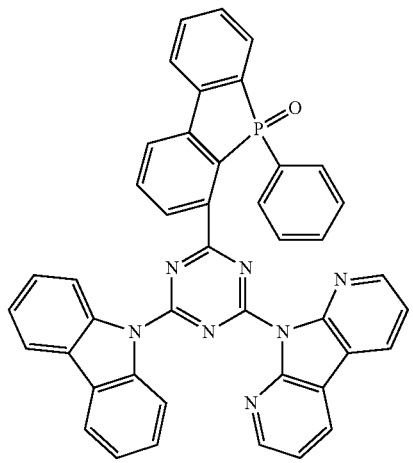
M026
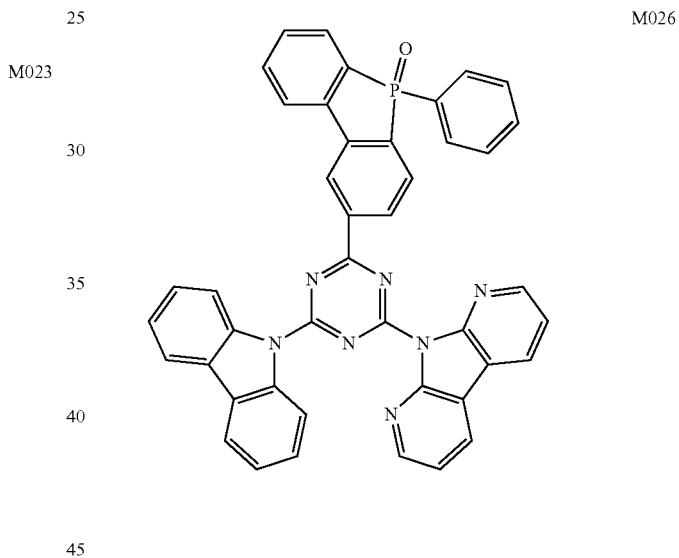
M027
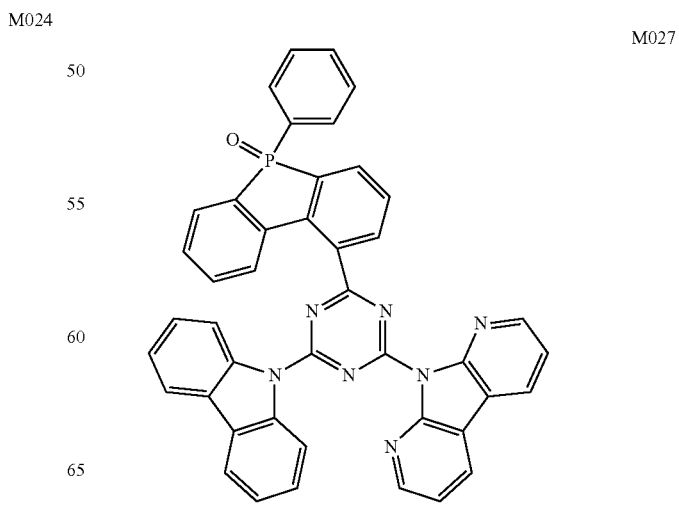

M028
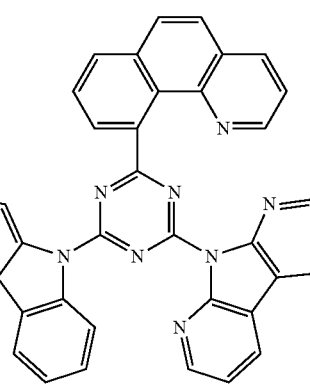
M029
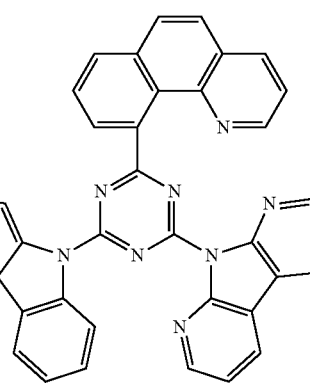
M030
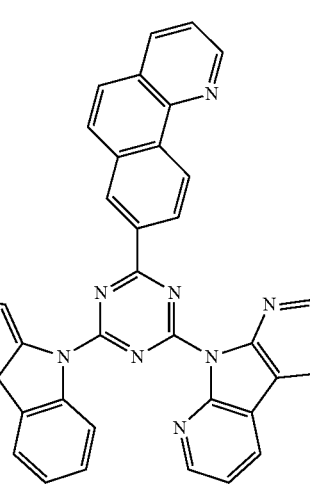
M031
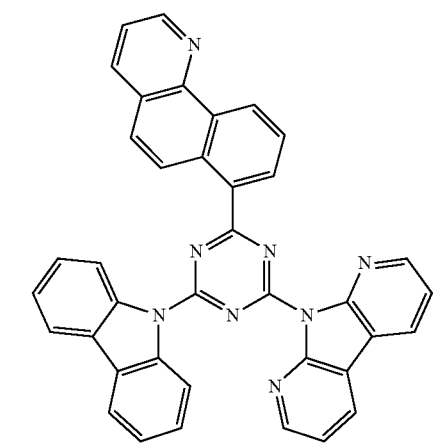
M032
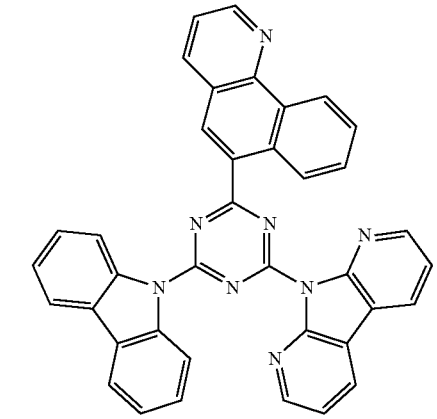
M033
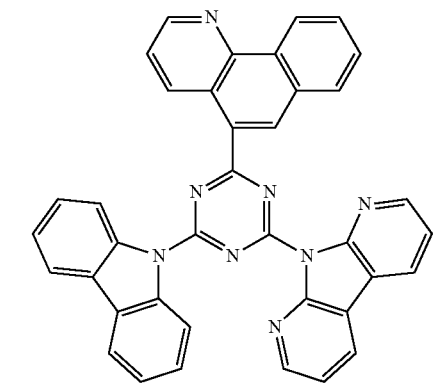
M034
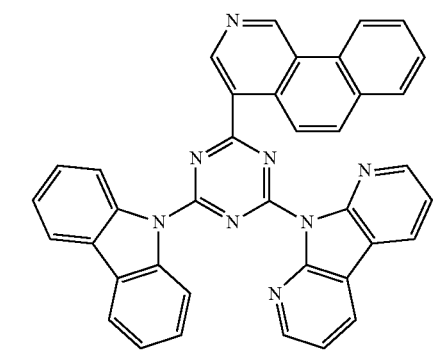

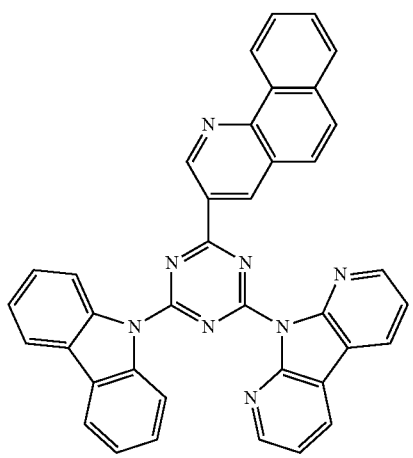
M035
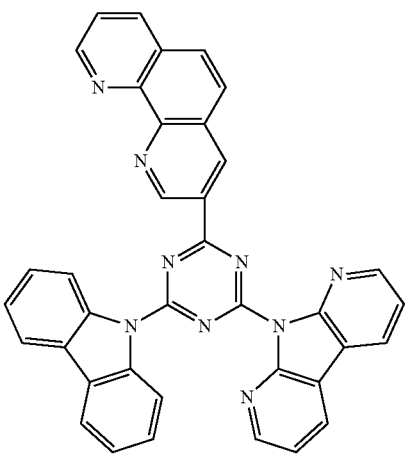
M038
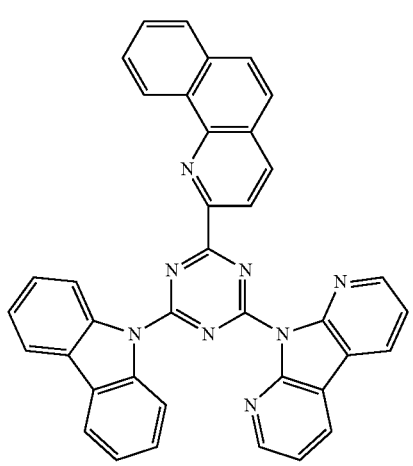
M036
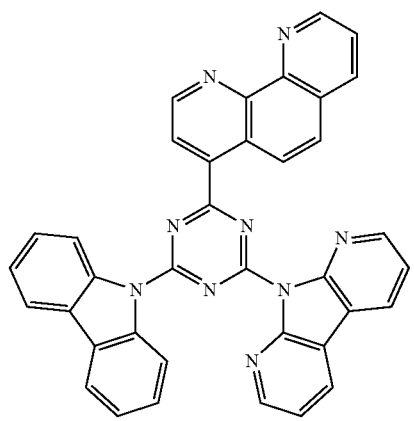
M039
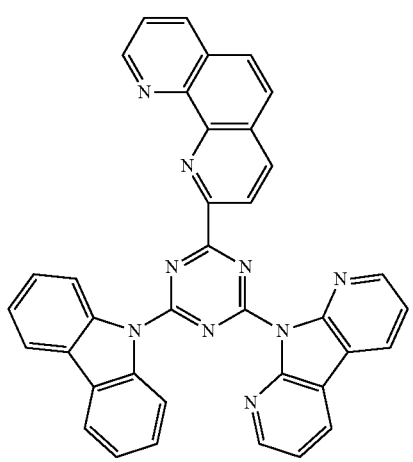
M037
M040

-continued
M041
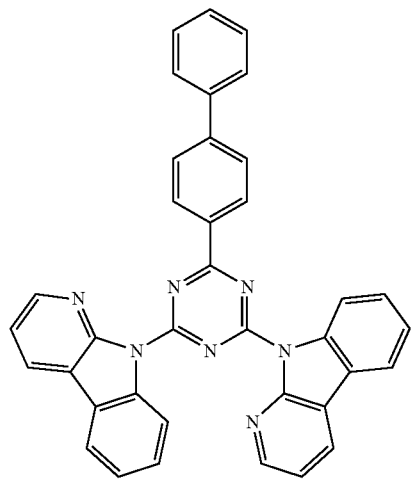
M042
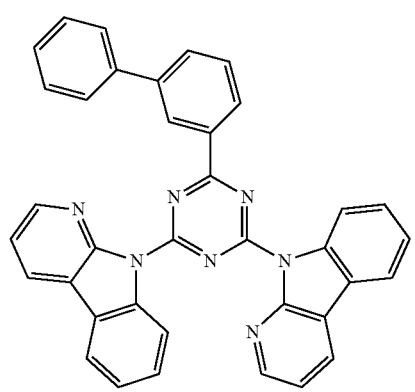
M043
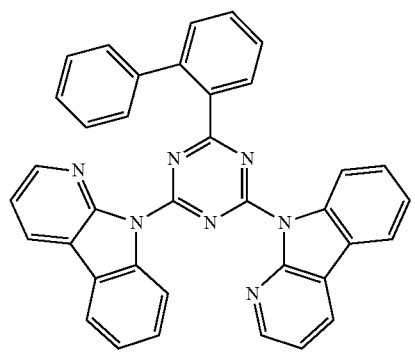
-continued
M044
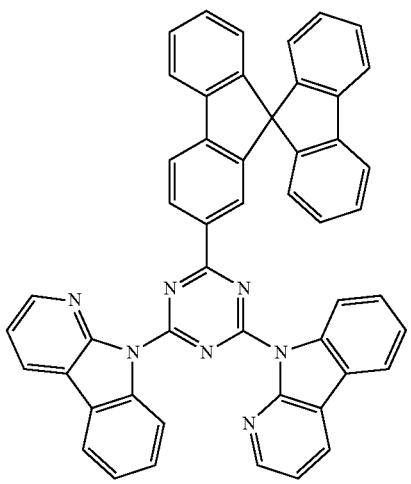
M045
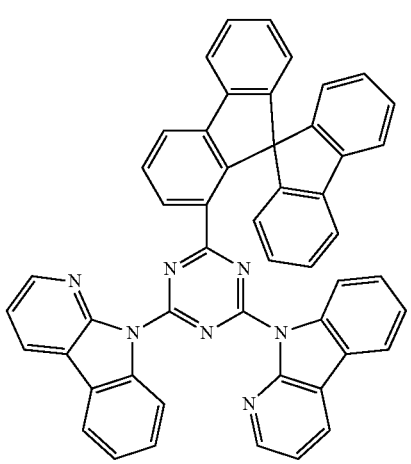
M046
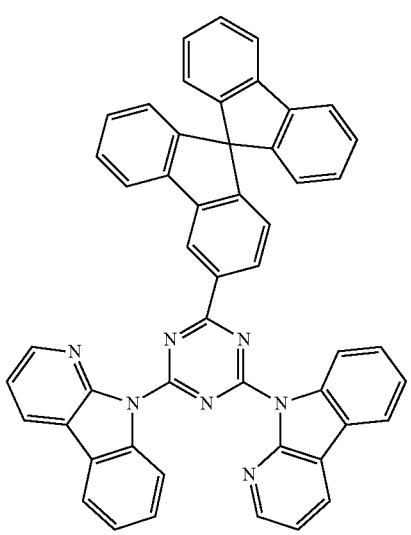

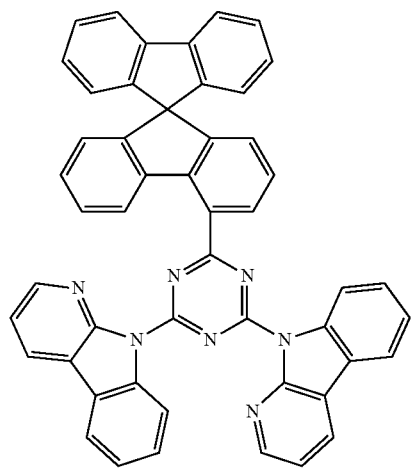 M047
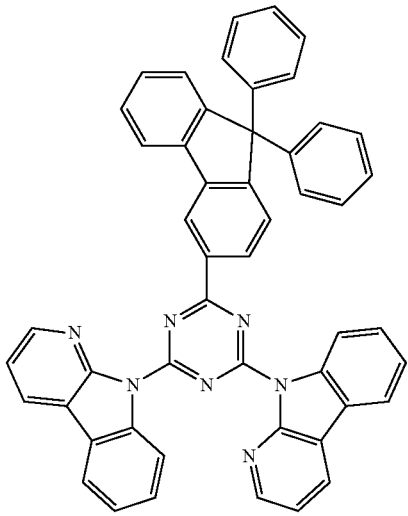 M050
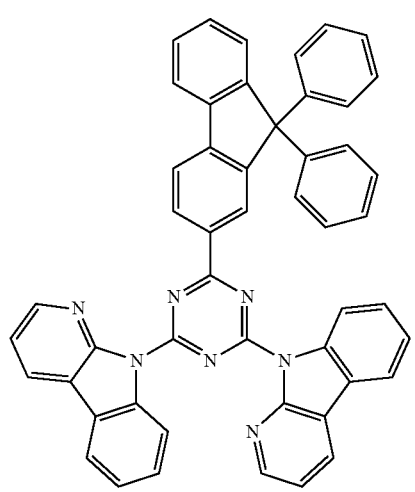 M048
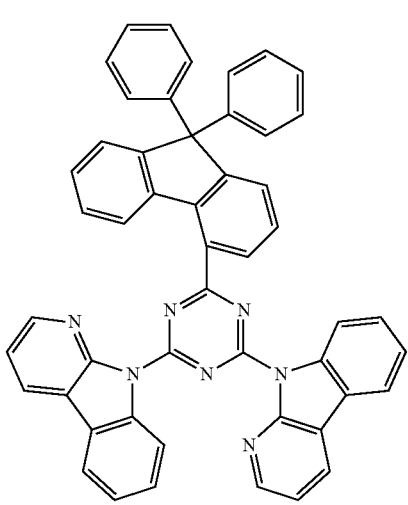 M051
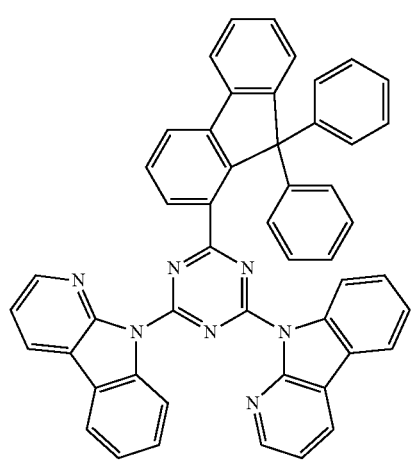 M049
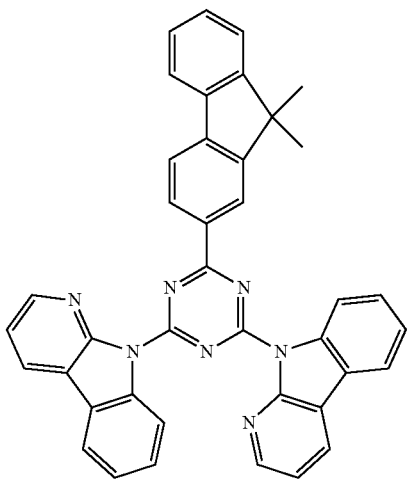 M052

M053
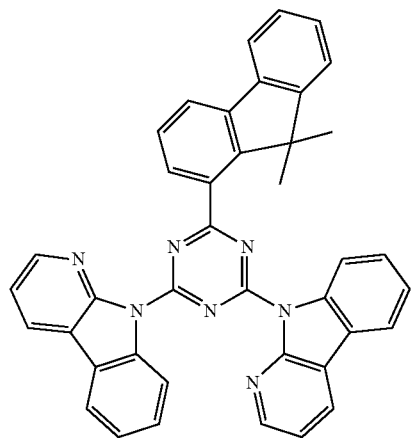
M054
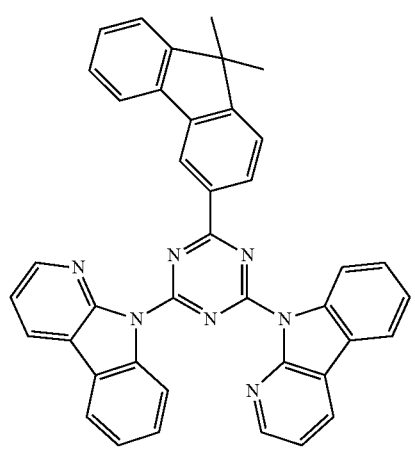
M055
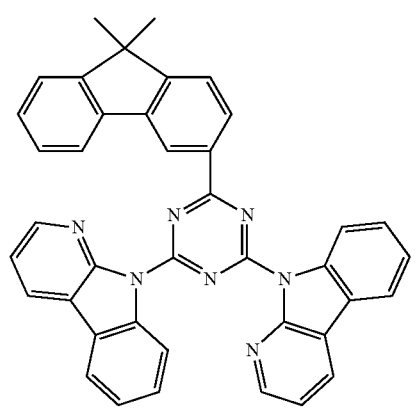
M056
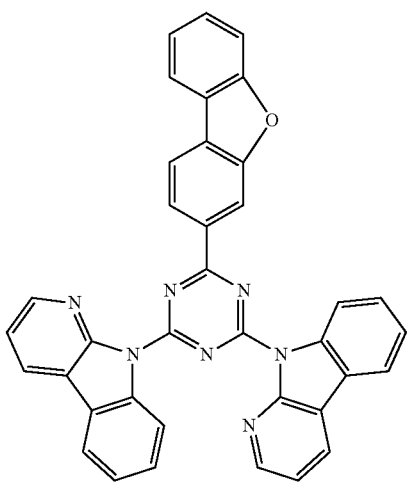
M057
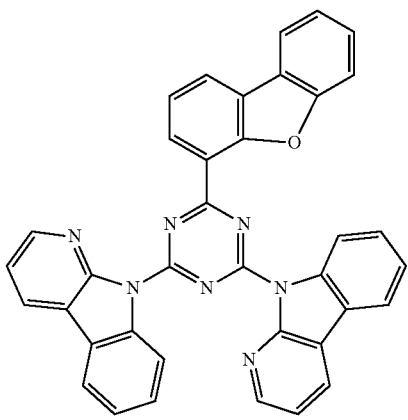
M058
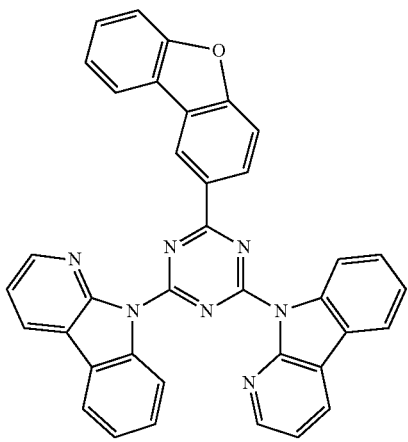

M059
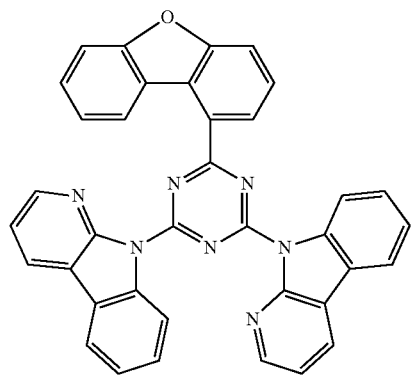
M060
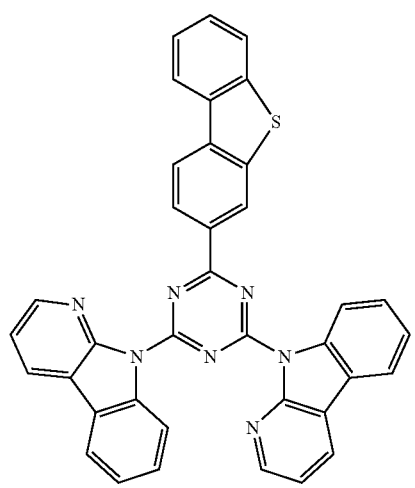
M061
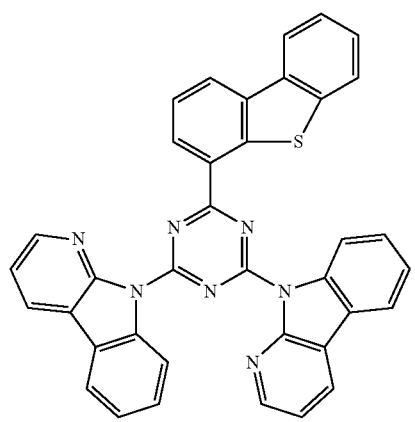
M062
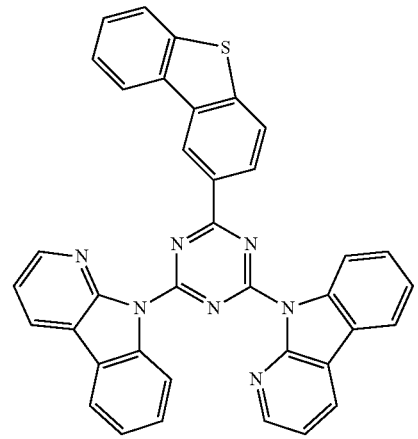
M063
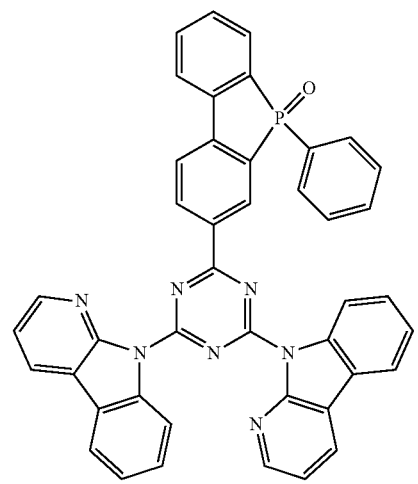
M064

M065
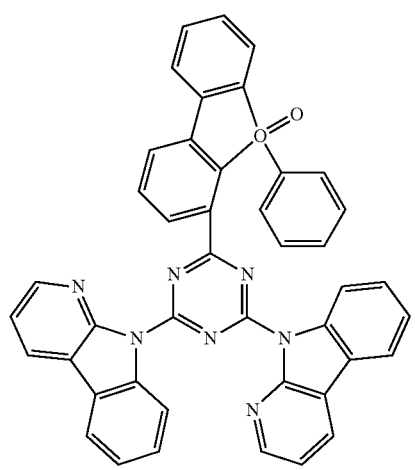
M066
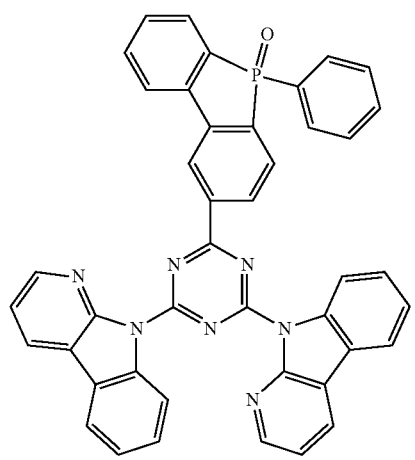
M067
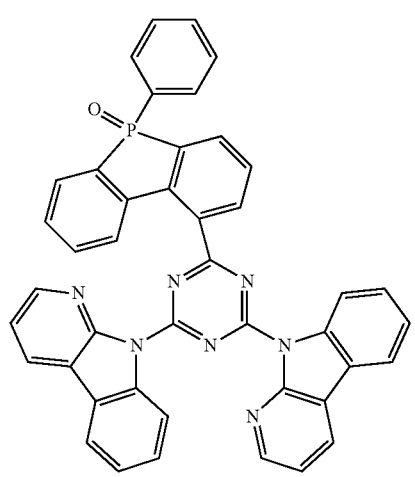
M068
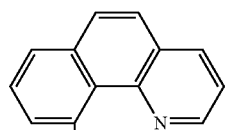
M069
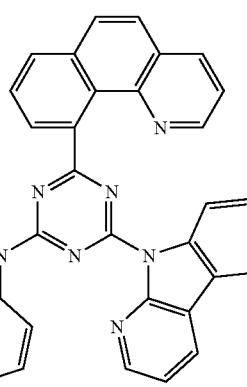
M070
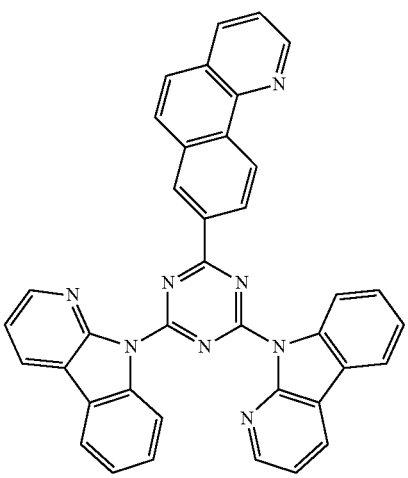

M071
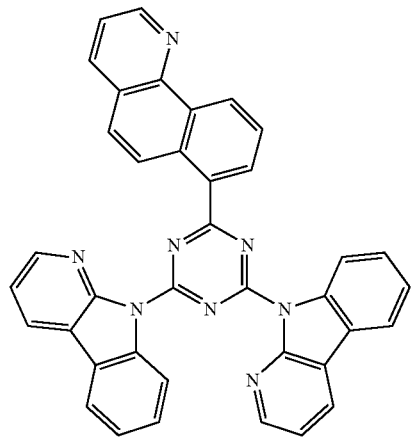
M072
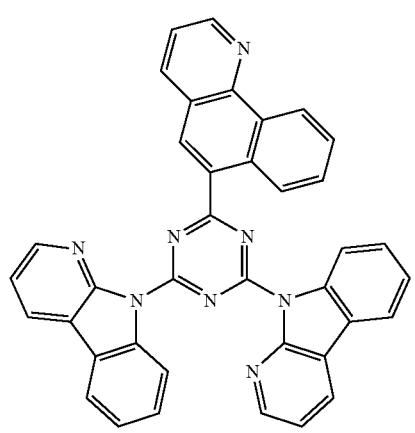
M073
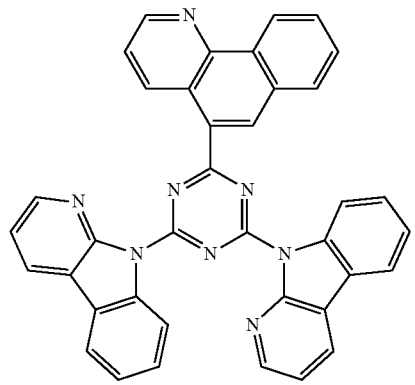
M074
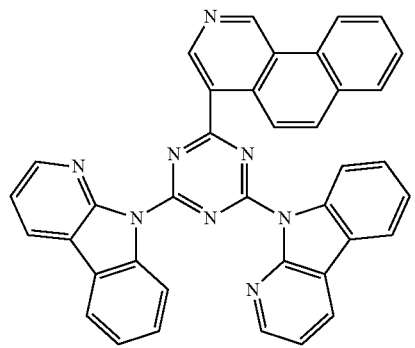
M075
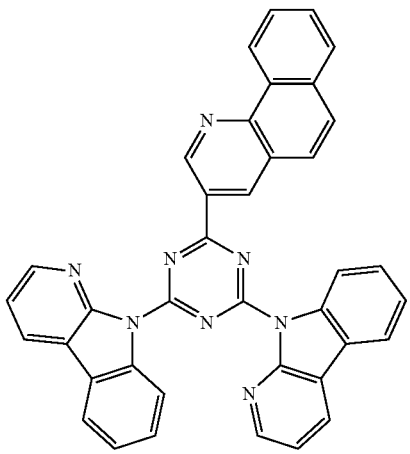
M076
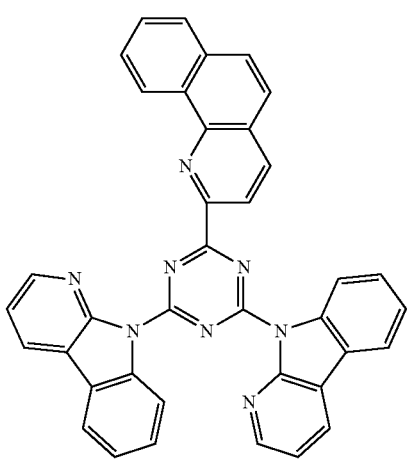
M077
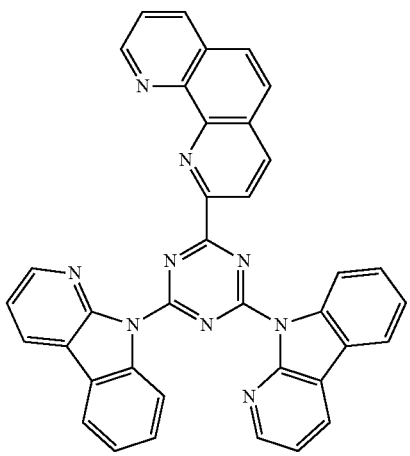

M078
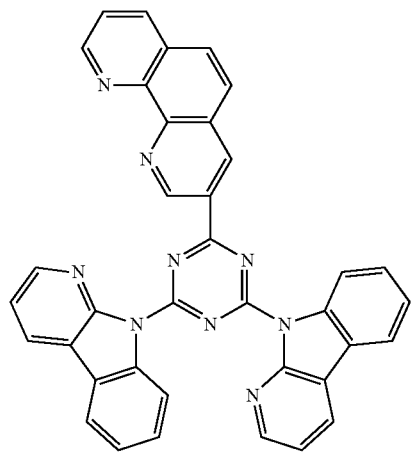
M079
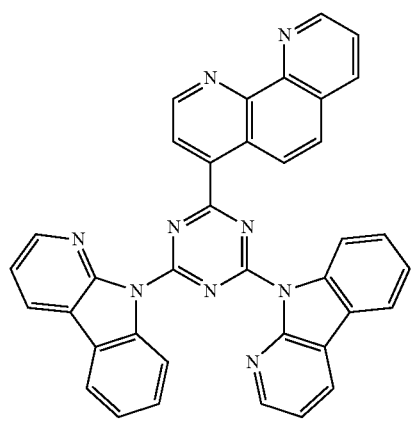
M080
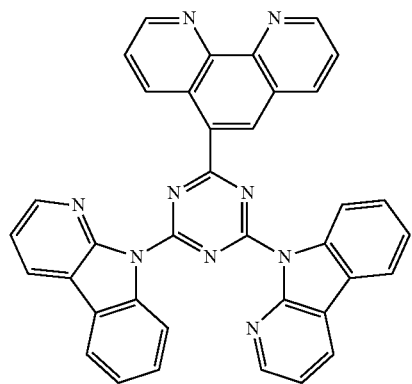
M081
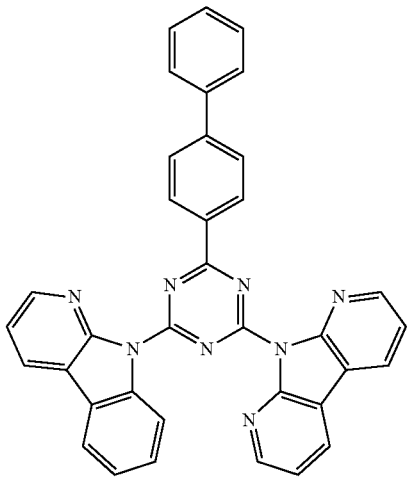
M082
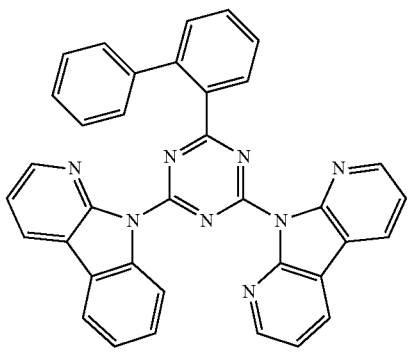
M083

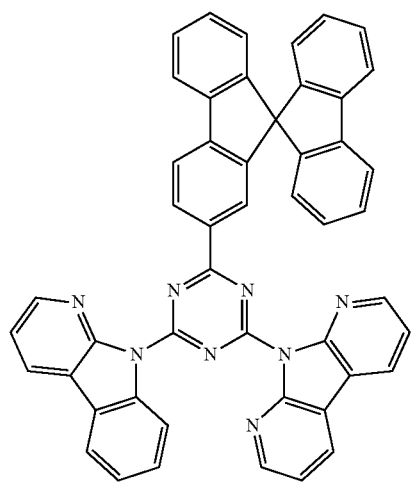
M084
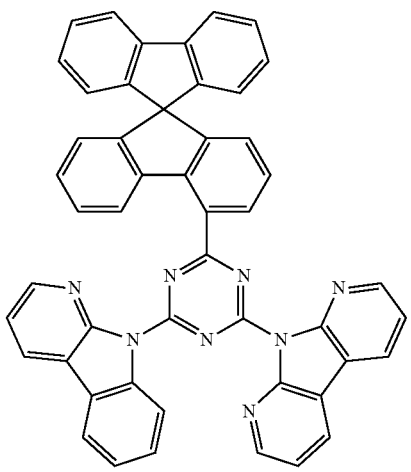
M087
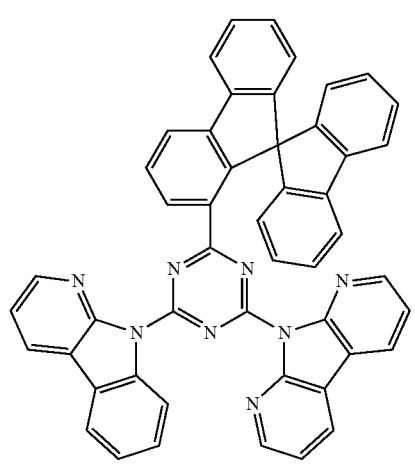
M085
M088
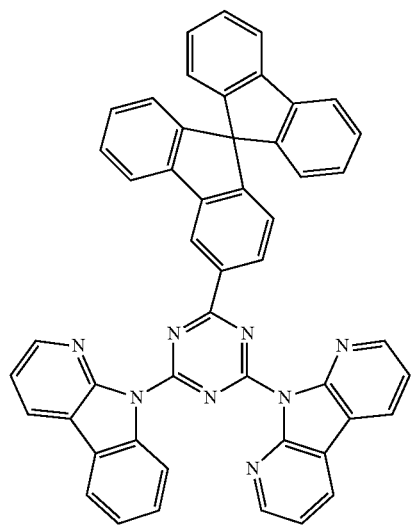
M086
M089

M090
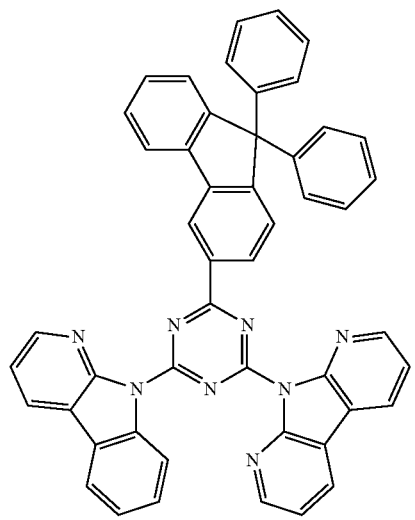
M091
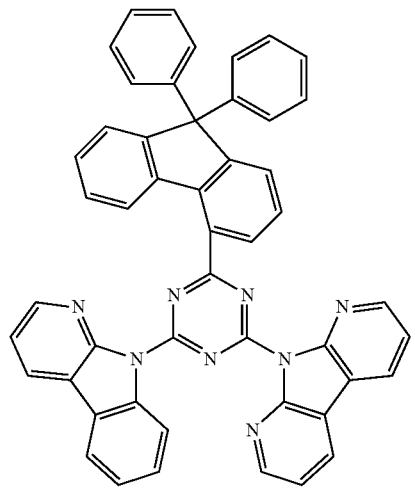
M092
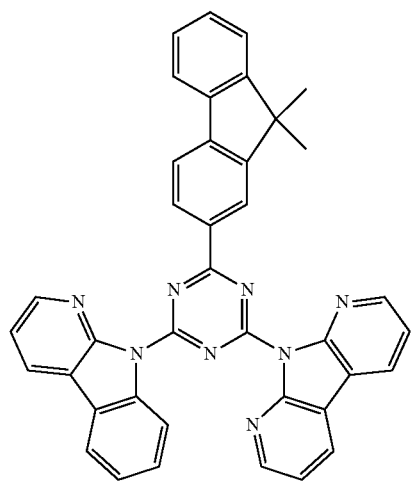
M093
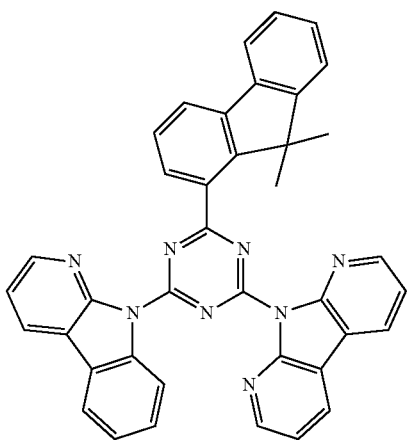
M094
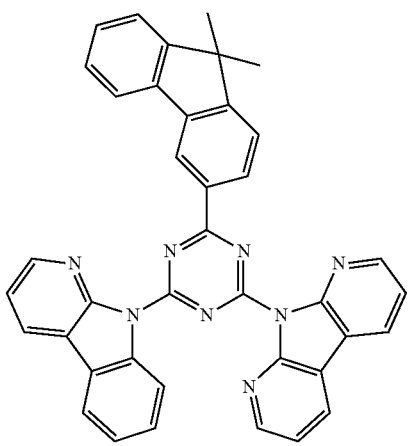
M095
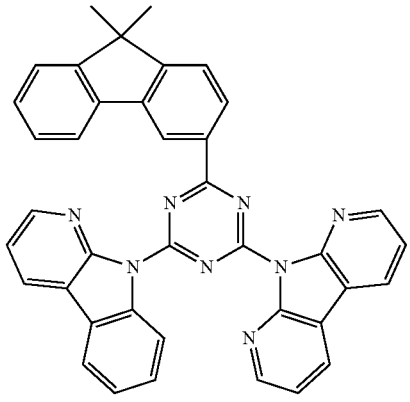

M096
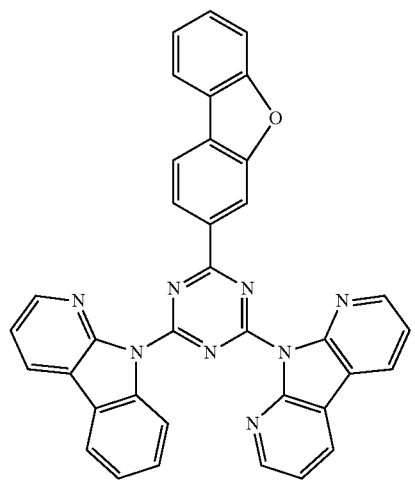
M097
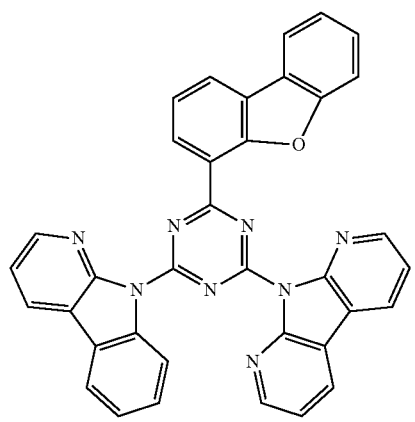
M098
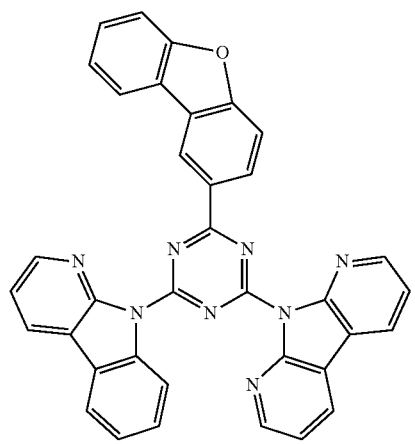
M099
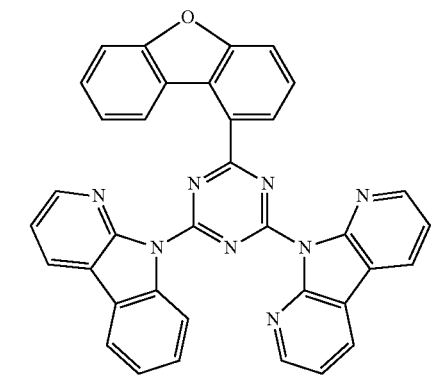
M100
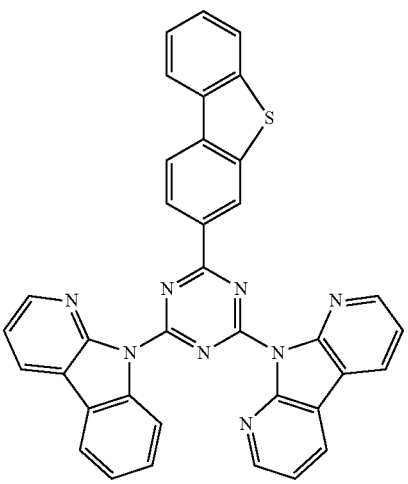
M101
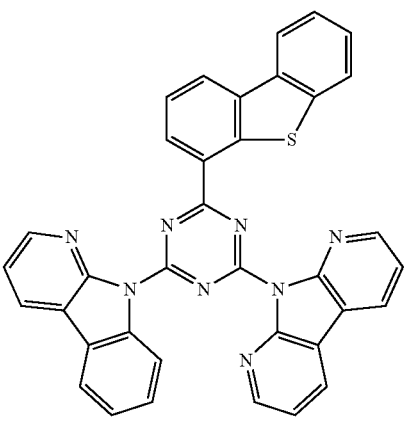

M102
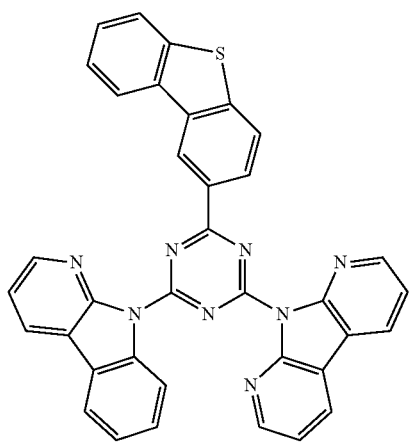
M103
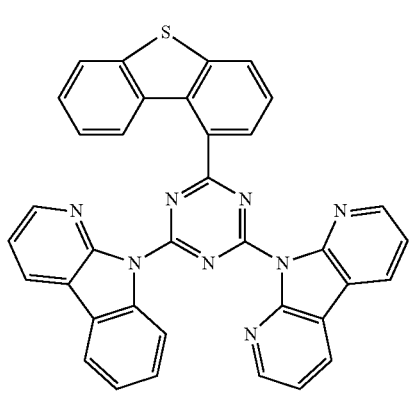
M104
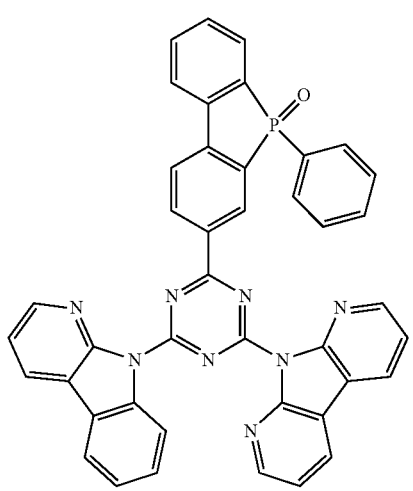
M105
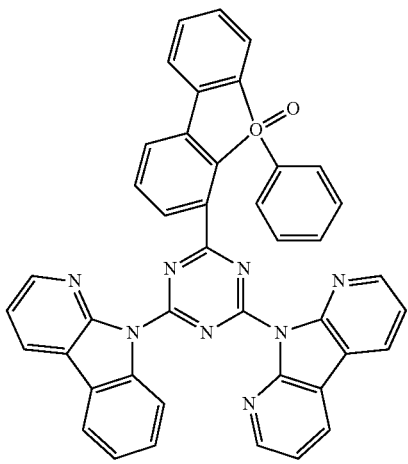
M106
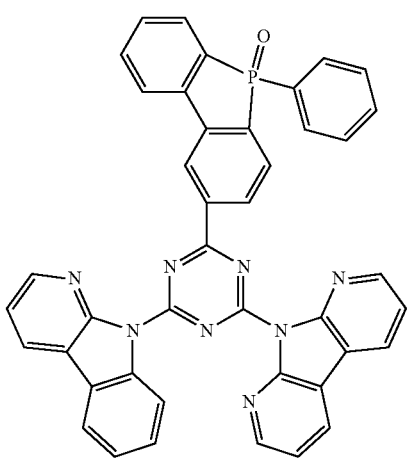
M107
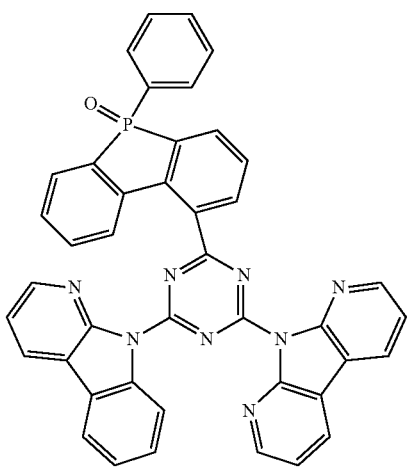

-continued
M108
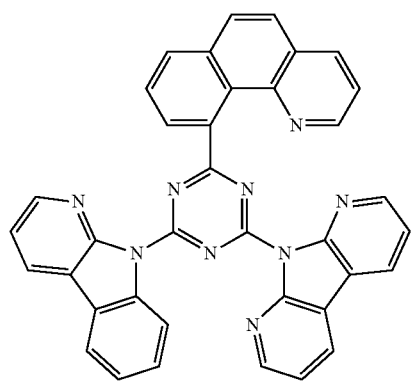
M109
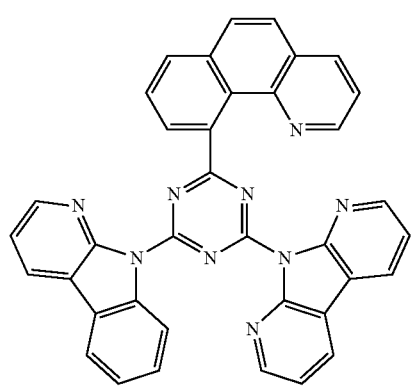
M110
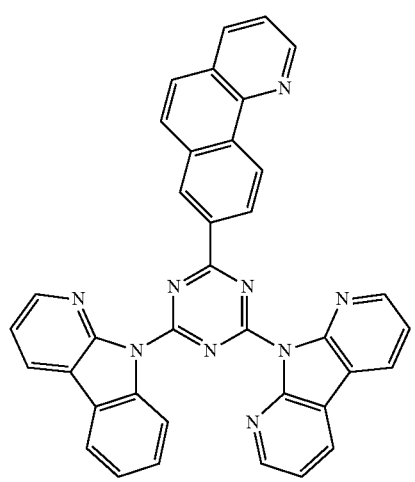
-continued
M111
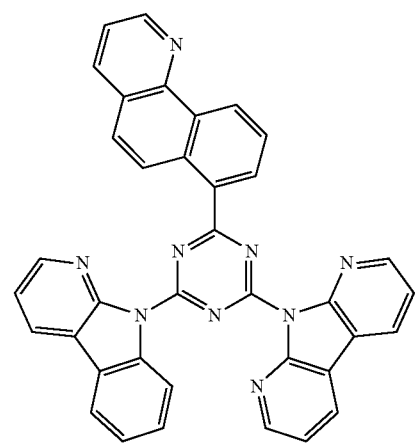
M112
M113
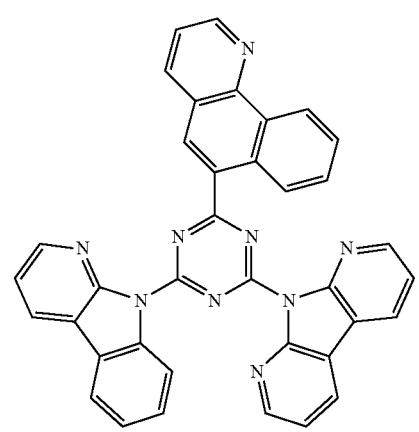
M114
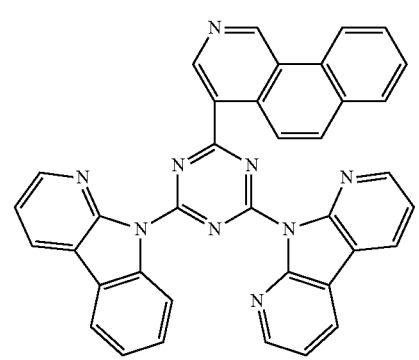

M115
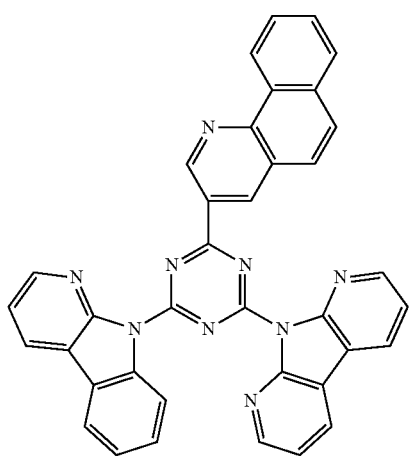
M116
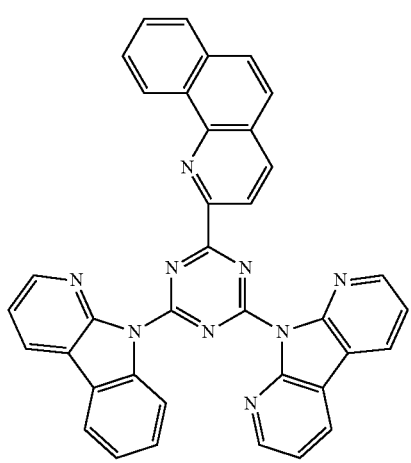
M117
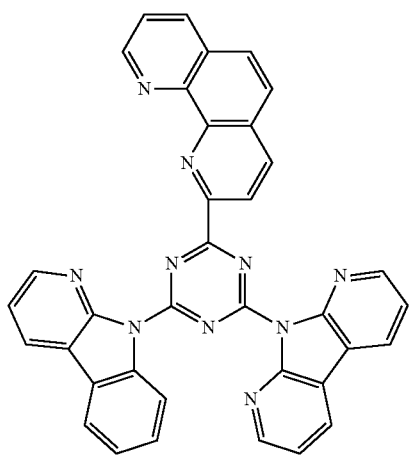
M118
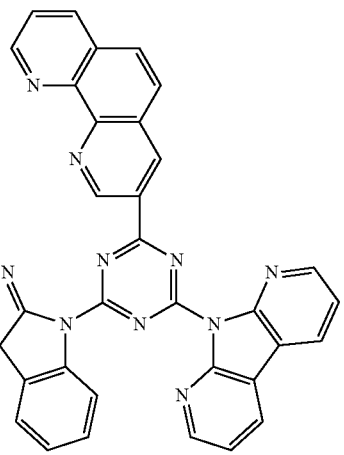
M119
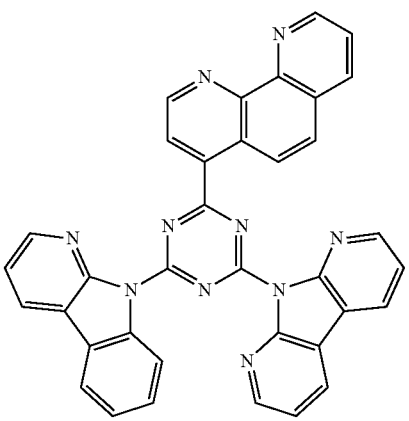
M120
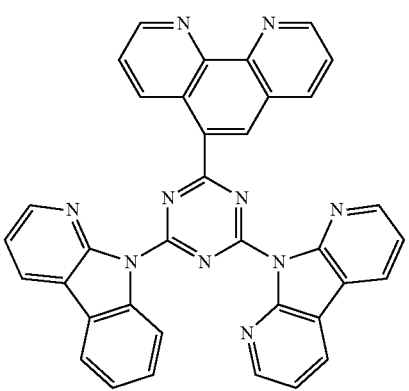

M121
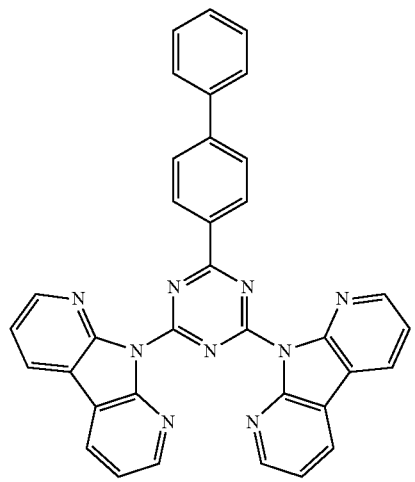
M122
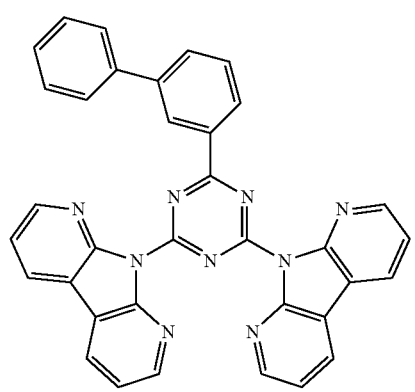
M123
M124
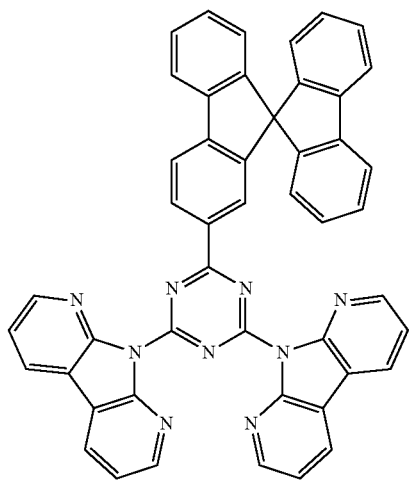
M125
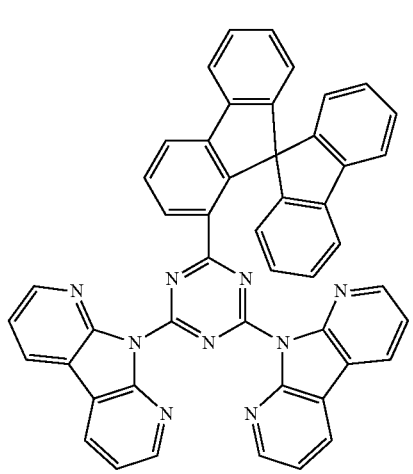
M126
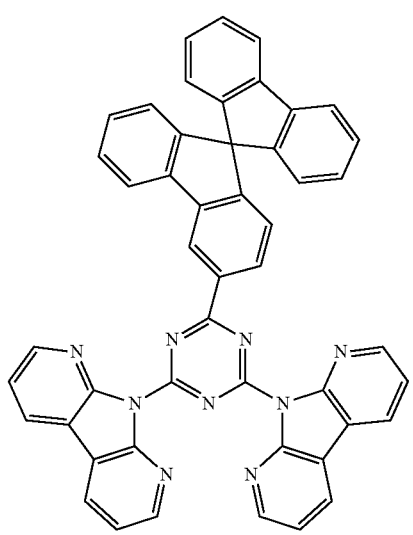
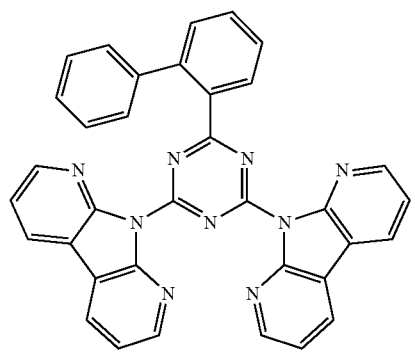

M127
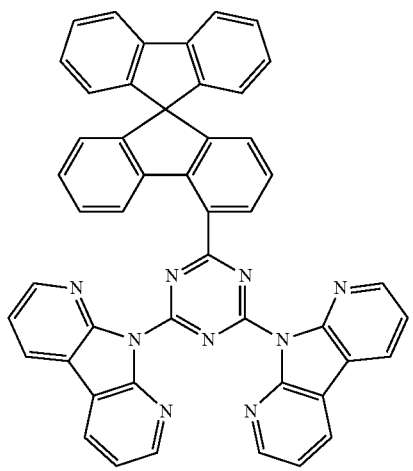
M128
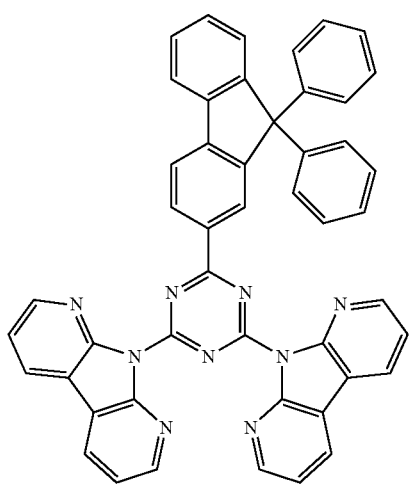
M129
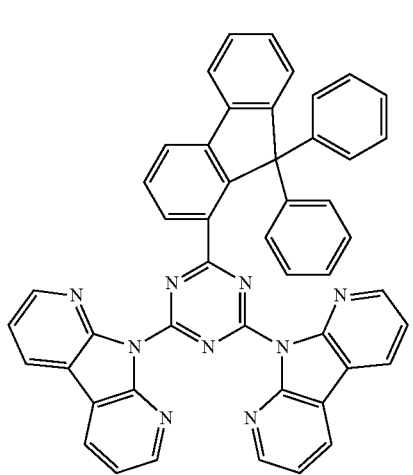
M130
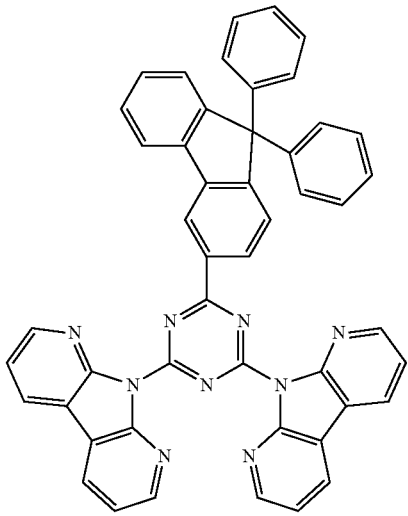
M131
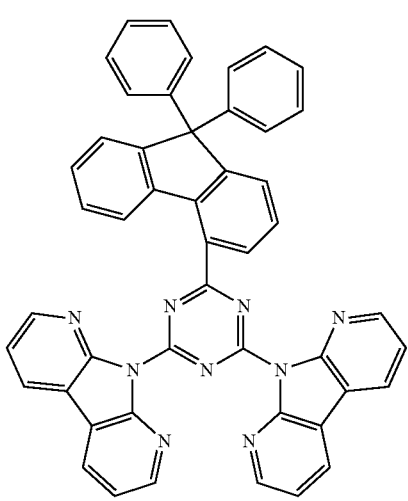
M132
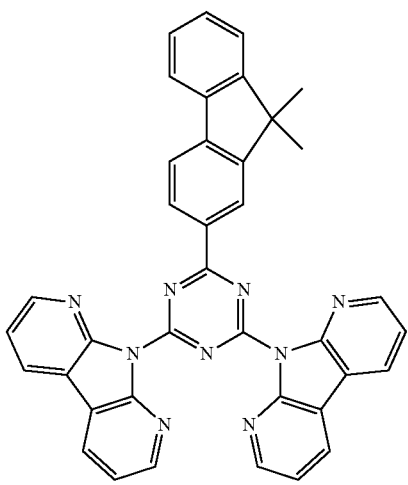

M133
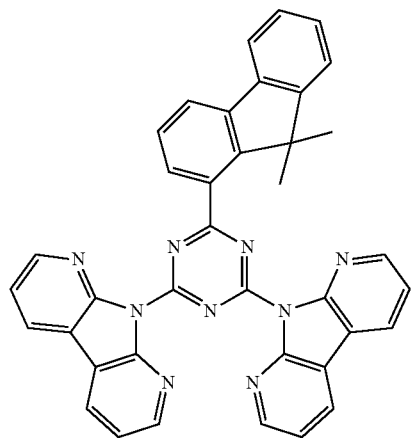
M134
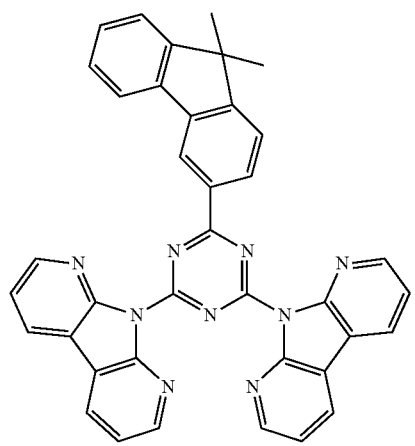
M135
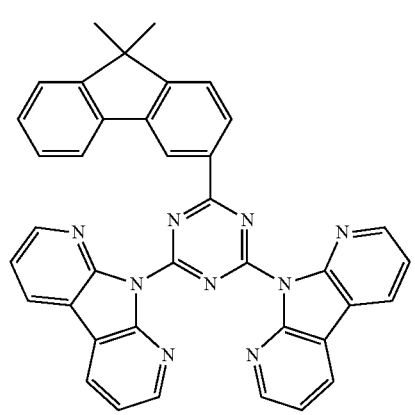
M136
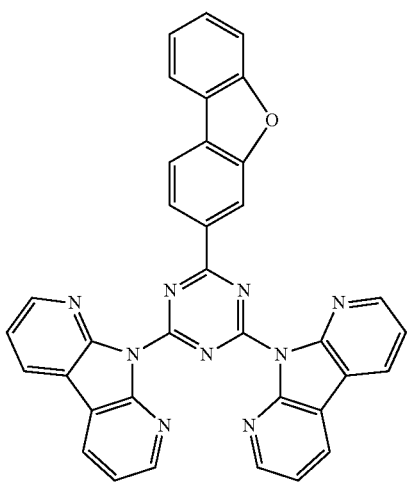
M137
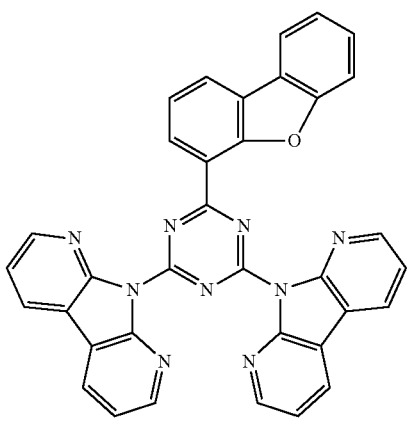
M138
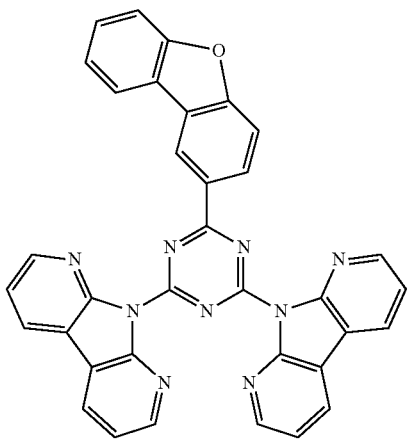

M139
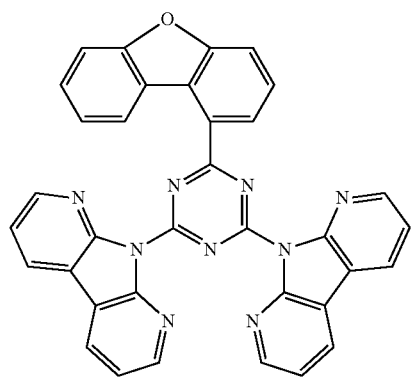
M140
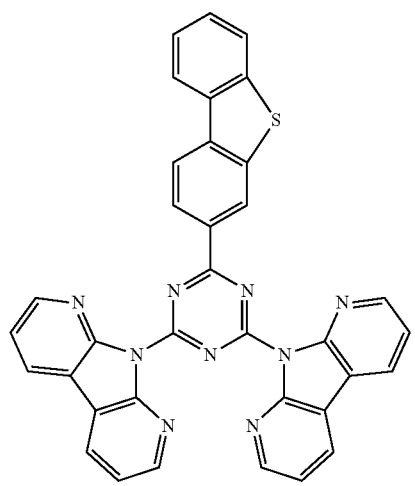
M141
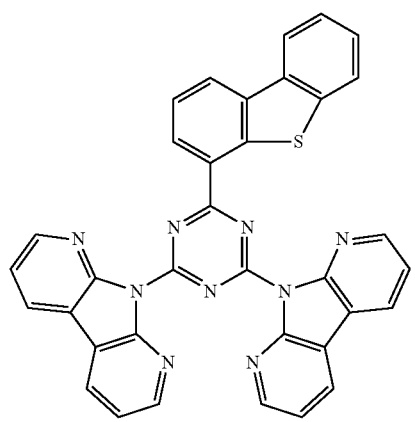
M142
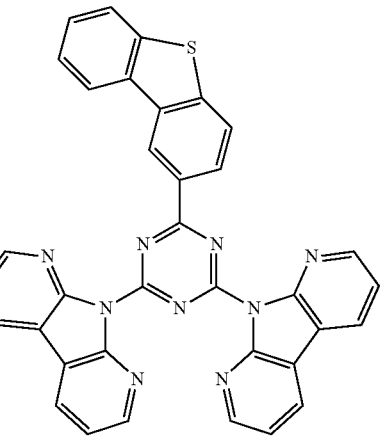
M143
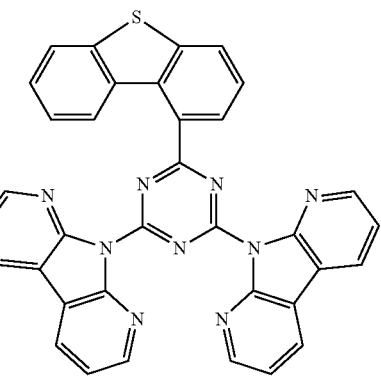
M144
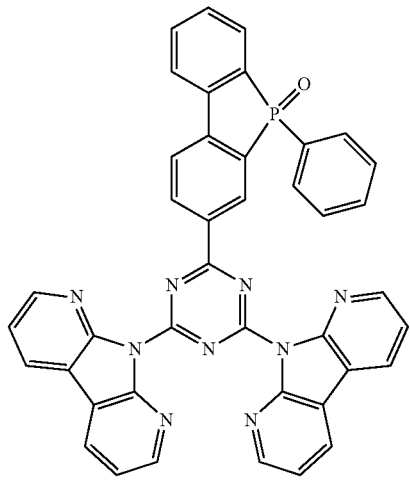

M145
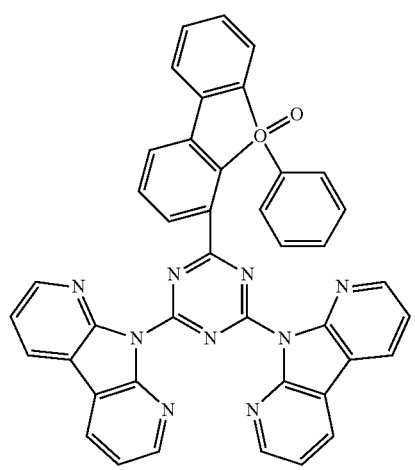
M146
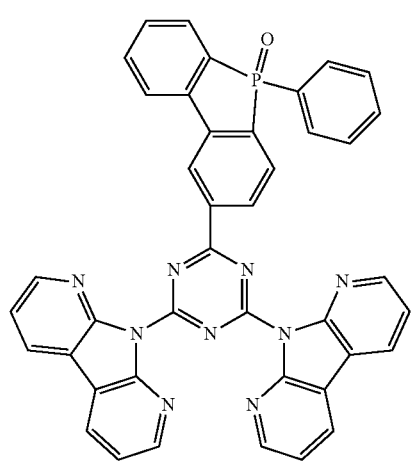
M147
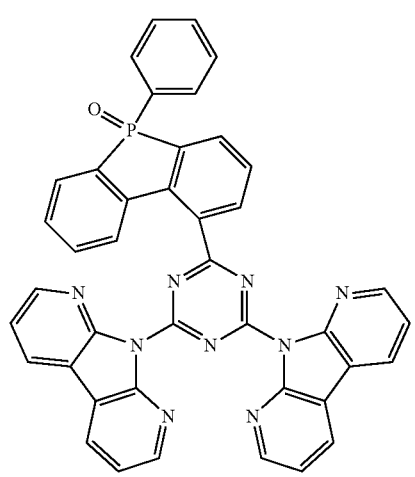
M148
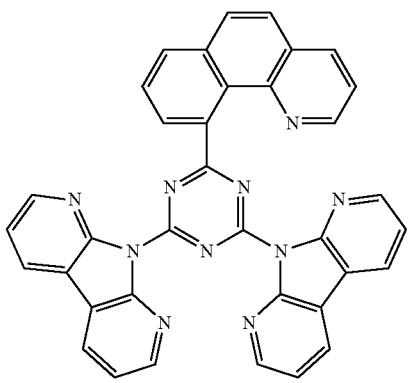
M149
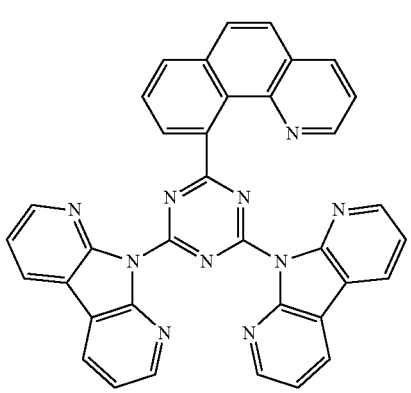
M150
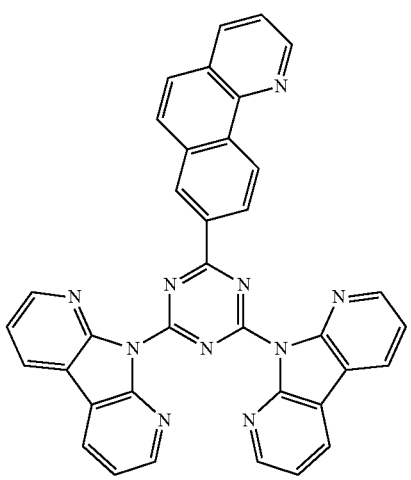

M151
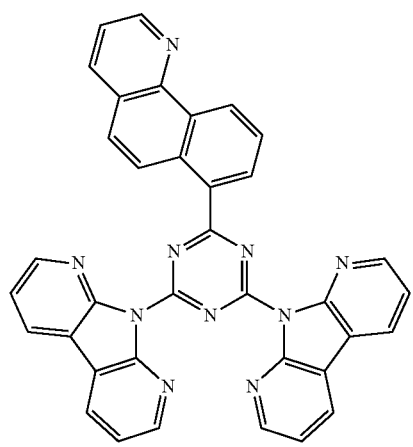
M152
M153
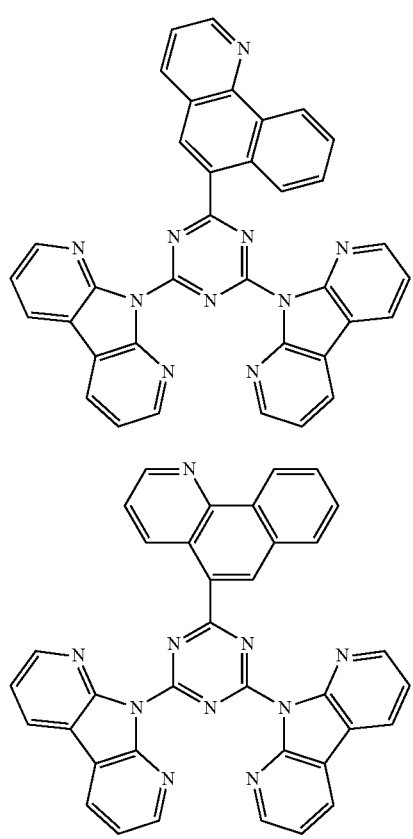
M154
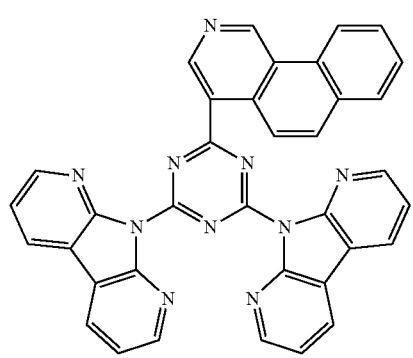
M155
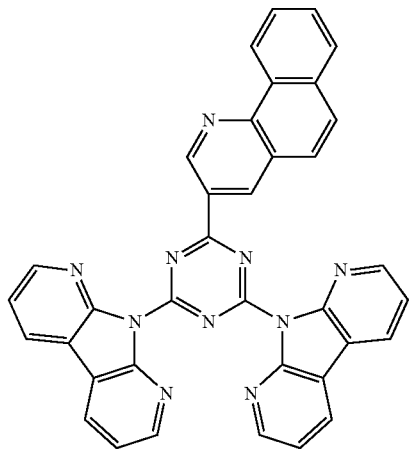
M156
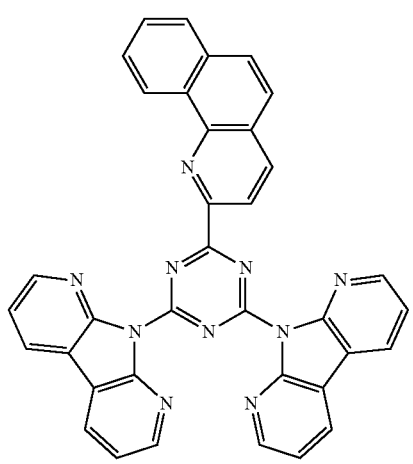
M157
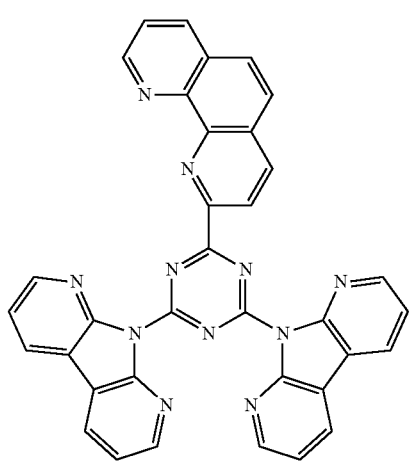

M158
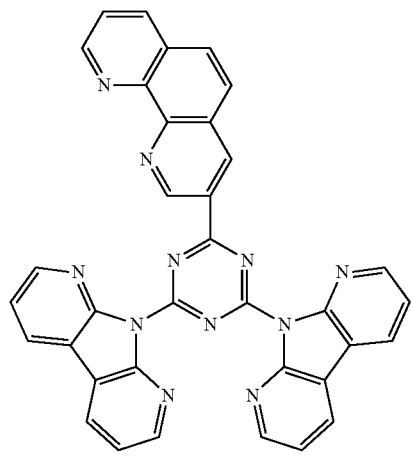
M159
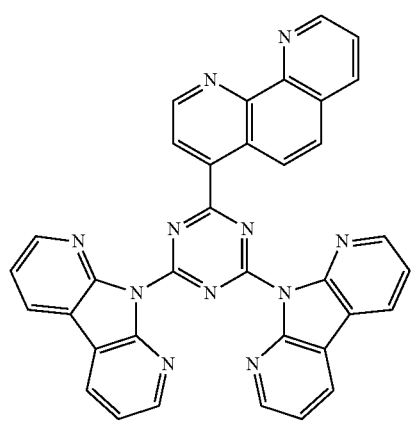
M160
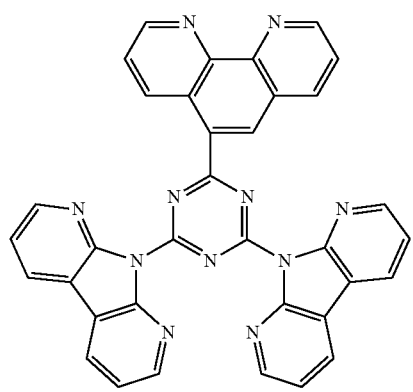
M161
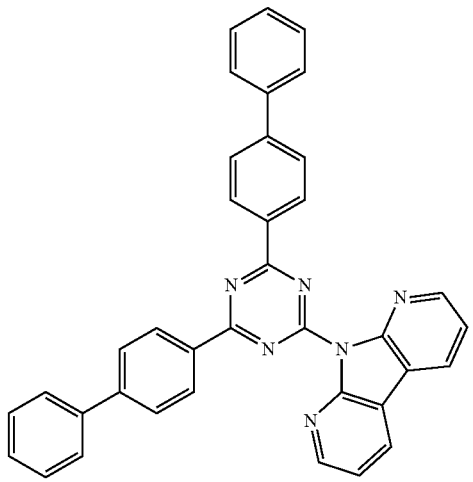
M162
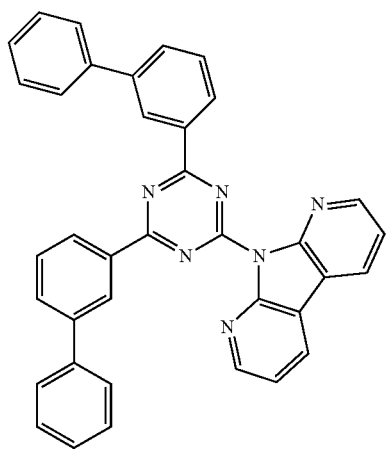
M163
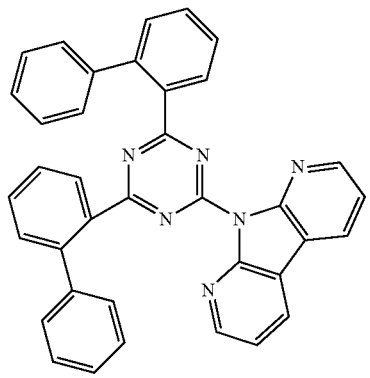

M164
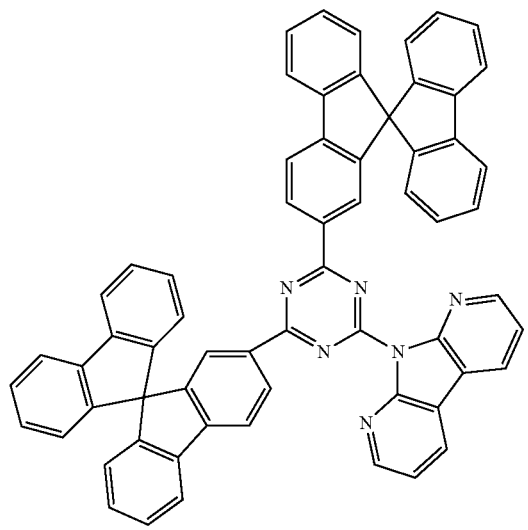
M165
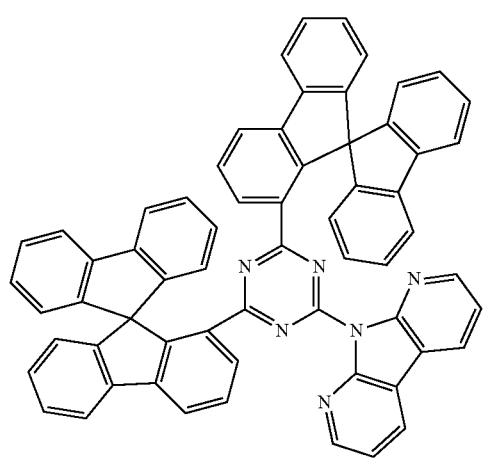
M166
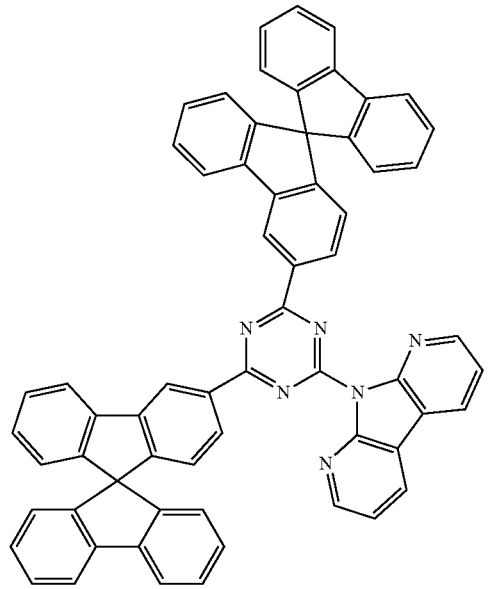
M167
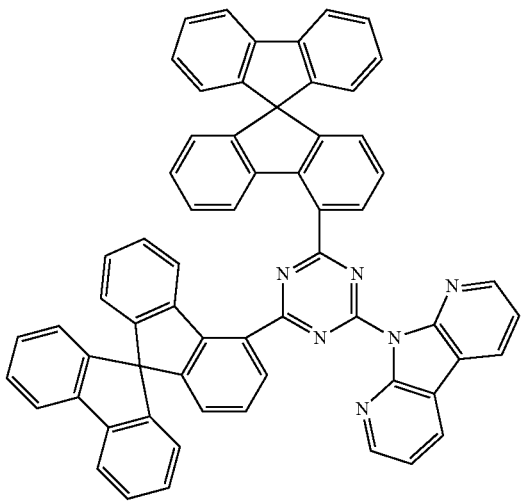
M168
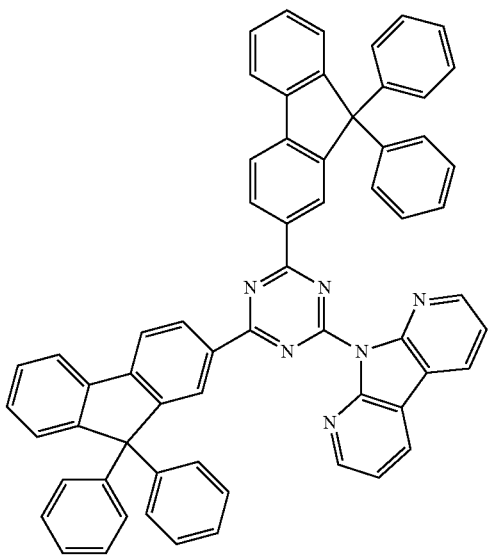
M169
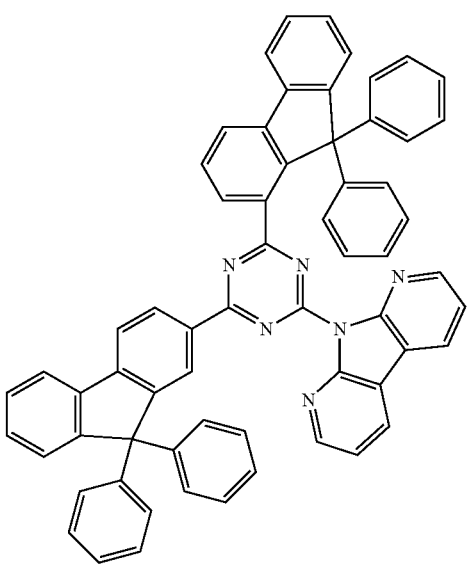

M170
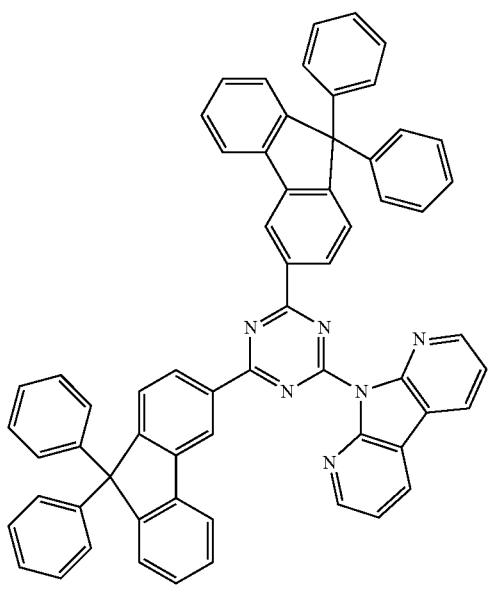
M172
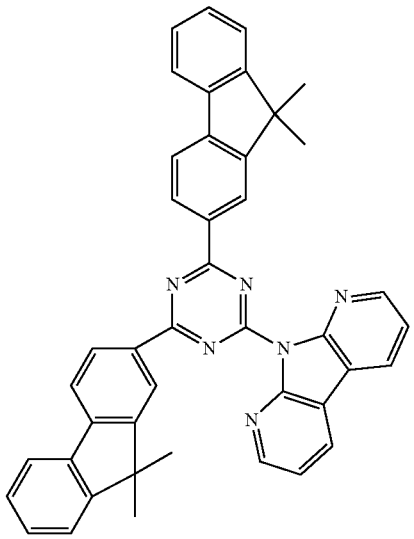
M173
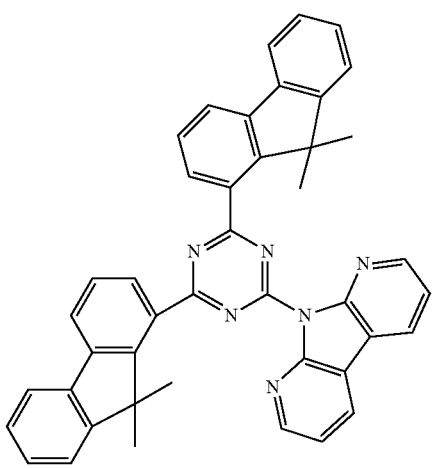
M171
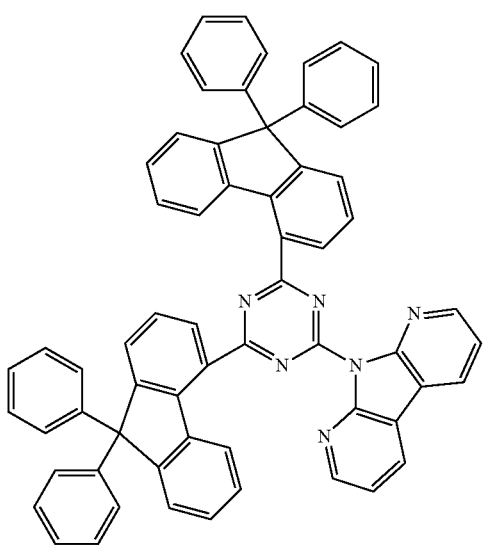
M174
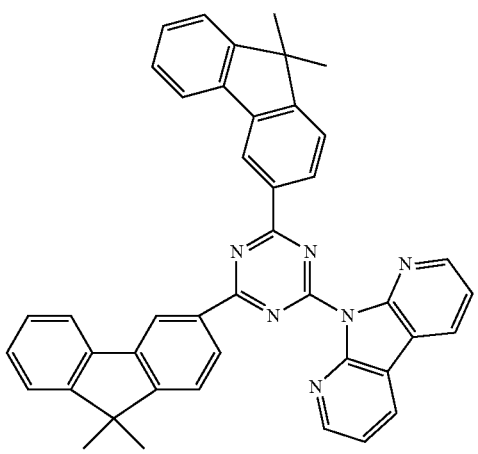

M175
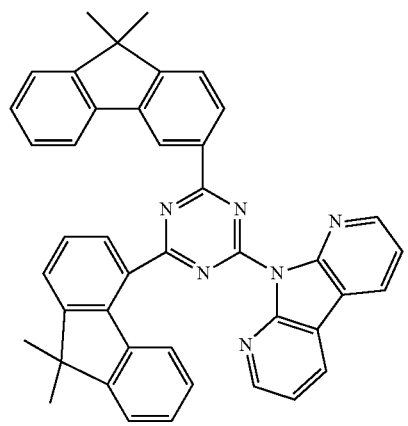
M176
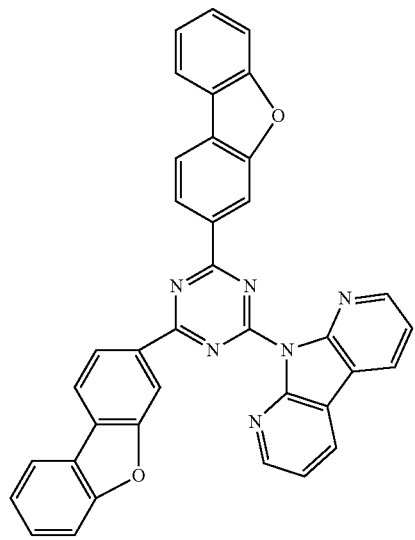
M177
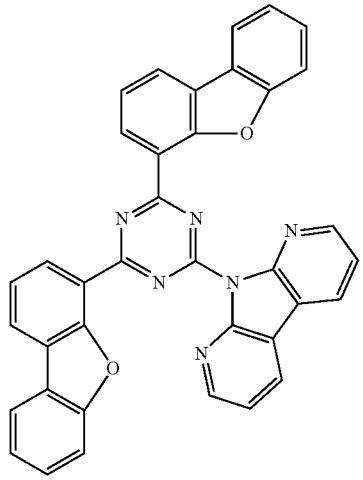
M178
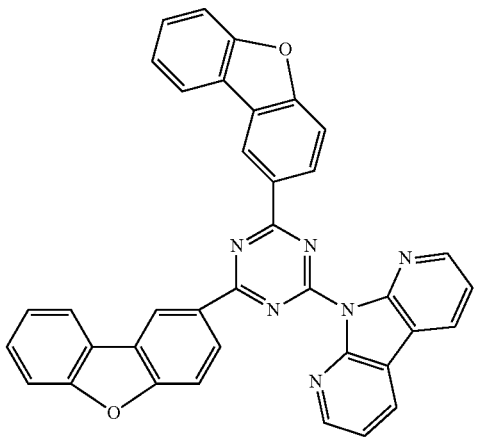
M179
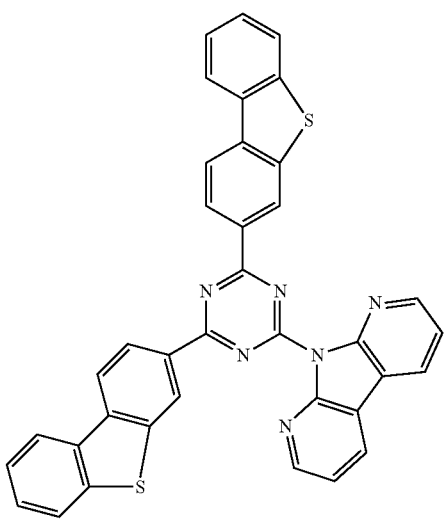
M180

M181
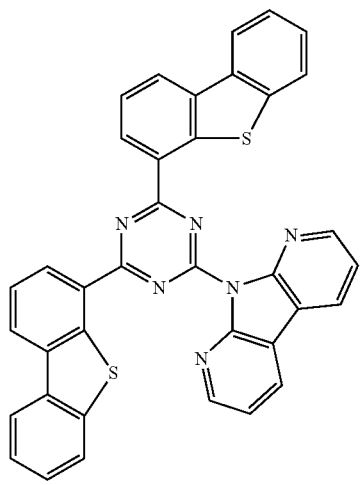
M182
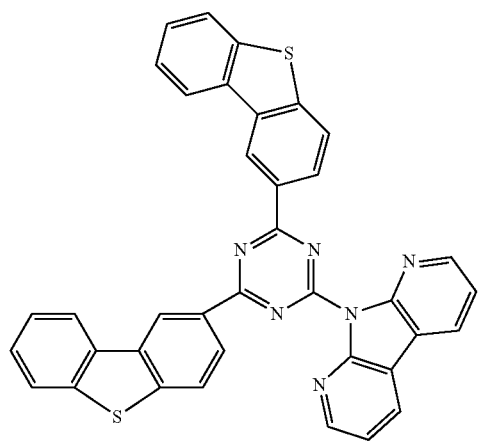
M183
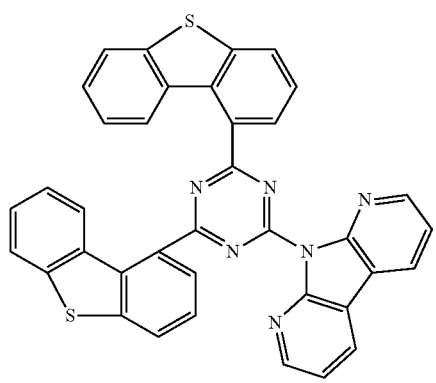
M184
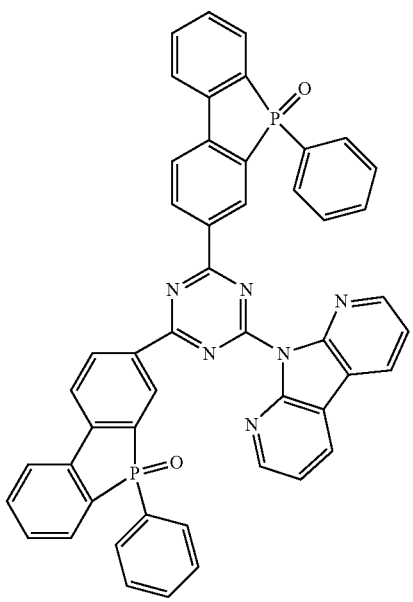
M185
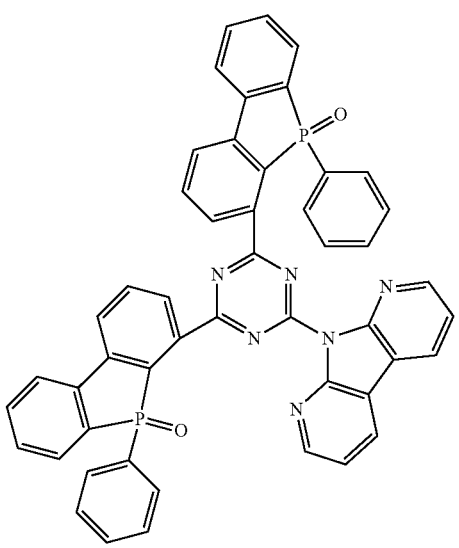

M186
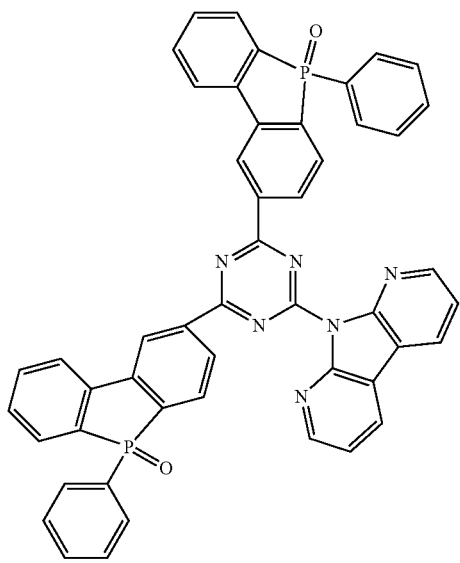
M187
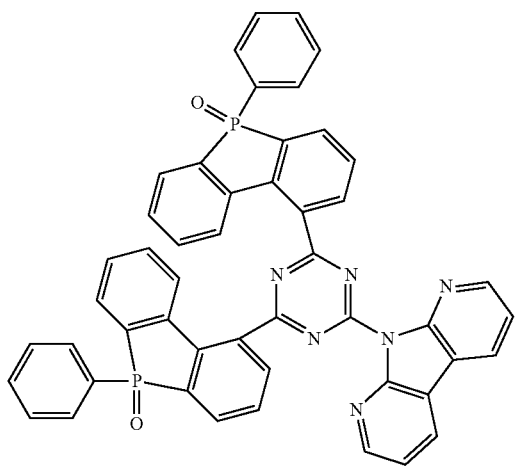
M188
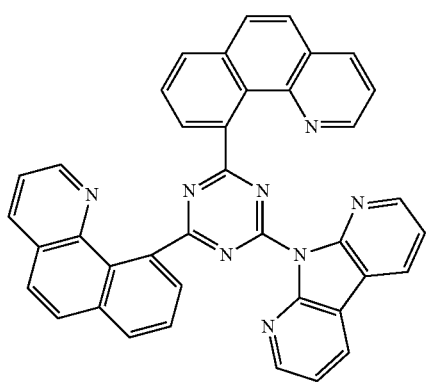
M189
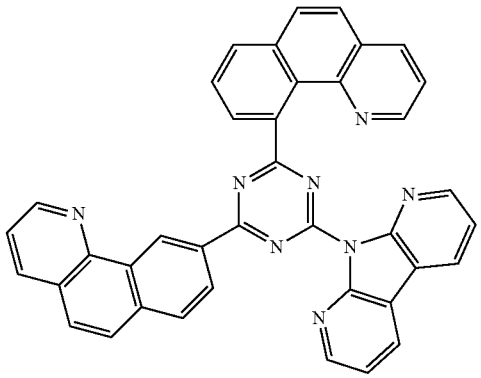
M190
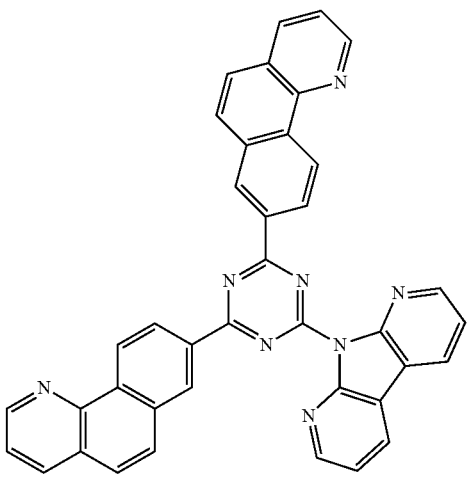
M191
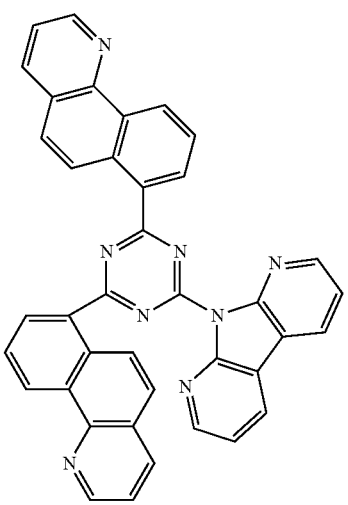

M192
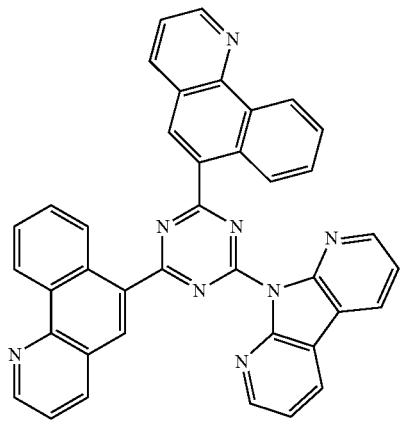
M193
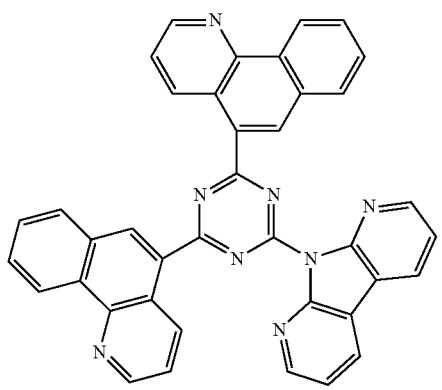
M194
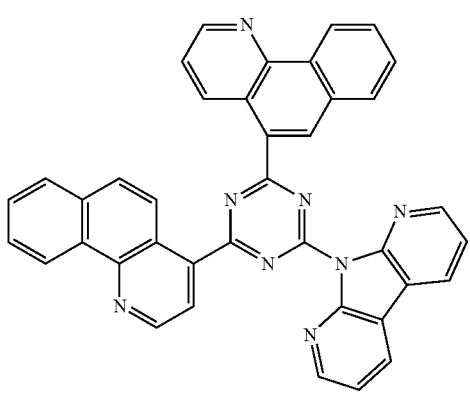
M195
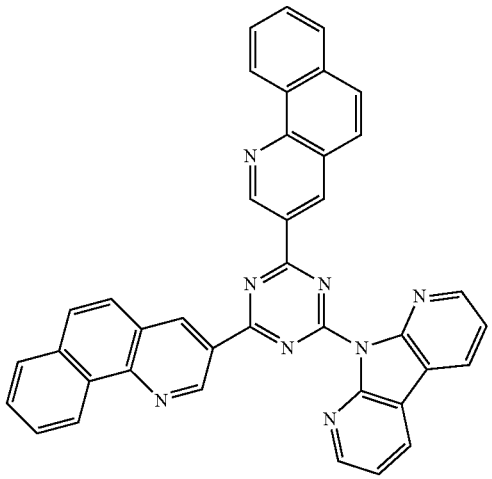
M196
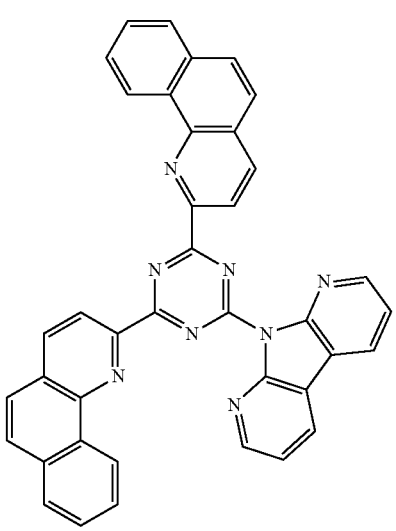
M197
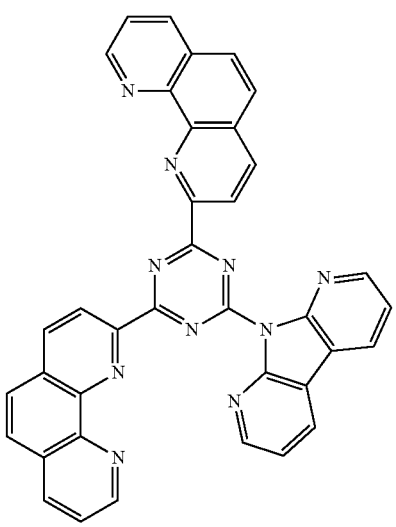

M198
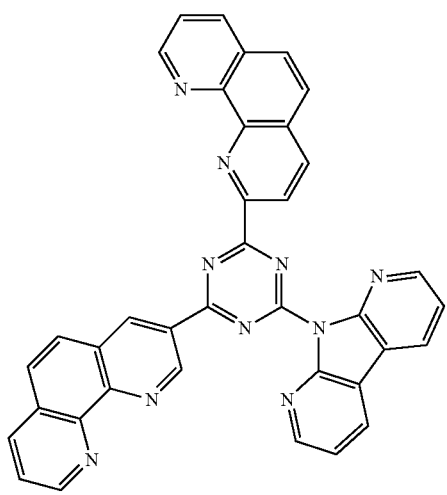
ET030M201
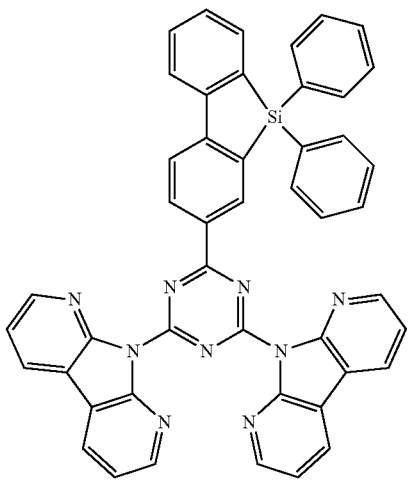
M199
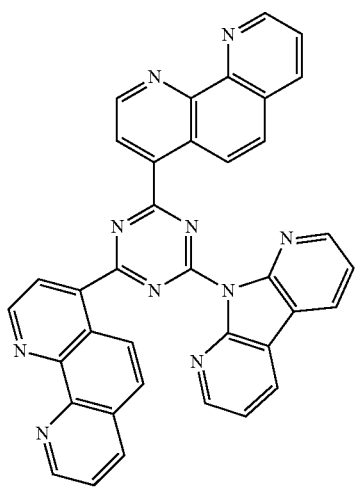
ET031M202
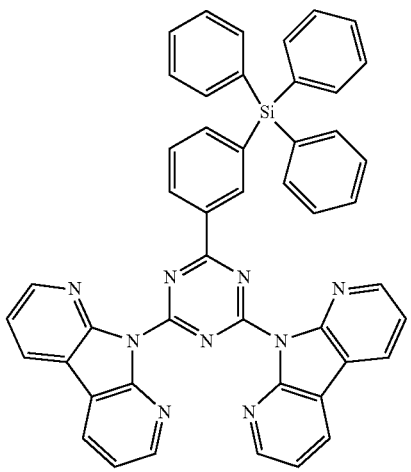
M200
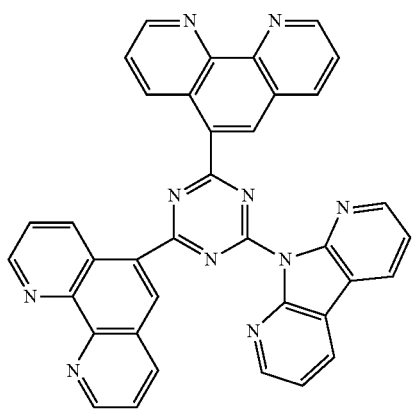
M203
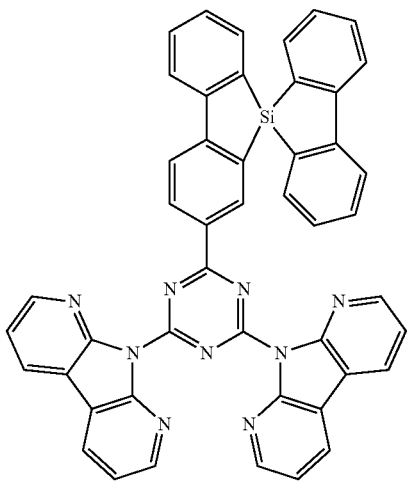

M204
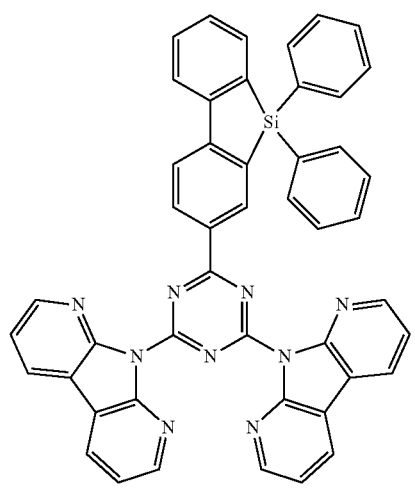
M205
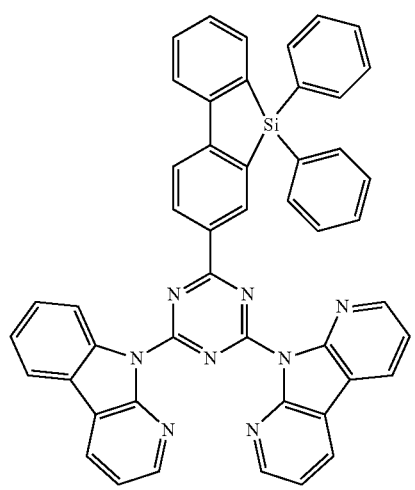
M206
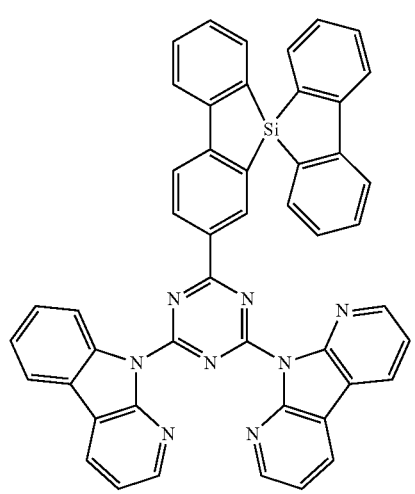
M207
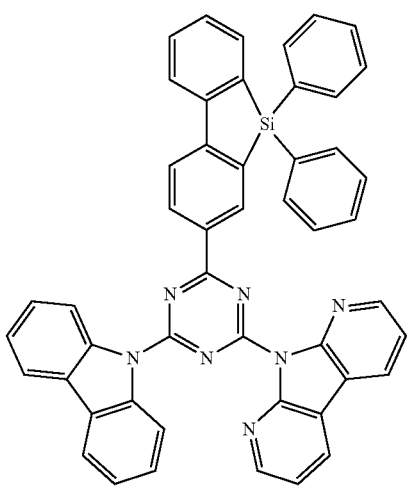
M208
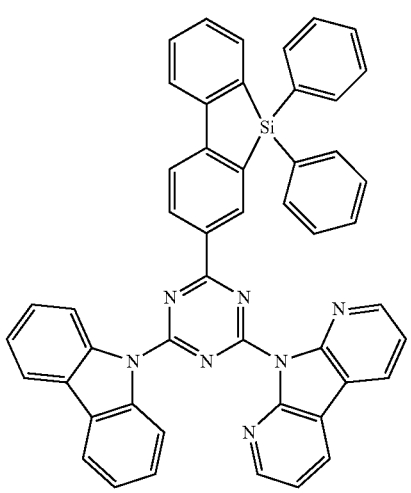
M209
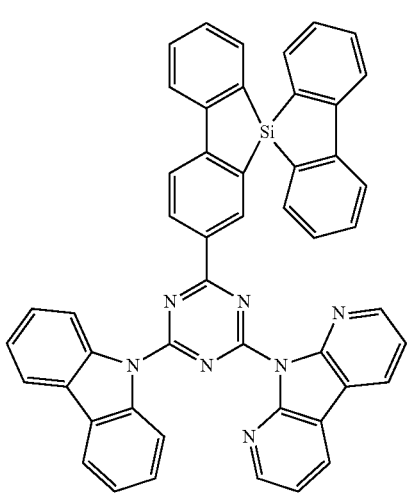

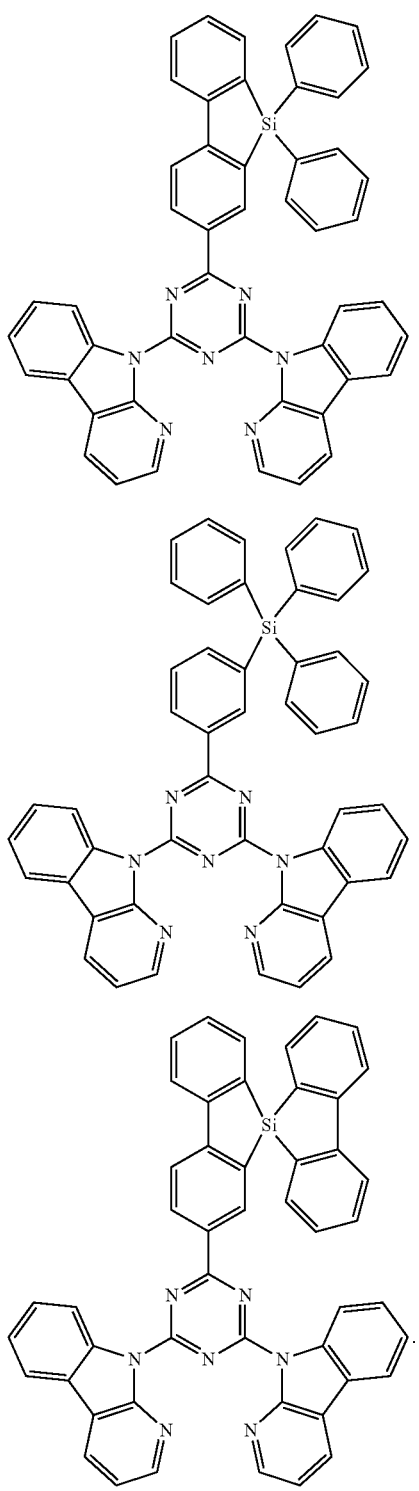

The present disclosure provides an electron transport material selected from the above-mentioned compounds which are capable of forming a tridentate or tetradentate complex structure with metal lithium, lithium organic complexes (for example, lithium 8-hydroxyquinolate), or metal Yb.

The present disclosure provides a display panel including an organic light-emitting device (OLED device), the OLED device includes an anode, a cathode disposed oppositely to the anode, and an electron transport layer and a light-emitting layer disposed between the anode and the cathode, and the electron transport layer includes the compound of the present disclosure and a dopant selected from metal lithium, lithium organic complexes (for example, lithium 8-hydroxyquinolate), or metal Yb, so that the compound of the present disclosure forms a tridentate or tetradentate complex structure with the dopant in the electron transport layer. For example, when lithium 8-quinolinolate is doped, lithium 8-quinolinolate is doped in mass ratio of 30%-70%, preferably 40%-60%, based on a total mass of the electron transport layer. In an embodiment, when lithium is doped, lithium is doped in mass ratio of 1.4%-3.4%, preferably 1.9%-2.9%, based on a total mass of the electron transport layer. When the metal Yb is doped, the metal Yb is doped in a mass ratio of 0.1%-10%, preferably 0.5%-5%, based on a total mass of the electron transport layer.

In an embodiment of the display panel according to the present disclosure, the OLED device further includes a hole blocking layer, and the hole blocking layer is made of a material including the compound of the present disclosure.

In an embodiment of the display panel according to the present disclosure, the OLED device further includes a first lamination layer and a second lamination layer disposed between the anode and the cathode and spaced apart from each other, and a charge generation layer (CGL) disposed between the first lamination layer and the second lamination layer and containing the compound of the present disclosure and a dopant selected from metal lithium, lithium organic complexes (for example, Liq and lithium 8-hydroxyquinolate), or metal Yb, so that the compound of the present disclosure forms a tridentate or tetradentate complex structure with the dopant in the charge generation layer (CGL). Each of the first lamination layer and the second lamination layer includes a light-emitting layer, the light-emitting layer of the first lamination layer includes a first light-emitting layer formed between the anode and the charge generation layer, and the light-emitting layer of the second lamination layer includes a second light-emitting layer formed between the cathode and the charge generation layer. For example, when lithium 8-quinolinolate is doped, in an embodiment, lithium 8-quinolinolate is doped in mass ratio of 30%-70%, preferably 40%-60%, based on a total mass of the charge generation layer. When lithium is doped, in an embodiment, lithium is doped in mass ratio of 1.4%-3.4%, preferably 1.9%-2.9%, based on a total mass of the charge generation layer. When the metal Yb is doped, in an embodiment, the metal Yb is doped in a mass ratio of 0.1%-10%, preferably 0.5%-5%, based on a total mass of the charge generation layer.

In an embodiment of the display panel according to the present disclosure, the first light-emitting layer and the second light-emitting layer each are independently a mono-color light-emitting layer or a composite light-emitting layer formed by stacking a plurality of mono-color light-emitting layers, the mono-color light-emitting layer is a red light-emitting layer, a green light-emitting layer, a blue light-emitting layer, or a yellow light-emitting layer, and each mono-color light-emitting layer of the plurality of mono-color light-emitting layers is independently a red light-emitting layer, a green light-emitting layer, a blue light-emitting layer, or a yellow light-emitting layer.

In an embodiment of the display panel according to the present disclosure, the first light-emitting layer and the second light-emitting layer are independently selected from a fluorescent light-emitting layer or a phosphorescent light-emitting layer.

In an embodiment of the display panel according to the present disclosure, the organic light-emitting device further includes one or more of a hole injection layer, a hole blocking layer, an electron injection layer, or an electron blocking layer. Materials used in these functional layers are not particularly limited, which can be selected according to actual conditions.

The present disclosure further exemplarily describes synthesis of compounds M004, M037, M056, M104 and M157.

Example 1

Synthesis of Compound M004

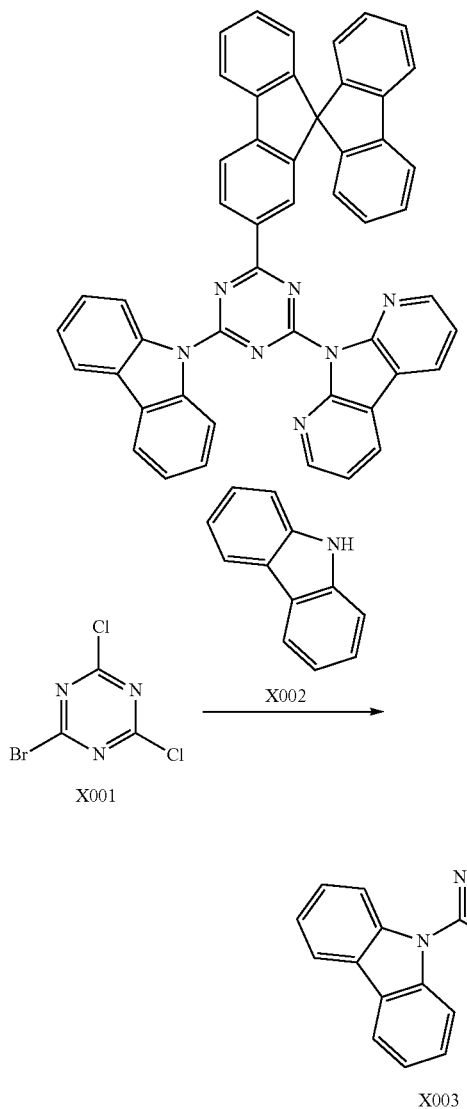

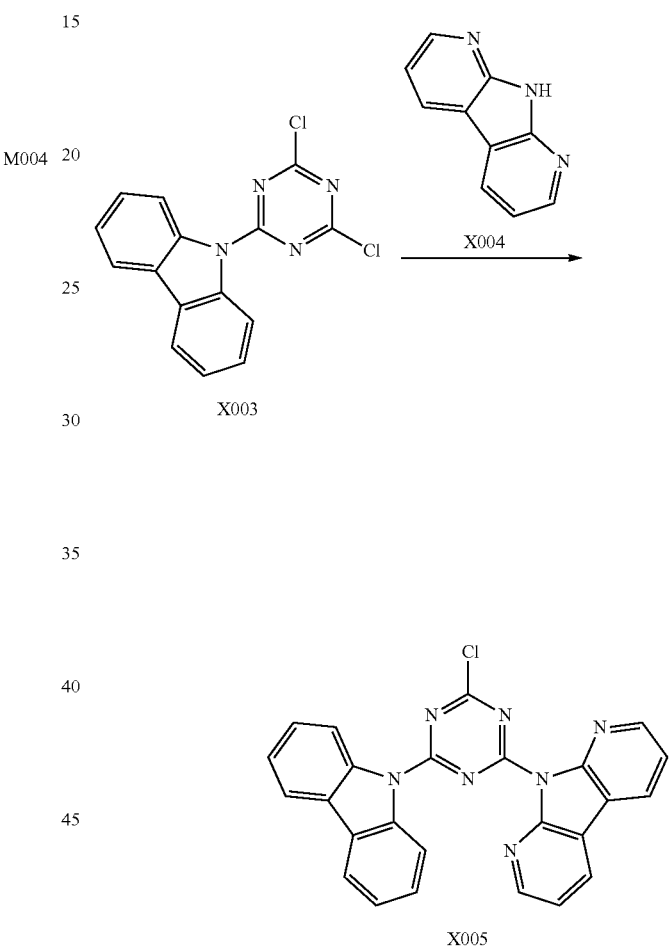

At room temperature and under a nitrogen atmosphere, X002 (1.15 mmol) was dissolved in 40 mL of anhydrous tetrahydrofuran (THF). NaH (1.4 mmol), after repeatedly washed with n-hexane, was added to the above solution. After stirring for 1 h, X001 (1.1 mmol) was added and stirred overnight at room temperature. The reaction was quenched by adding methanol and water and was extracted with dichloromethane. The organic phase was collected and dried over anhydrous $Na_2SO_4$. The dried solution was filtered, and the solvent was removed by using a rotary evaporator to obtain a crude product. The crude product was purified by silica gel chromatography using chloroform/n-hexane as eluent to obtain intermediate X003 (0.94 mmol, yield 85%).

MALDI-TOF MS: $C_{15}H_8Cl_2N_4$: m/z calculated: 314.0; measured: 314.2.

At room temperature and under a nitrogen atmosphere, X004 (1.15 mmol) was dissolved in 45 mL of anhydrous THF. NaH (1.5 mmol), after repeatedly washed with n-hexane, was added to the above solution. After stirring for 1 h, X003 (1.0 mmol) was added and stirred overnight at room temperature. The reaction was quenched by adding methanol and water and was extracted with dichloromethane. The organic phase was collected and dried over anhydrous $Na_2SO_4$. The dried solution was filtered, and the solvent was removed by using a rotary evaporator to obtain a crude product. The crude product was purified by silica gel chromatography using chloroform/n-hexane as eluent to obtain intermediate X005 (0.78 mmol, yield 78%).

MALDI-TOF MS: $C_{25}H_{14}ClN_7$: m/z calculated: 447.1; measured: 447.2.

81

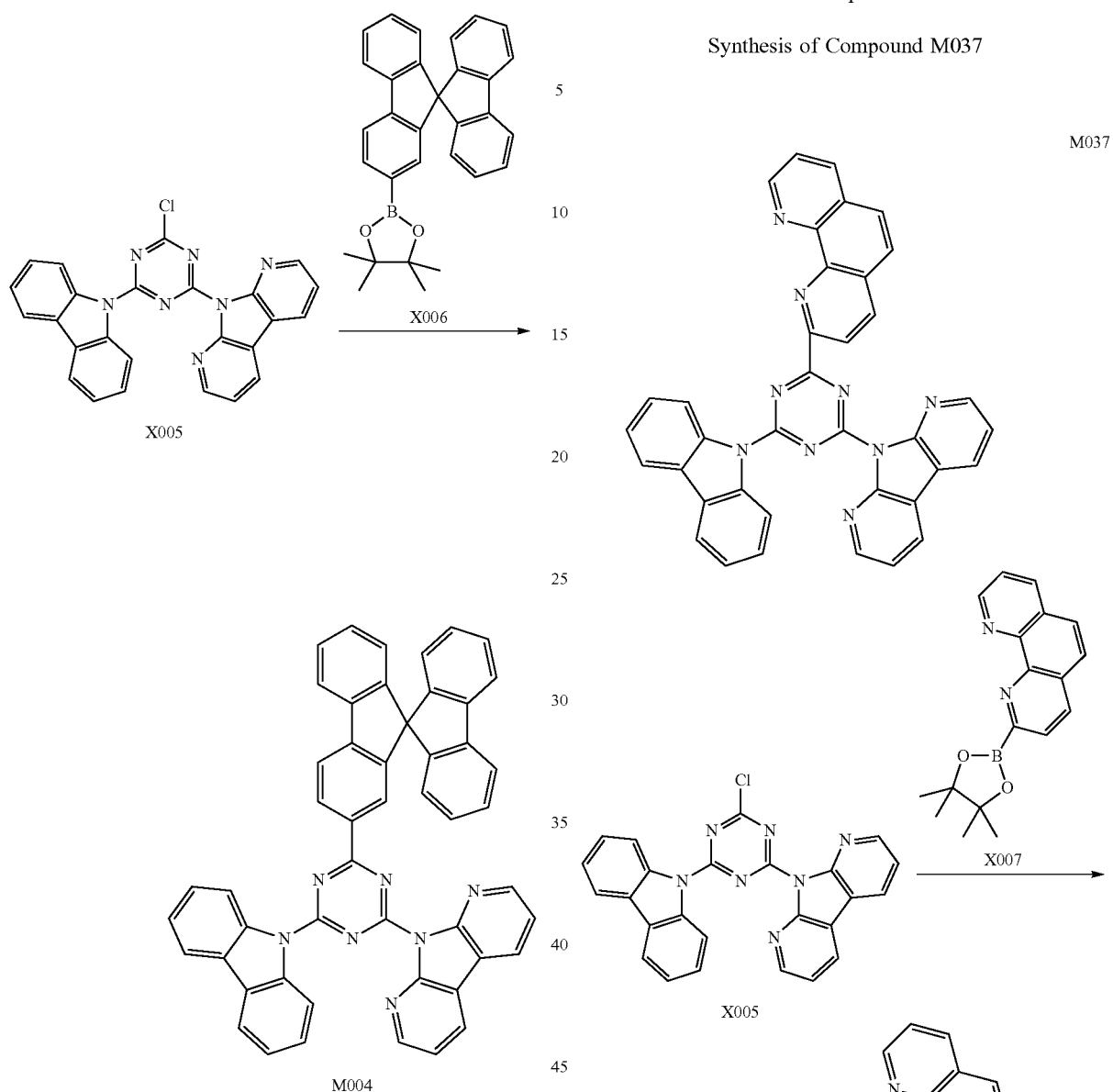

Under the protection of nitrogen, X005 (1 mmol) and X006 (1.15 mmol) were dissolved in 45 mL of toluene, Pd(PPh$_3$)$_4$ (0.05 mmol) was added as a catalyst, 4 mL of aqueous solution of potassium carbonate (2 mol/L) was add, and the mixture was refluxed for 12 h. After the reaction was finished, the reaction mixture was extracted three times with saturated brine and ethyl acetate, and the organic phases were combined and dried over anhydrous sodium sulfate. All the solvents were removed by distillation under reduced pressure, and the crude product was collected. The crude product was purified through a silica gel chromatography column, using a mixed solvent of n-hexane and chloroform with a volume ratio of 5:1 as eluent to finally obtain a solid M004 (0.88 mmol, yield 88%).

MALDI-TOF MS: C$_{50}$H$_{29}$N$_7$: m/z calculated: 727.2; measured: 727.3.

Elemental analysis, calculated: C, 82.51; H, 4.02; N, 13.47; measured: C, 82.56; H, 4.00; N, 13.44.

82

Example 2

Synthesis of Compound M037

Under the protection of nitrogen, compounds X005 (1.3 mmol), X007 (1.45 mmol), [Pd$_2$(dba)$_3$]CHCl$_3$ (0.06 mmol) and HP(tBu)$_3$·BF$_4$ (0.12 mmol) were weighed and added to a 250 mL two-necked flask. 60 mL of toluene (N$_2$ was introduced into the toluene for 15 min in advance to remove oxygen) was injected into the two-necked flask, and then 6 mL of 1M $K_2CO_3$ aqueous solution ($N_2$ was introduced into the $K_2CO_3$ aqueous solution for 15 min in advance to remove oxygen) was added dropwise and stirred overnight at room temperature. After the reaction was finished, 20 mL of deionized water was added, and a few drops of 2M HCl were added. The resulting mixture was extracted with dichloromethane. The organic phase was collected and dried over anhydrous $Na_2SO_4$. The dried solution was filtered, and the solvent was removed by using a rotary evaporator to obtain a crude product. The crude product was purified by silica gel chromatography to finally obtain a solid M037 (1.03 mmol, 79%).

MALDI-TOF MS: $C_{37}H_{21}N_9$: m/z calculated: 591.2; measured: 591.4.

Elemental analysis, calculated: C, 75.11; H, 3.58; N, 21.31; measured: C, 75.15; H, 3.56; N, 21.29.

Example 3

Synthesis of Compound M056

Under the protection of nitrogen, compounds X001 (2.0 mmol), X008 (2.3 mmol), $[Pd_2(dba)_3]CHCl_3$ (0.08 mmol) and $HP(tBu)_3 \cdot BF_4$ (0.16 mmol) were weighed and added to a 250 mL two-necked flask. Into the two-necked flask was injected 100 mL of toluene ($N_2$ was introduced into the toluene for 15 min in advance to remove oxygen), and then 8 mL of 1M $K_2CO_3$ aqueous solution ($N_2$ was introduced into the $K_2CO_3$ aqueous solution for 15 min in advance to remove oxygen) was added dropwise and stirred overnight at room temperature. After the reaction was finished, 35 mL of deionized water was added, and a few drops of 2M HCl were added. The resulting mixture was extracted with dichloromethane. The organic phase was collected and dried over anhydrous $Na_2SO_4$. The dried solution was filtered, and the solvent was removed by using a rotary evaporator to obtain a crude product. The crude product was purified by silica gel chromatography to finally obtain a solid X009 (1.66 mmol, 83%).

MALDI-TOF MS: $C_{15}H_7Cl_2N_3O$: m/z calculated: 315.0; measured: 315.2.

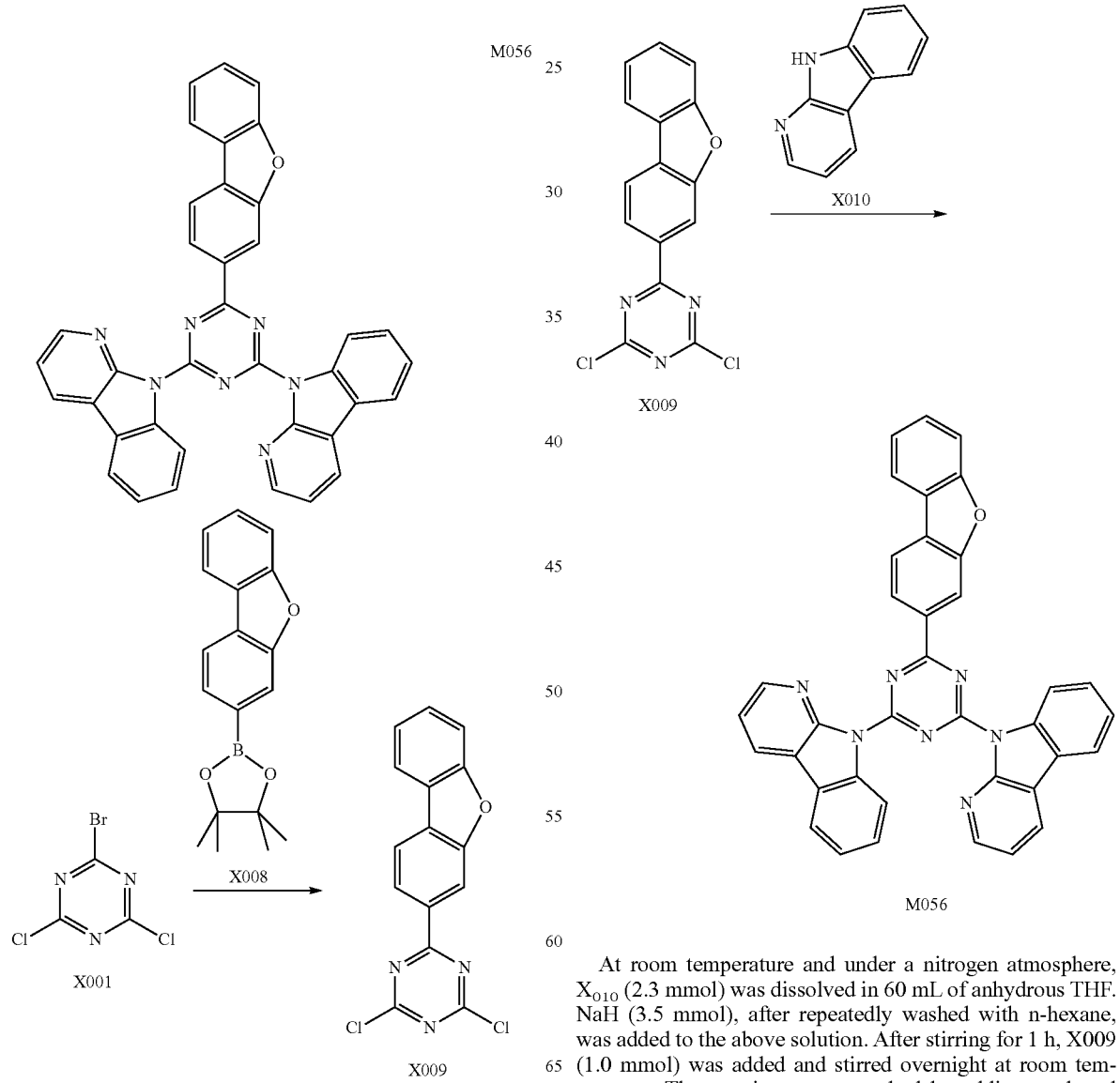

At room temperature and under a nitrogen atmosphere, $X_{010}$ (2.3 mmol) was dissolved in 60 mL of anhydrous THF. NaH (3.5 mmol), after repeatedly washed with n-hexane, was added to the above solution. After stirring for 1 h, X009 (1.0 mmol) was added and stirred overnight at room temperature. The reaction was quenched by adding methanol and water and was extracted with dichloromethane. The organic phase was collected and dried over anhydrous Na$_2$SO$_4$. The dried solution was filtered, and the solvent was removed by using a rotary evaporator to obtain a crude product. The crude product was purified by silica gel chromatography using chloroform/n-hexane as eluent to obtain target compound M056 (0.71 mmol, yield 71%).

MS-TOF MALDI: C$_{37}$H$_{21}$N$_7$O: m/z calculated: 579.2; measured: 579.4.

Elemental analysis, calculated: C, 76.67; H, 3.65; N, 16.92; O, 2.76; measured: C, 76.70; H, 3.67; N, 16.89; O, 2.74.

Example 4

Synthesis of Compound M104

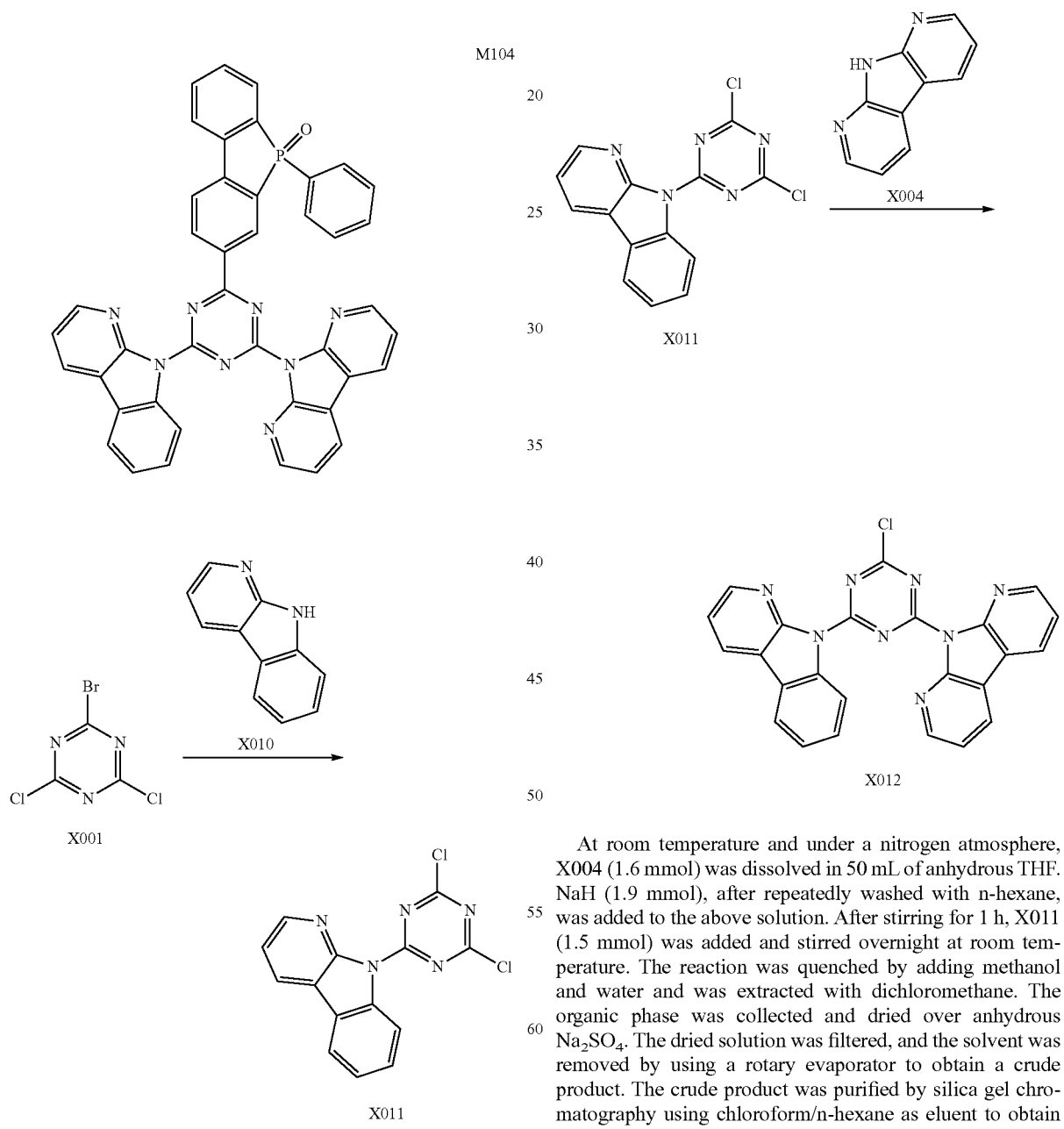

At room temperature and under a nitrogen atmosphere, X010 (1.05 mmol) was dissolved in 40 mL of anhydrous THF. NaH (1.3 mmol), after repeatedly washed with n-hexane, was added to the above solution. After stirring for 1 h, X001 (1.0 mmol) was added and stirred overnight at room temperature. The reaction was quenched by adding methanol and water and was extracted with dichloromethane. The organic phase was collected and dried over anhydrous Na$_2$SO$_4$. The dried solution was filtered, and the solvent was removed by using a rotary evaporator to obtain a crude product. The crude product was purified by silica gel chromatography using chloroform/n-hexane as eluent to obtain intermediate X011 (0.81 mmol, yield 81%).

MALDI-TOF MS: C$_{14}$H$_7$Cl$_2$N$_5$: m/z calculated: 315.0; measured: 315.3.

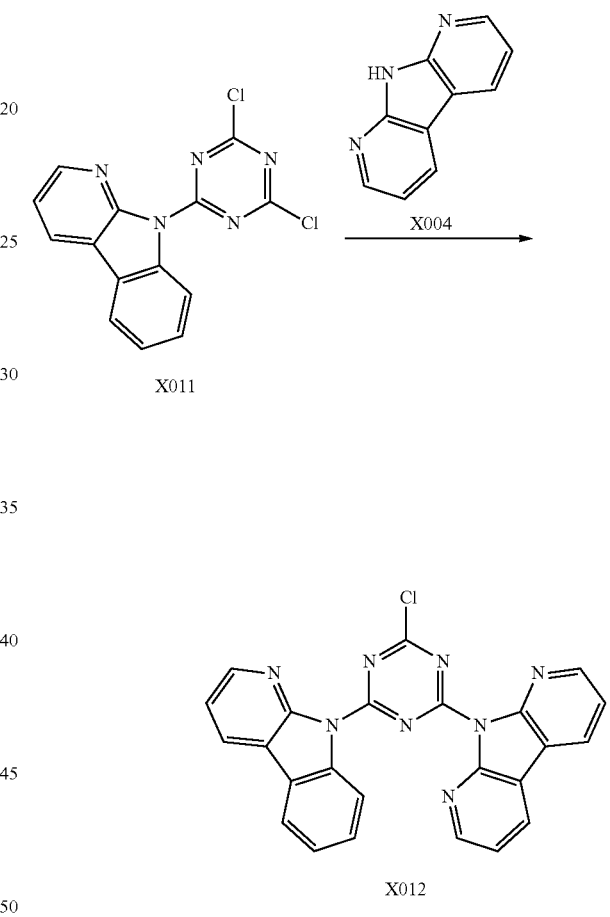

At room temperature and under a nitrogen atmosphere, X004 (1.6 mmol) was dissolved in 50 mL of anhydrous THF. NaH (1.9 mmol), after repeatedly washed with n-hexane, was added to the above solution. After stirring for 1 h, X011 (1.5 mmol) was added and stirred overnight at room temperature. The reaction was quenched by adding methanol and water and was extracted with dichloromethane. The organic phase was collected and dried over anhydrous Na$_2$SO$_4$. The dried solution was filtered, and the solvent was removed by using a rotary evaporator to obtain a crude product. The crude product was purified by silica gel chromatography using chloroform/n-hexane as eluent to obtain intermediate X012 (1.1 mmol, yield 73%).

MALDI-TOF MS: C$_{24}$H$_{13}$ClN$_8$: m/z calculated: 448.1; measured: 448.3.

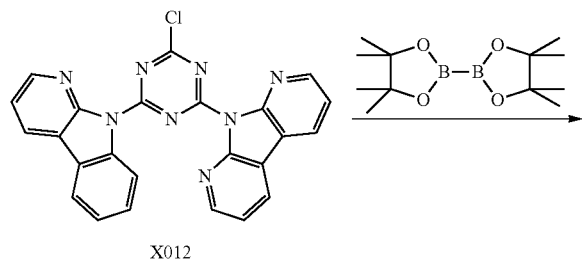

X012

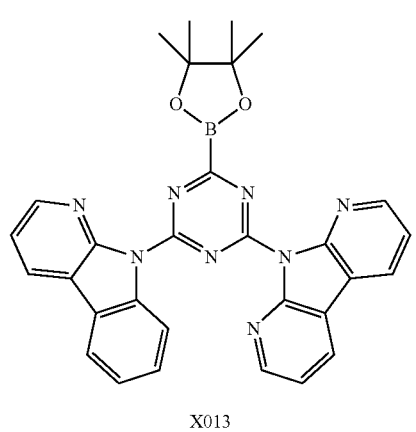

X013

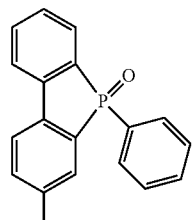

X014

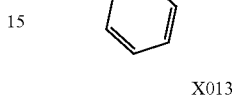

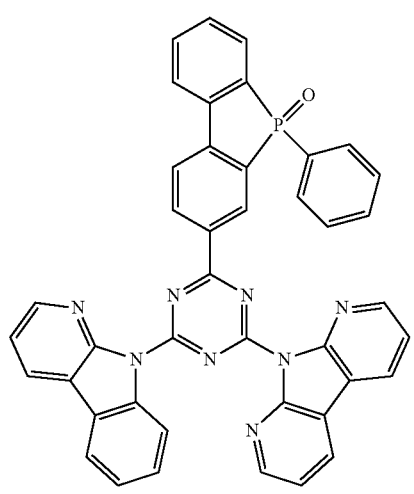

M104

X012 (2.5 mmol), bis(pinacolato)diboron (2.7 mmol), (1,1'-bis(diphenylphosphino) ferrocene) dichloropalladium (II) (0.08 mmol) and potassium acetate (7.0 mmol) were added separately into a 100 mL three-necked flask, the resulting mixture was quickly degased and replaced with nitrogen while stirring for 3 times, and then 30.0 mL of tetrahydrofuran was added via a syringe. The mixture was stirred at a certain speed, and the resulting mixed solution of reactants was heated at a reaction temperature of 80° C. and refluxed for 5 h. After the reaction was finished, the reaction mixture was cooled to room temperature, added with 25 mL of water, and extracted with ethyl ether. The resulting organic phase was dried over anhydrous sodium sulfate, the solvent was removed by distillation. Column chromatography was used for purification to obtain intermediate X013 (1.9 mmol, 76%).

MALDI-TOF MS: m/z calculated: $C_{30}H_{25}BN_8O_2$: 540.2; measured: 540.5.

Under the protection of nitrogen, compounds X013 (2.0 mmol), X014 (2.2 mmol), [$Pd_2(dba)_3$]$CHCl_3$ (0.08 mmol) and HP(tBu)$_3\cdot$BF$_4$ (0.16 mmol) were weighed and added to a 250 mL two-necked flask. 70 mL of toluene ($N_2$ was introduced into the toluene for 15 min in advance to remove oxygen) was injected into the two-necked flask, and then 6.5 mL of 1M $K_2CO_3$ aqueous solution ($N_2$ was introduced into the $K_2CO_3$ aqueous solution for 15 min in advance to remove oxygen) was added dropwise and stirred overnight at room temperature. After the reaction was finished, 30 mL of deionized water was added, and a few drops of 2M HCl were dripped. The resulting mixture was extracted with dichloromethane. The organic phase was collected and dried over anhydrous $Na_2SO_4$. The dried solution was filtered, and the solvent was removed by using a rotary evaporator to obtain a crude product. The crude product was purified by silica gel chromatography to finally obtain a solid M104 (1.3 mmol, 65%).

MALDI-TOF MS: $C_{42}H_{25}N_8OP$: m/z calculated: 688.2; measured: 688.4.

Elemental analysis, calculated: C, 73.25; H, 3.66; N, 16.27; O, 2.32; measured: C, 73.24; H, 3.67; N, 16.26; O, 2.34.

Example 5

Synthesis of Compound 157

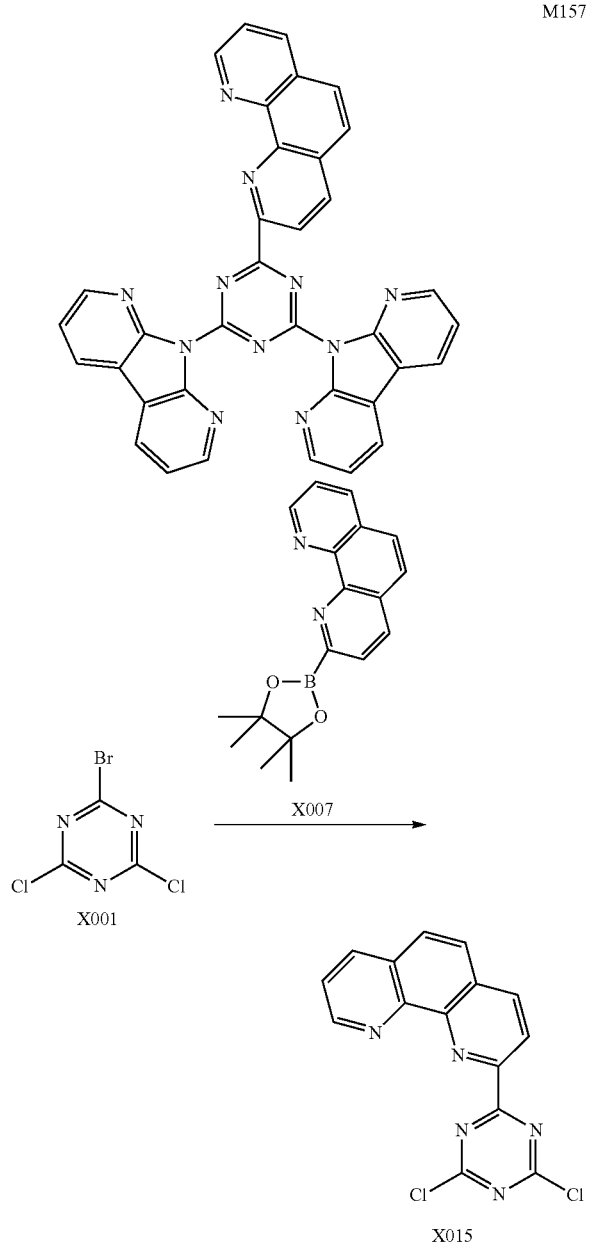

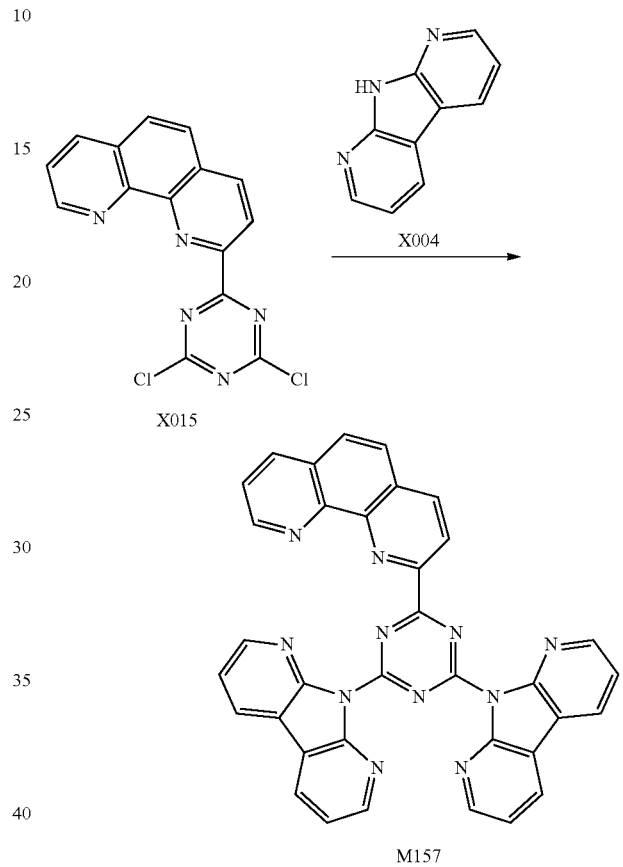

Under the protection of nitrogen, compounds X001 (1.0 mmol), X007 (1.1 mmol), [Pd$_2$(dba)$_3$]CHCl$_3$ (0.05 mmol) and HP(tBu)$_3$·BF$_4$ (0.10 mmol) were weighed and added to a 100 mL two-necked flask. 30 mL of toluene (N$_2$ was introduced into the toluene for 15 min in advance to remove oxygen) was injected into the two-necked flask, and then 3 mL of 1M K$_2$CO$_3$ aqueous solution (N$_2$ was introduced into the aqueous solution of K$_2$CO$_3$ for 15 min in advance to remove oxygen) was added dropwise and stirred overnight at room temperature. After the reaction was finished, 15 mL of deionized water was added, and then a few drops of 2M HCl were added. The resulting mixture was extracted with dichloromethane. The organic phase was collected and dried over anhydrous Na$_2$SO$_4$. The dried solution was filtered, and the solvent was removed by using a rotary evaporator to obtain a crude product. The crude product was purified by silica gel chromatography to finally obtain a solid of X015 (0.72 mmol, 72%).

MALDI-TOF MS: C$_{15}$H$_7$Cl$_2$N$_5$: m/z calculated: 327.0; measured: 327.2.

At room temperature and under a nitrogen atmosphere, X004 (2.3 mmol) was dissolved in 60 mL of anhydrous THF. NaH (3.5 mmol), after repeatedly washed with n-hexane, was added to the above solution. After stirring for 1 h, X015 (1.0 mmol) was added and stirred overnight at room temperature. The reaction was quenched by adding methanol and water and was extracted with dichloromethane. The organic phase was collected and dried over anhydrous Na$_2$SO$_4$. The dried solution was filtered, and the solvent was removed by using a rotary evaporator to obtain a crude product. The crude product was purified by silica gel chromatography using chloroform/n-hexane as eluent to obtain target compound M157 (0.60 mmol, yield 60%).

MALDI-TOF MS: C$_{35}$H$_{19}$N$_{11}$: m/z calculated: 593.2; measured: 593.4.

Elemental analysis, calculated: C, 70.82; H, 3.23; N, 25.96; measured: C, 70.88; H, 3.20; N, 25.93.

Simulation and calculation of energy levels of compounds:

With respect to some of the exemplary organic compounds provided in the present disclosure and the comparative compounds, the distributions of the molecular frontier orbitals of HOMO and LUMO were optimized and calculated by applying a density functional theory (DFT) and using a Gaussian 09 software package (Gaussian Inc.) with B3LYP/6-31G(d) calculation level. Meanwhile, based on time-dependent density functional theory (TDDFT), the lowest triplet energy level En of the molecules of the compounds was simulated and calculated. The results are shown in the following Table 1.

TABLE 1

| Compound | HOMO (eV) | LUMO (eV) | Eg (eV) | $E_{T1}$ (eV) |
|---|---|---|---|---|
| M004 | −5.64 | −1.77 | 3.87 | 2.67 |
| M016 | −5.65 | −1.87 | 3.78 | 2.81 |
| M020 | −5.66 | −1.90 | 3.76 | 2.80 |
| M037 | −5.50 | −2.05 | 3.45 | 2.65 |
| M044 | −5.71 | −1.77 | 3.94 | 2.67 |
| M056 | −5.89 | −1.85 | 4.04 | 2.81 |
| M104 | −5.88 | −2.05 | 3.83 | 2.64 |
| M124 | −5.60 | −1.67 | 3.93 | 2.66 |
| M128 | −5.74 | −1.70 | 4.04 | 2.65 |
| M136 | −5.95 | −1.76 | 4.19 | 2.79 |
| M140 | −5.78 | −1.78 | 4.00 | 2.78 |
| M144 | −6.12 | −1.96 | 4.16 | 2.64 |
| M157 | −6.04 | −1.95 | 4.09 | 2.64 |
| M201 | −5.80 | −1.73 | 4.07 | 2.61 |
| M202 | −6.19 | −1.59 | 4.60 | 3.14 |
| Comparative compound 1 | −5.98 | −1.47 | 4.51 | 2.72 |
| Comparative compound 2 | −5.73 | −1.90 | 3.83 | 2.68 |

Device Example 1

This example provides an organic light-emitting device (OLED device). The OLED device includes in sequence a substrate 1, an ITO anode 2, a hole injection layer 3, a first hole transport layer 4, a second hole transport layer 5, a light-emitting layer 6, a first electron transport layer 7, a second electron transport layer 8, and a cathode (silver electrode) 9.

The OLED device was manufactured by the following specific steps.

(1) A glass substrate 1 was cut into a size of 50 mm×50 mm×0.7 mm, ultrasonically treated respectively in acetone, isopropanol and deionized water for 30 min, and then cleaned in ozone for 10 min; and the obtained glass substrate with an ITO anode layer 2 was mounted on a vacuum deposition apparatus.

(2) Under a vacuum degree of 2×10$^{-6}$ Pa, compound A used as a hole injection material was vacuum-evaporated onto the ITO anode 2 to form a hole injection layer 3 having a thickness of 5 nm.

(3) Compound B was vacuum-evaporated on the hole injection layer 3 to form a first hole transport layer 4 having a thickness of 90 nm.

(4) Compound C was vacuum-evaporated on the first hole transport layer 4 to form a second hole transport layer 5 having a thickness of 10 nm.

(5) A light-emitting layer 6 having a thickness of 30 nm was formed by vacuum evaporation on the second hole transport layer 5, where compound D was used as the host of the light-emitting layer 6, and compound E was used as the dopant of the light-emitting layer 6, with a doping ratio being 3% by weight.

(6) Compound F was vacuum-evaporated on the light-emitting layer 6 to form a first electron transport layer 7 having a thickness of 5 nm.

(7) Compound M004 provided by the present disclosure and doping metal ytterbium (the mass ratio was 97:3) were vacuum-evaporated on the first electron transport layer 7 to form a second electron transport layer 8 having a thickness of 30 nm.

(8) Silver was vacuum-evaporated on the second electron transport layer 8 to form a cathode 9 having a thickness of 100 nm.

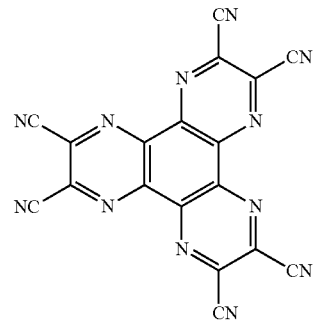

Compound A

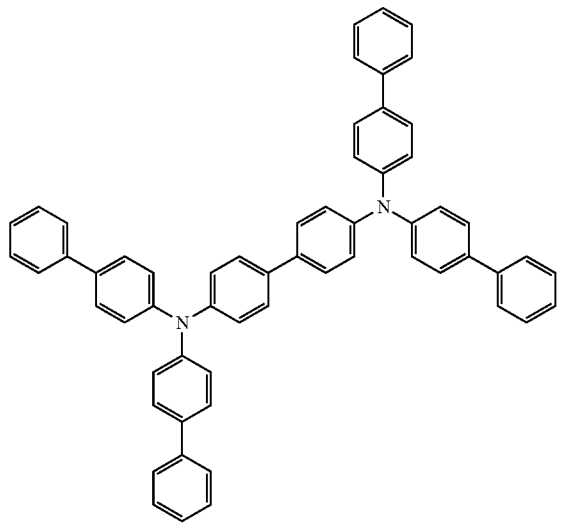

Compound B

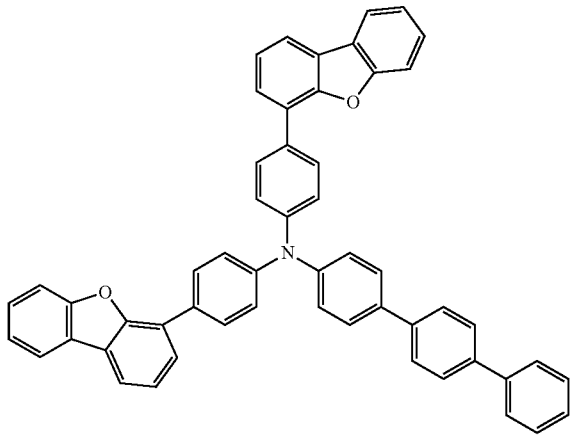

Compound C

Compound D

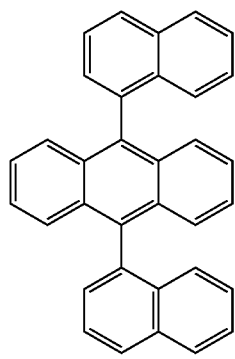

Compound E

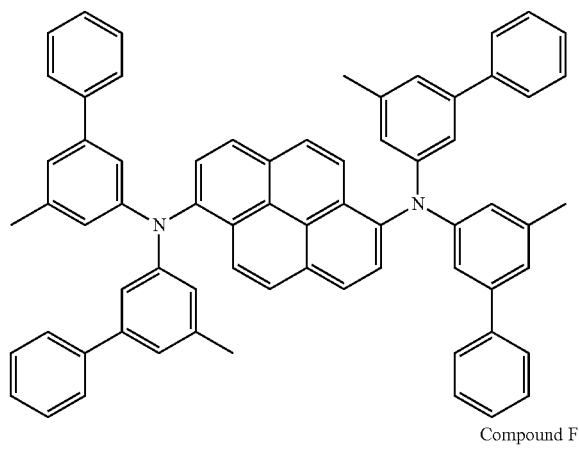

Compound F

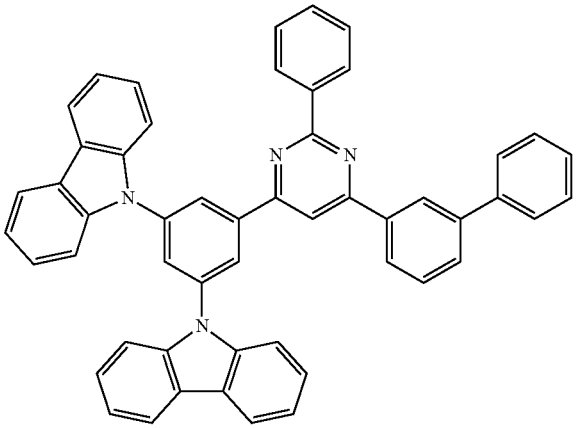

Performance Evaluation of OLED Devices:

A Keithley 2365A digital nanovoltmeter was used to measure the currents of the OLED devices at different voltages. The currents were divided by the light-emitting area to obtain current densities of the OLED device at the different voltages. Konicaminolta CS-2000 spectroradiometer was used to measure the brightness and the radiant energy flux density of the OLED devices at different voltages. According to the current densities and brightness of the OLED devices at different voltages, operating voltage (V) and a current efficiency (Cd/A) under the same current density (10 mA/cm$^2$) were obtained. Von was the turn-on voltage at a brightness of 1 cd/m$^2$. The lifetime LT95 was obtained by measuring a lasting time period before the brightness of the organic light-emitting device was reduced to 95% of an initial brightness (measured at 50 mA/cm$^2$). Test data are listed in Table 2.

Device Example 2

Device Example 2 was the same as Device Example 1 in terms of manufacturing methods for respective layers and of the materials as used, except that M004 in step (7) was replaced with M016.

Device Example 3

Device Example 3 was the same as Device Example 1 in terms of manufacturing methods for respective layers and of the materials as used, except that M004 in step (7) was replaced with M020.

Device Example 4

Device Example 4 was the same as Device Example 1 in terms of manufacturing methods for respective layers and of the materials as used, except that M004 in step (7) was replaced with M037.

Device Example 5

Device Example 5 was the same as Device Example 1 in terms of manufacturing methods for respective layers and of the materials as used, except that M004 in step (7) was replaced with M044.

Device Example 6

Device Example 6 was the same as Device Example 1 in terms of manufacturing methods for respective layers and of the materials as used, except that M004 in step (7) was replaced with M056.

Device Example 7

Device Example 7 was the same as Device Example 1 in terms of manufacturing methods for respective layers and of the materials as used, except that M004 in step (7) was replaced with M104.

Device Example 8

Device Example 8 was the same as Device Example 1 in terms of manufacturing methods for respective layers and of the materials as used, except that M004 in step (7) was replaced with M124.

Device Example 9

Device Example 9 was the same as Device Example 1 in terms of manufacturing methods for respective layers and of the materials as used, except that M004 in step (7) was replaced with M128.

Device Example 10

Device Example 10 was the same as Device Example 1 in terms of manufacturing method for respective layers and of the materials as used, except that M004 in step (7) was replaced with M136.

Device Example 11

Device Example 11 was the same as Device Example 1 in terms of manufacturing methods for respective layers and of the materials as used, except that M004 in step (7) was replaced with M140.

Device Example 12

Device Example 12 was the same as Device Example 1 in terms of manufacturing methods for respective layers and of the materials as used, except that M004 in step (7) was replaced with M144.

Device Example 13

Device Example 13 was the same as Device Example 1 in terms of manufacturing methods for respective layers and of the materials as used, except that M004 in step (7) was replaced with M157.

Device Example 14

Device Example 14 was the same as Device Example 1 in terms of manufacturing methods for respective layers and of the materials as used, except that M004 in step (7) was replaced with M201.

Device Example 15

Device Example 15 was the same as Device Example 1 in terms of manufacturing methods for respective layers and of the materials as used, except that M004 in step (7) was replaced with M202.

Device Comparative Example 1

Device Comparative Example 1 was the same as Device Example 1 in terms of manufacturing methods for respective layers and of the materials as used, except that M004 in step (7) was replaced with Comparative Compound 1.

Comparative Compound 1

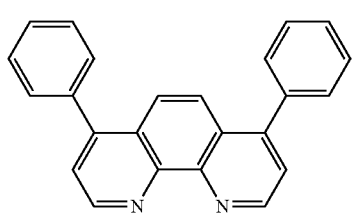

Device Comparative Example 2

Device Comparative Example 2 was the same as Device Example 1 in terms of manufacturing methods for respective layers and of the materials as used, except that M004 in step (7) was replaced with Comparative Compound 2.

Comparative Compound 2

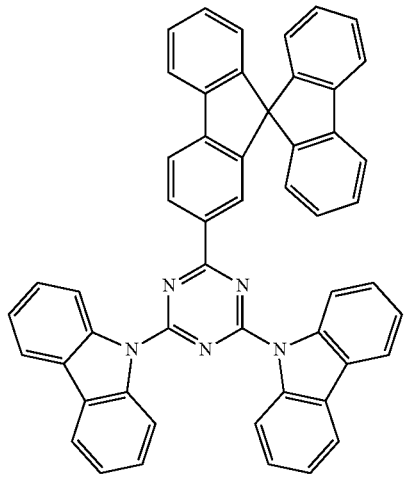

Performance Evaluation of OLED Devices

A Keithley 2365A digital nanovoltmeter was used to measure the currents of the OLED at different voltages. The currents were divided by the light-emitting area to calculate current densities of the OLED device at the different voltages. Konicaminolta CS-2000 spectroradiometer was used to measure the brightness and the radiant energy flux density of the OLED devices at different voltages. According to the current densities and brightness of the OLED devices at different voltages, a current efficiency CE (Cd/A) and operating voltage (V) of respective devices under the same current density (10 mA/cm$^2$) were obtained. Von was the turn-on voltage at a brightness of 1 cd/m$^2$. The lifetime LT95 was obtained by measuring a lasting time period before the brightness of the organic light-emitting device was reduced to 95% of an initial brightness (measured at 50 mA/cm$^2$). Test results are listed in Table 2.

TABLE 2

Test Results of Device Examples and Device Comparative Examples

| OLED device | Compounds used as electron transport material | $V_{on}$ (V) | V (V) | EC (cd/A) | Lifetime LT95 (h) |
|---|---|---|---|---|---|
| Device Example 1 | M004 | 2.67 | 3.97 | 6.70 | 70 |
| Device Example 2 | M016 | 2.67 | 3.99 | 6.82 | 72 |
| Device Example 3 | M020 | 2.68 | 3.98 | 6.75 | 74 |
| Device Example 4 | M037 | 2.74 | 4.03 | 6.34 | 65 |
| Device Example 5 | M044 | 2.66 | 3.96 | 6.68 | 69 |
| Device Example 6 | M056 | 2.68 | 4.00 | 6.85 | 72 |
| Device Example 7 | M104 | 2.72 | 4.02 | 6.39 | 62 |
| Device Example 8 | M124 | 2.65 | 3.97 | 6.78 | 72 |
| Device Example 9 | M128 | 2.69 | 4.00 | 6.65 | 66 |
| Device Example 10 | M136 | 2.66 | 3.96 | 6.80 | 73 |
| Device Example 11 | M140 | 2.67 | 3.99 | 6.72 | 70 |
| Device Example 12 | M144 | 2.75 | 4.04 | 6.36 | 65 |
| Device Example 13 | M157 | 2.73 | 4.03 | 6.30 | 68 |
| Device Example 14 | M201 | 2.70 | 3.98 | 6.58 | 69 |
| Device Example 15 | M202 | 2.69 | 3.96 | 6.64 | 68 |
| Device Comparative Example 1 | Comparative Compound 1 | 2.86 | 4.14 | 5.40 | 44 |
| Device Comparative Example 2 | Comparative Compound 2 | 2.81 | 4.15 | 5.16 | 48 |

It can be seen from the data in Table 2, compared with Comparative Compound 1 and Comparative Compound 2, the devices in Device Examples 1-12 based on the organic compounds of the present disclosure have lower turn-on voltage, lower operating voltage, higher current efficiency and longer lifetime. Without wishing to be bound by theory, it is believed that these results are due at least in part to the molecular structure having a multidentate nitrogen-containing ligand provided by the present disclosure, wherein ligand is suitable to complex with metal Yb. Therefore, metal movement caused by heat and electric field generated during the driving of the device is mitigated or otherwise reduced. In addition, in the molecules provided in the present disclosure, the triazine skeleton structure cooperates with multiple substituents having large steric hindrance, so that the organic compound has large rigid twist, and avoids or reduces the increase in intermolecular attraction resulting from the excessively planar structure of conventional triazine compounds. The organic compounds of the present disclosure have a spatial structure and an appropriate molecular weight in the range of 600-1200 g/mol suitable to control the evaporation rate and inhibit the accumulation caused by the increase of intermolecular attraction. These factors work together to lower the turn-on voltage of the OLED device, reduce the operating voltage of the OLED device, and improve the efficiency of the OLED device while prolonging the lifetime.

The compounds of the present disclosure can also be used in the charge generation layer (CGL) in laminate OLED devices. The use of the compound of the present disclosure in the charge generation layer will be described below in detail.

Device Example 16

Figure 3:
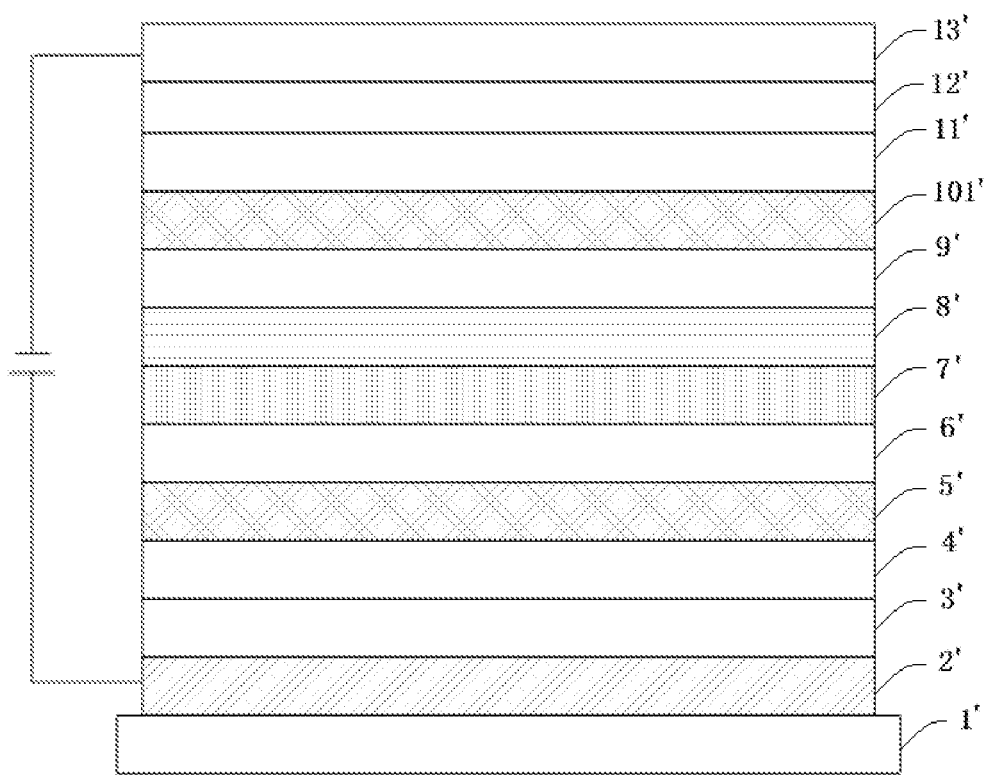
FIG. 3 is a schematic diagram of a laminate OLED device, according to an embodiment of the present disclosure.

As shown in FIG. 3, this example provides a laminate OLED device. The organic light-emitting device includes in sequence a substrate 1', an anode 2', a hole injection layer 3', a first hole transport layer 4', a first light-emitting layer 5', a first electron transport layer 6', an n-type charge generation layer 7', a p-type charge generation layer 8', a second hole transport layer 9', a second light-emitting layer 101', a second electron transport layer 11', an electron injection layer 12', and a cathode 13'.

The OLED device was manufactured by the following specific steps.

(1) A glass substrate 1' was cut into a size of 50 mm×50 mm×0.7 mm, ultrasonically treated respectively in acetone, isopropanol and deionized water for 30 min, and then cleaned in ozone for 10 min; and the obtained glass substrate with an ITO anode layer 2' was mounted on a vacuum deposition apparatus.

(2) Under a vacuum degree of 2×10$^{-6}$ Pa, compound A used as a hole injection material was vacuum-evaporated onto the ITO anode 2' to form a first hole injection layer 3' having a thickness of 5 nm.

(3) Compound B was vacuum-evaporated on the first hole injection layer 3' to form a first hole transport layer 4' having a thickness of 90 nm.

(4) A first light-emitting layer 5' having a thickness of 30 nm was vacuum-evaporated on the first hole transport layer 4', where compound D was used as the host of the first light-emitting layer 5', and compound E was used as the dopant (a blue light material) of the light-emitting layer 5', with a doping ratio being 3% by weight.

(5) Compound G was vacuum-evaporated on the first light-emitting layer 5' to form a first electron transport layer 6' having a thickness of 35 nm.

(6) The organic compound M004 of the present disclosure and metal ytterbium (mass ratio of the two was 97:3) were vacuum-evaporated on the first electron transport layer 6' to form an n-type charge generation layer 7' having a thickness of 5 nm.

(7) Compound A used as a hole injection material was vacuum-evaporated on the n-type charge generation layer 7' to form a p-type charge generation layer 8' having a thickness of 5 nm.

(8) Compound B was vacuum-evaporated on the p-type charge generation layer 8' to form a second hole transport layer 9' having a thickness of 90 nm.

(9) A second light-emitting layer 101' having a thickness of 30 nm was vacuum-evaporated on the second hole transport layer 9', where compound D was used as the host of the second light-emitting layer 101', and compound E was used as the dopant (a blue light material) of the second light-emitting layer 101', with a doping ratio being 3% by weight.

(10) Compound F was vacuum-evaporated on the second light-emitting layer 101' to form a second electron transport layer 11' having a thickness of 5 nm.

(11) Compound G and Liq (weight ratio of the two was 50:50) were vacuum-evaporated on the second electron transport layer 11' to form an electron injection layer 12' having a thickness of 35 nm.

(12) Silver was vacuum-evaporated on the electron injection layer 12' to form a cathode 13' having a thickness of 100 nm.

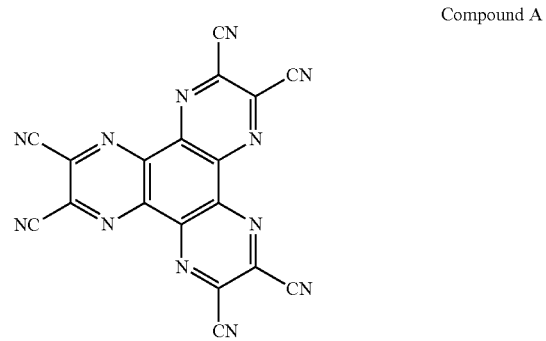

Compound A

Compound B

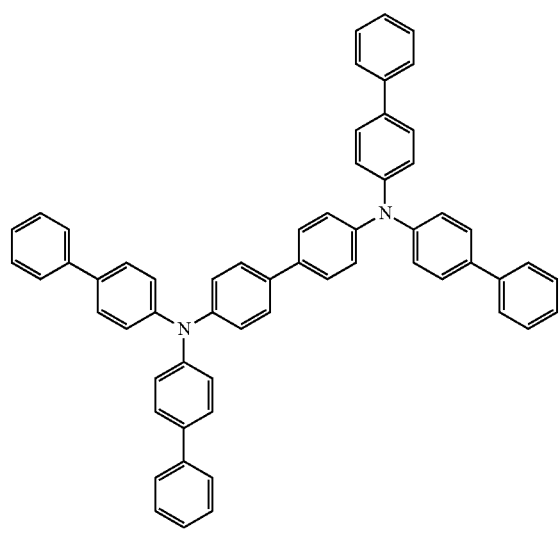

Compound C

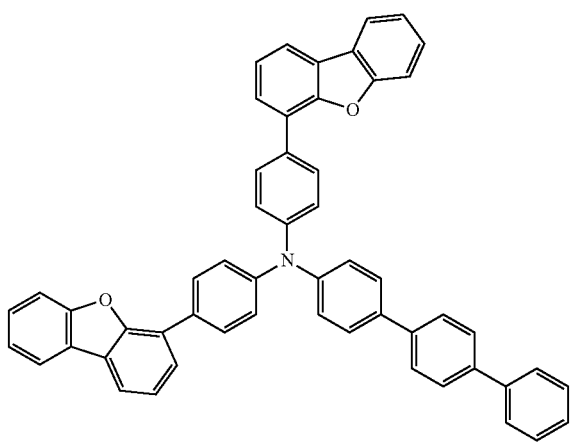

Compound D

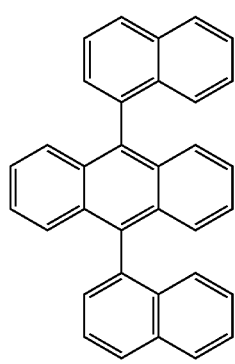

Compound E

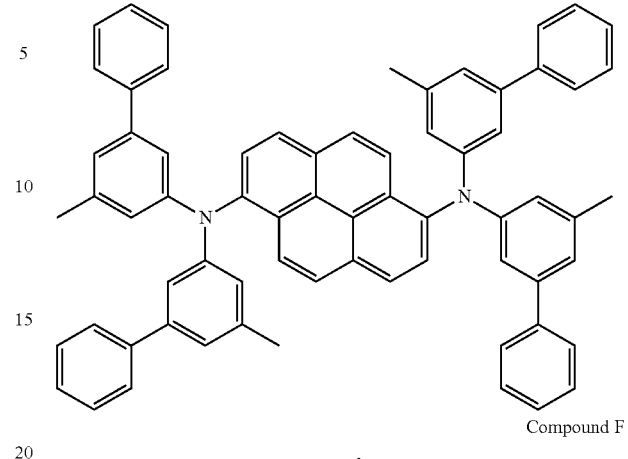

Compound F

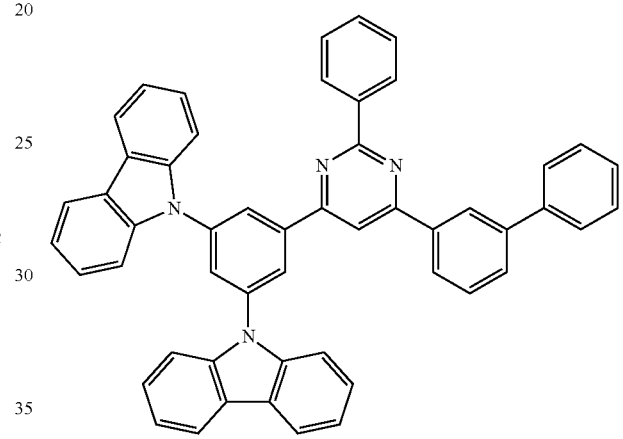

Compound G

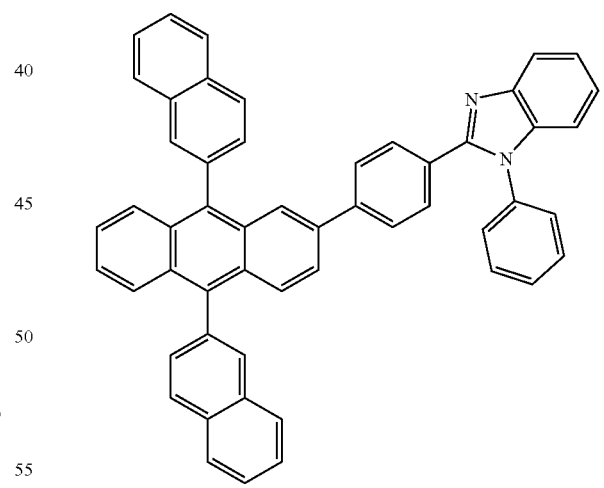

Device Example 17

Figure 4:
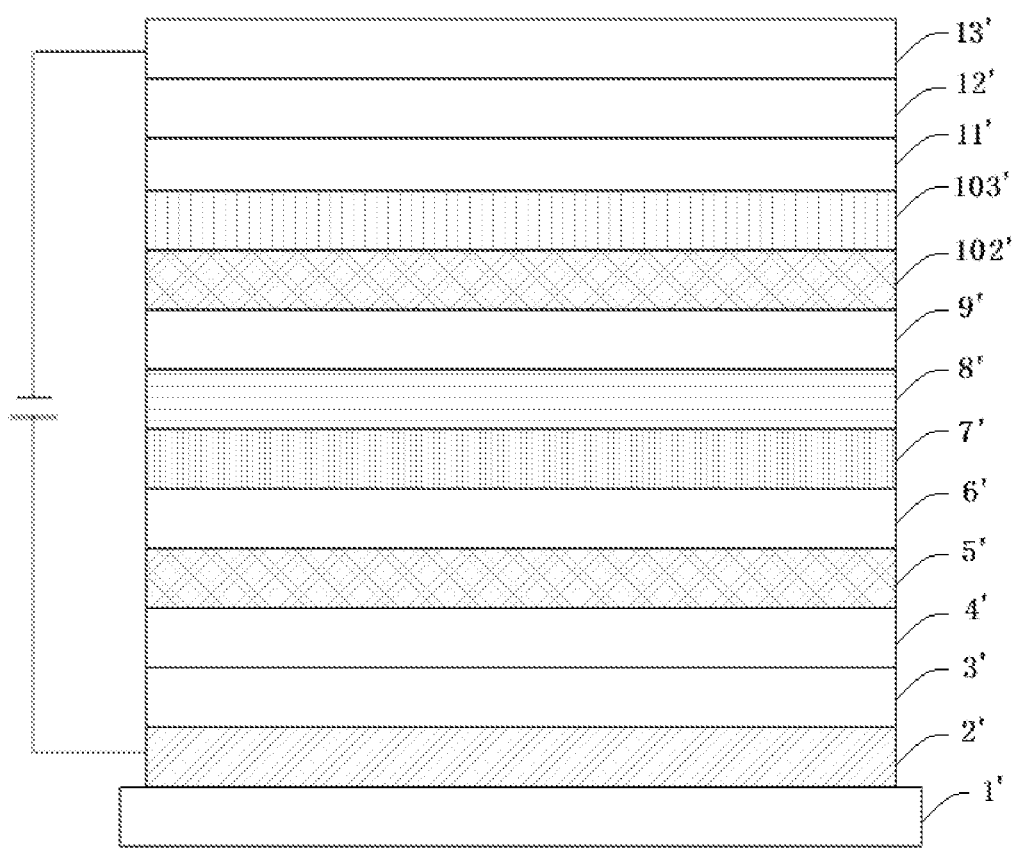
FIG. 4 is a schematic diagram of a laminate OLED device, according to another embodiment of the present disclosure.

As shown in FIG. 4, this example provides a laminate OLED device. The OLED device includes in sequence a substrate 1', an anode 2', a hole injection layer 3', a first hole transport layer 4', a first light-emitting layer 5', a first electron transport layer 6', an n-type charge generation layer 7', a p-type charge generation layer 8', a second hole transport layer 9', a second light-emitting layer 102', a third light-emitting layer 103', a second electron transport layer 11', an electron injection layer 12', and a cathode 13'.

The OLED device was manufactured by the following specific steps.

(1) A glass substrate 1' was cut into a size of 50 mm×50 mm×0.7 mm, ultrasonically treated respectively in acetone, isopropanol and deionized water for 30 min, and then cleaned in ozone for 10 min; and the obtained glass substrate with an ITO anode layer 2' was mounted on a vacuum deposition apparatus.

(2) Under a vacuum degree of $2\times10^{-6}$ Pa, a hole injection material of compound A was vacuum-evaporated onto the ITO anode 2' to form a first hole injection layer 3' having a thickness of 5 nm.

(3) Compound B was vacuum-evaporated on the first hole injection layer 3' to form a first hole transport layer 4' having a thickness of 90 nm.

(4) A first light-emitting layer 5' having a thickness of 30 nm was vacuum-evaporated on the first hole transport layer 4', where compound D was used as the host of the first light-emitting layer 5', and compound E was used as the dopant (a blue light material) of the light-emitting layer 5', with a doping ratio being 3% by weight.

(5) Compound G was vacuum-evaporated on the first light-emitting layer 5' to form a first electron transport layer 6' having a thickness of 35 nm.

(6) The organic compound M004 of the present disclosure and metal ytterbium (mass ratio of the two was 97:3) were vacuum-evaporated on the first electron transport layer 6' to form an n-type charge generation layer 7' having a thickness of 5 nm.

(7) Compound A used as a hole injection material was vacuum-evaporated on the n-type charge generation layer 7' to form a p-type charge generation layer 8' having a thickness of 5 nm.

(8) Compound B was vacuum-evaporated on the p-type charge generation layer 8' to form a second hole transport layer 9' having a thickness of 90 nm.

(9) A second light-emitting layer 102' having a thickness of 30 nm was formed by vacuum-evaporation on the second hole transport layer 9', where compound H was used as the host of the second light-emitting layer 102', and compound I was used as the dopant (a green light material) of the second light-emitting layer 102', with a doping ratio being 8% by weight; a third light-emitting layer 103' having a thickness of 30 nm was formed by vacuum-evaporation on the second light-emitting layer 102', where compound H was used as the host of the third light-emitting layer 103', and compound J was used as the dopant (a red light material) of the third light-emitting layer 103', with a doping ratio being 8% by weight;

(10) Compound F was vacuum-evaporated on the third light-emitting layer 103' to form a second electron transport layer 11' having a thickness of 5 nm.

(11) Compound G and Liq (weight ratio of the two was 50:50) were vacuum-evaporated on the second electron transport layer 11' to form an electron injection layer 12' having a thickness of 35 nm.

(12) Silver was vacuum-evaporated on the electron injection layer 12' to form a cathode 13' having a thickness of 100 nm.

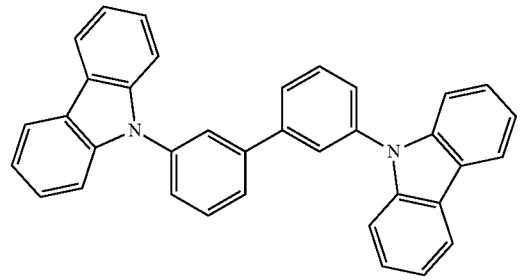

Compound H

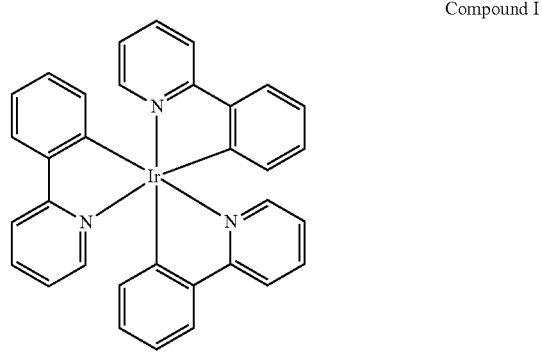

Compound I

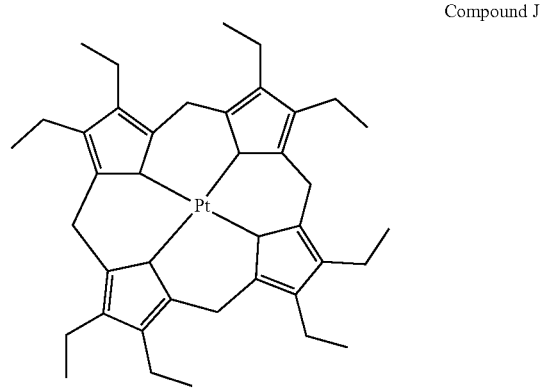

Compound J

Table 3 shows the test results for the light-emitting performance of the devices in Device Example 16 and Device Example 17.

TABLE 3

| OLED device | Compound used in CGL | V (V) | Current efficiency (cd/A) |
| --- | --- | --- | --- |
| Device Example 16 | M004 | 7.4 | 11.2 |
| Device Example 17 | M004 | 8.2 | 60.3 |

It can be seen from Table 3 that the compounds of the present disclosure can be doped with metal Yb to form an n-type charge generation layer. In Device Example 16, two blue light-emitting layers are arranged in series to provide a blue light-emitting device having a current efficiency of up to 11.2 cd/A. In Device Example 17, a blue light-emitting layer, a red light-emitting layer and a green light-emitting layer are arranged in series to provide a white light-emitting device having a current efficiency of up to 60.3 cd/A, indicating that the compounds of the present disclosure are excellent n-type CGL material suitable for the CGL material in laminate OLED devices.

Another aspect of the present disclosure further provides a display apparatus which includes the display panel as described above.

Figure 5:
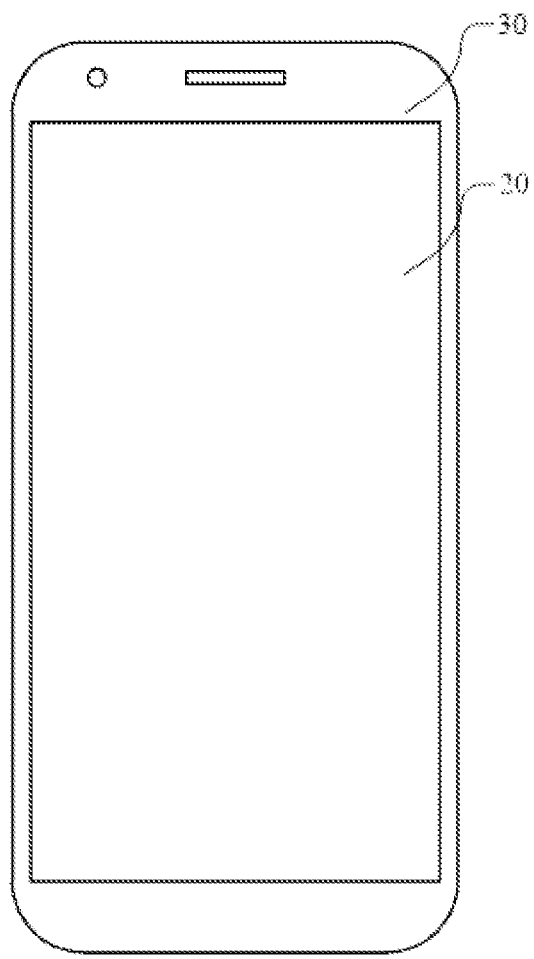
FIG. 5 is a schematic diagram of a display apparatus, according to an embodiment of the present disclosure.

In the present disclosure, the display apparatus can be a display screen of a mobile phone, a computer, a TV, a smart watch, a smart car, a VR or AR helmet, or any other smart devices. FIG. 5 is a schematic diagram of a display apparatus according to an embodiment of the present disclosure, e.g., a smartphone 30. In FIG. 5, the display apparatus includes the display panel 20 of the embodiment of the present disclosure.

Although the present disclosure is disclosed as above in preferred embodiments, it is not intended to limit the scopes of the claims. Any person skilled in the art can make several possible changes and modifications without departing from the concept of the present disclosure. Therefore, the scope of protection of the present disclosure should be defined by the claims of this application.

What is claimed is:

1. A compound having a structure according to general formula 1:

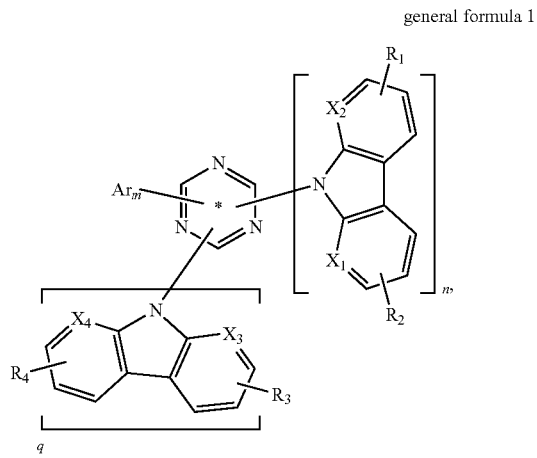

general formula 1 wherein $X_1$-$X_4$ are each independently selected from the group consisting of a carbon atom and a nitrogen atom, and at least two of $X_1$-$X_4$ are each a nitrogen atom;

$R_1$-$R_4$ are each independently absent or selected from the group consisting of a hydrogen atom, a C1-C20 alkyl group, a C1-C20 alkoxy group, a C1-C20 alkylthio group, a C1-C20 alkylamino group, a C6-C30 aryl group, and a C2-C30 heteroaryl group;

Ar is selected from the following group:

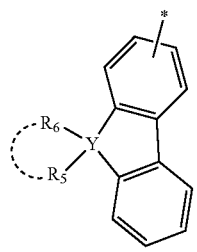

wherein $R_5$ and $R_6$ are each independently absent or selected from the group consisting of a hydrogen atom, a C1-C20 alkyl group, a C1-C20 alkoxy group, a C1-C20 alkylthio group, a C1-C20 alkylamino group, a C6-C30 aryl group, and a C2-C30 heteroaryl group;

$R_5$ and $R_6$ are capable of forming a ring;

Y is selected from the group consisting of a phosphorus atom, a P—O group, a silicon atom, and a germanium atom; and

* indicates a possible bonding position;

m is an integer selected from 1 or 2; and n and q are each integers independently selected from 0, 1 or 2, n+q≥1, and m+n+q=3.

2. The compound according to claim 1, wherein two, three or four of $X_1$-$X_4$ are each a nitrogen atom.

3. The compound according to claim 1, wherein m is 1, n is 1, and q is 1.

4. The compound according to claim 1, wherein m is 2, n is 1, and q is 0.

5. The compound according to claim 1, wherein Ar is selected from the following groups:

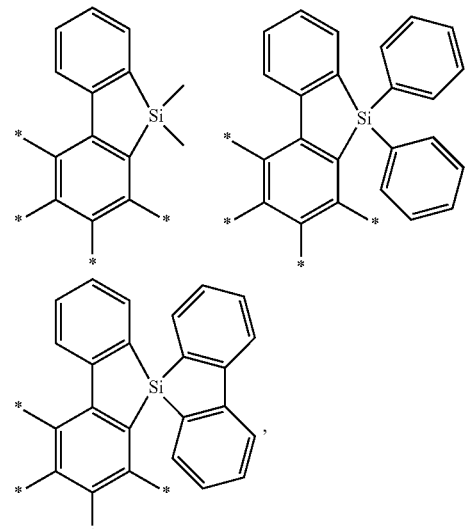

wherein * indicates a possible bonding position.

6. The compound according to claim 1, wherein Ar is selected from the following group:

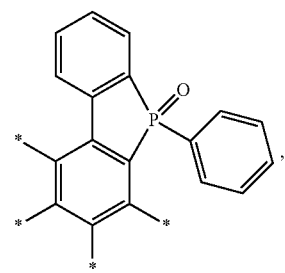 [SMILES: *c1c(*)c(*)c2c(c1*)-c1ccccc1P2(=O)c1ccccc1]

wherein * indicates a possible bonding position.

7. A compound being any one of the following compounds:
M024
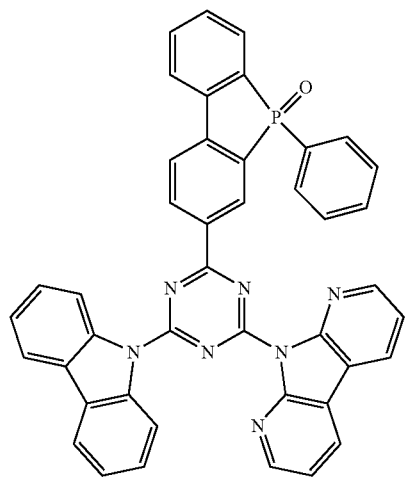
M025
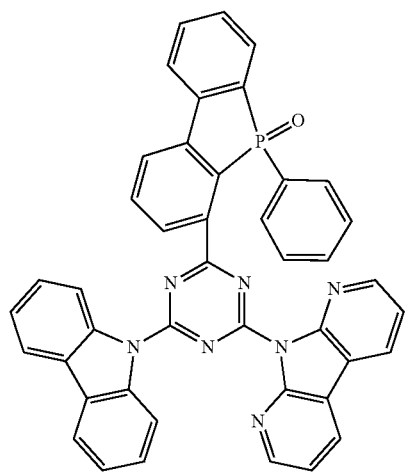
M026
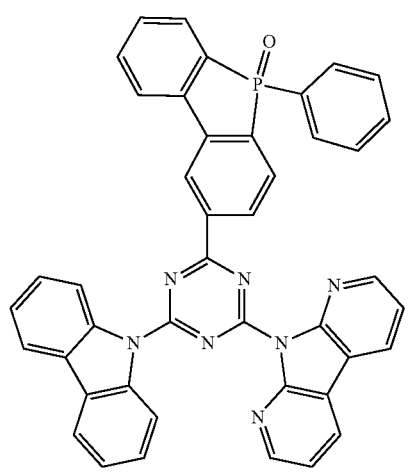
-continued
M027
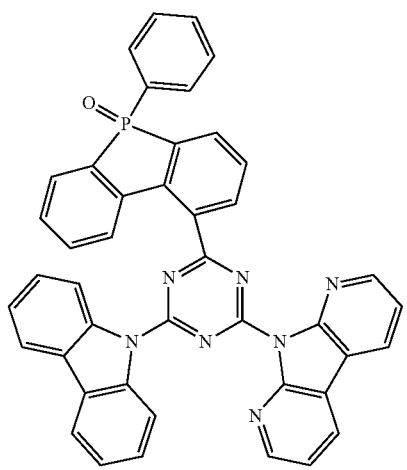
M064
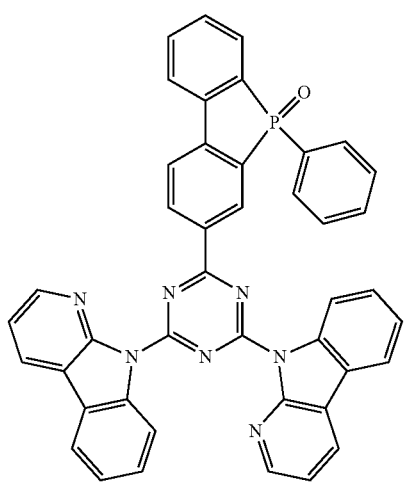
M065
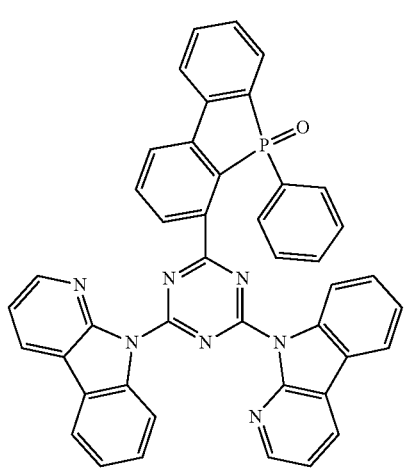

M066
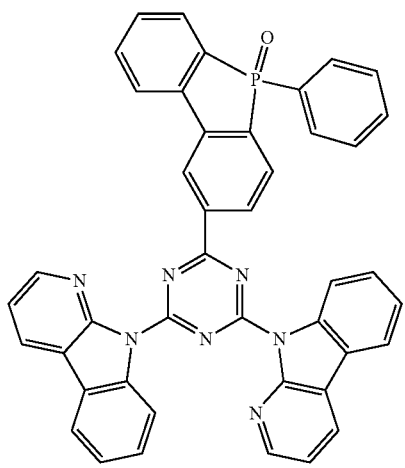
M067
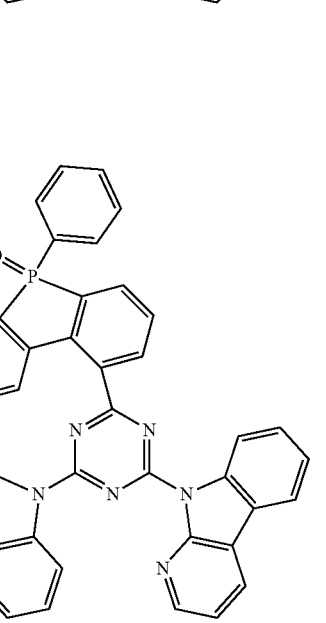
M104
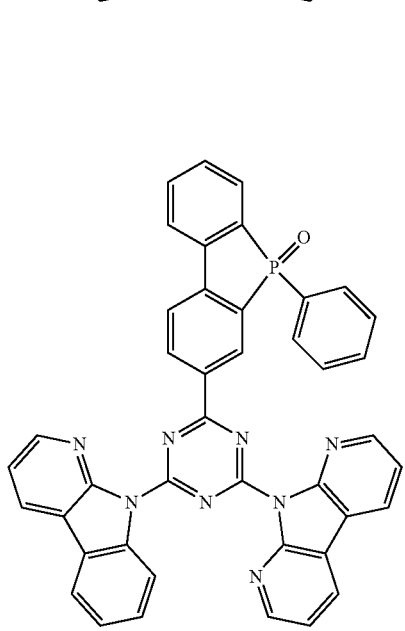
M105
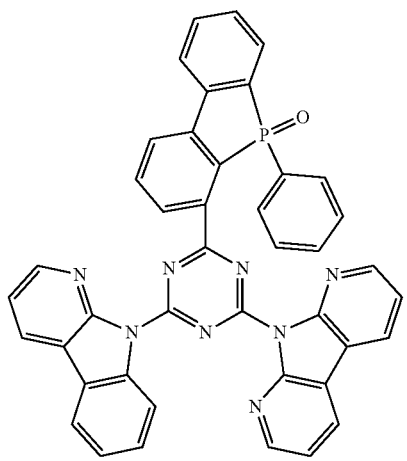
M106
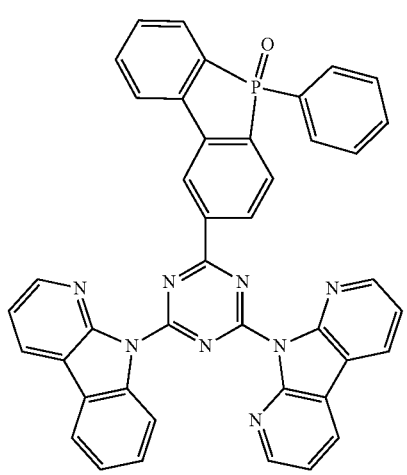
M107
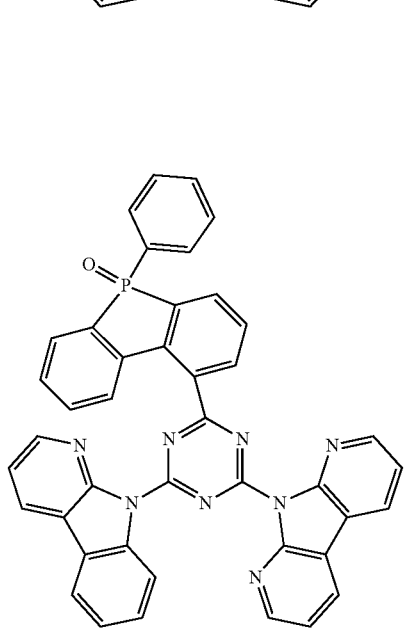

M144
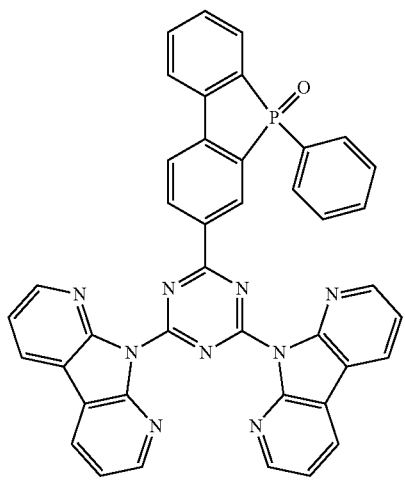
M145
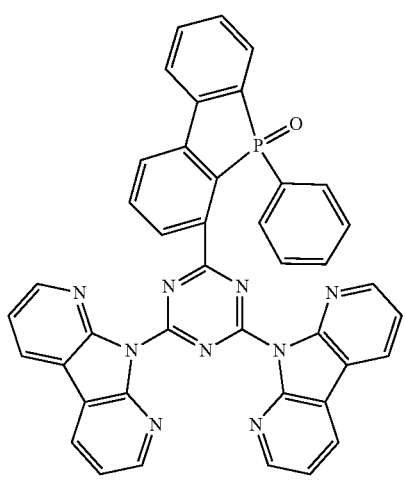
M146
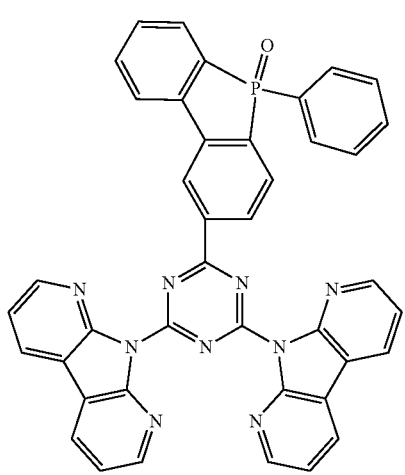
M147
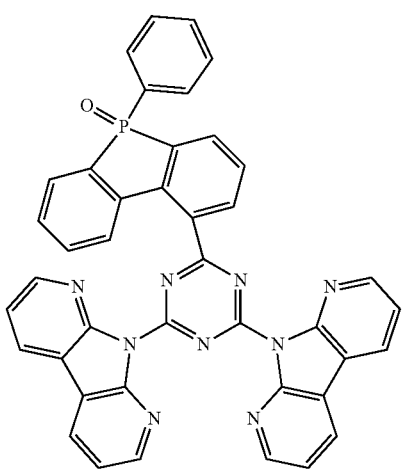
M184
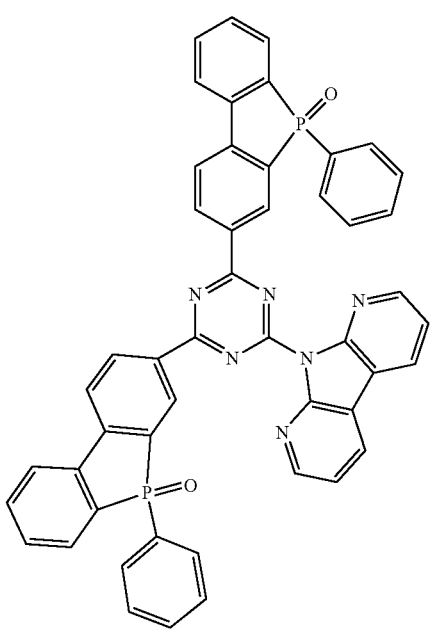
M185
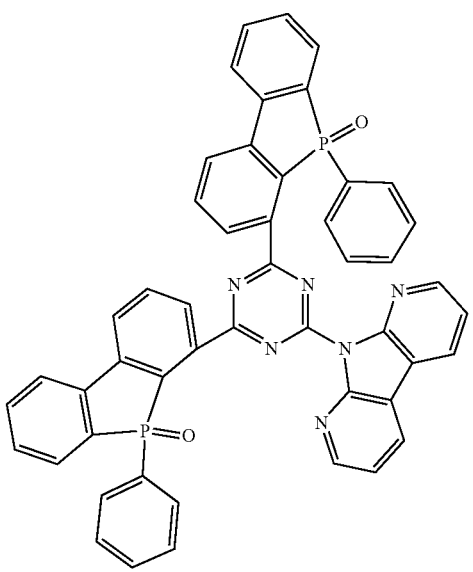

M186
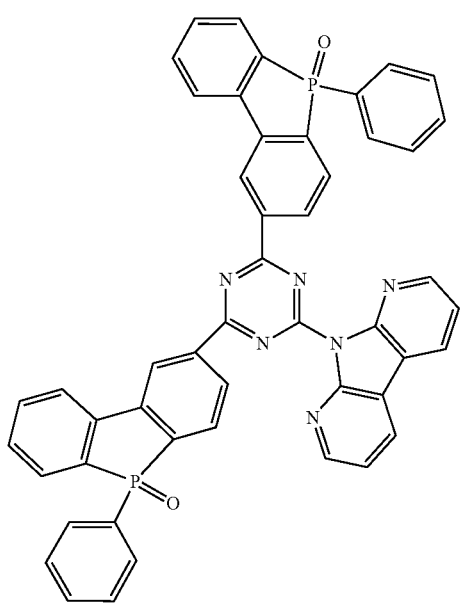
M187
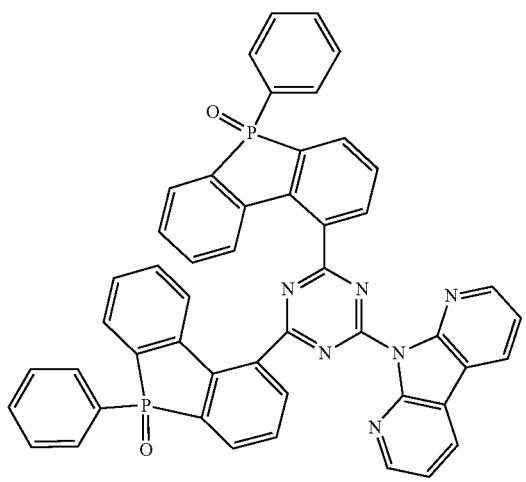
ET030M201
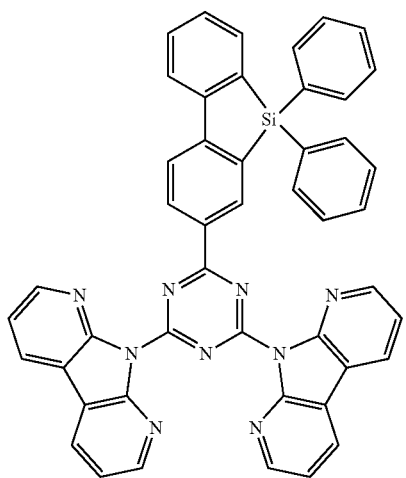
ET031M202
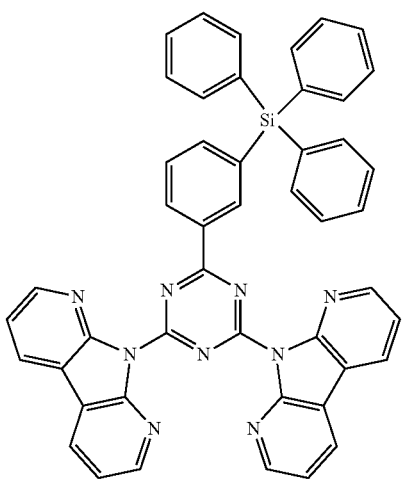
M203
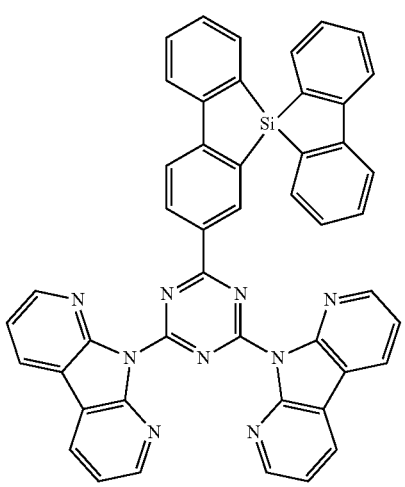
M204
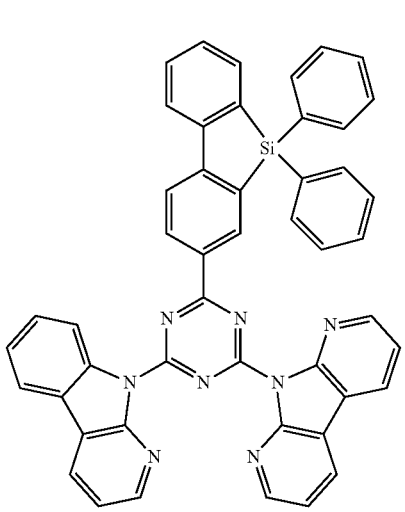

M205
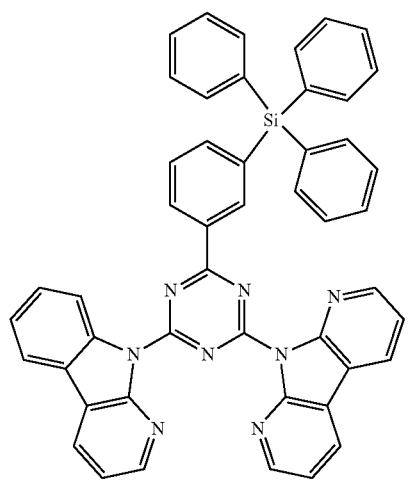
M208
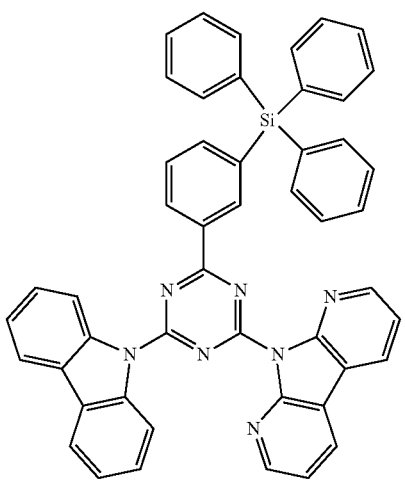
M206
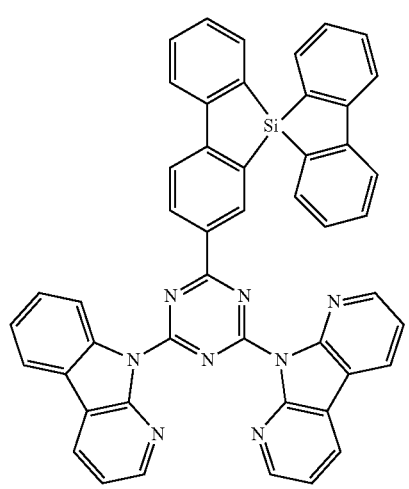
M209
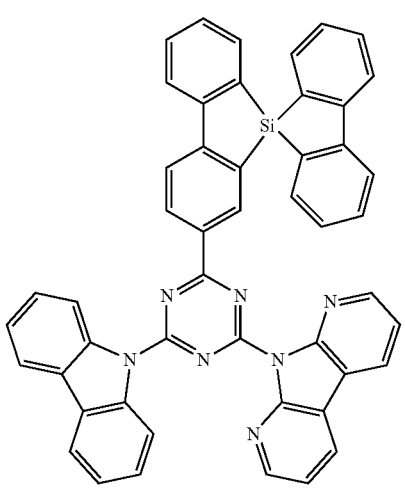
M207
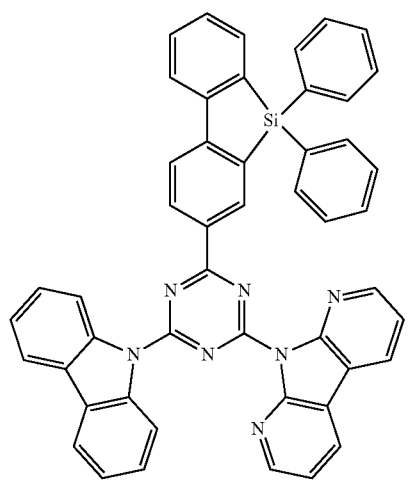
M210
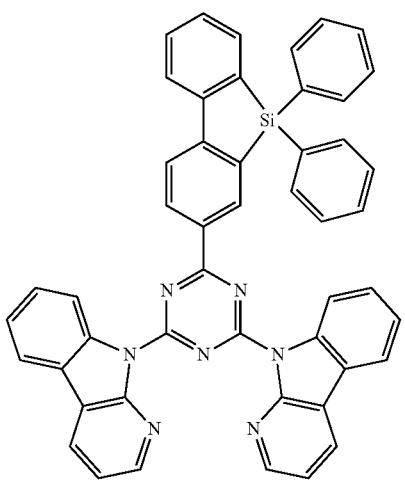

-continued

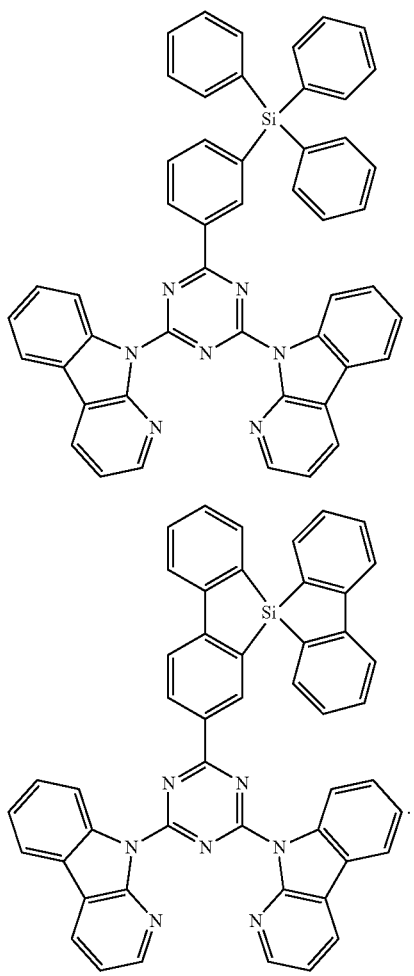

M211

M212

8. A display panel, comprising: an organic light-emitting device, wherein the organic light-emitting device comprises:
an anode;
a cathode disposed oppositely to the anode; and
an electron transport layer and a light-emitting layer that are disposed between the anode and the cathode,
wherein the electron transport layer comprises the compound according to claim 1 and a dopant, wherein the dopant is selected from the group consisting of metal lithium, a lithium organic complex, and metal Yb.

9. The display panel according to claim 8, wherein
the lithium organic complex is lithium 8-quinolinolate, and when lithium 8-quinolinolate is doped as the dopant, lithium 8-quinolinolate is doped in mass ratio of 30%-70%, based on a total mass of the electron transport layer;
when metal lithium is doped as the dopant, lithium is doped in mass ratio of 1.4%-3.4%, based on a total mass of the electron transport layer; and
when the metal Yb is doped as the dopant, the metal Yb is doped in a mass ratio of 0.1%-10%, based on a total mass of the electron transport layer.

10. The display panel according to claim 8, wherein the organic light-emitting device further comprises a hole blocking layer, wherein the hole blocking layer comprises a compound according to claim 1.

11. A display panel, comprising an organic light-emitting device, wherein the organic light-emitting device comprises:
an anode;
a cathode;
a first lamination layer and a second lamination layer disposed between the anode and the cathode and spaced apart from each other; and
a charge generation layer between the first lamination layer and the second lamination layer and comprising a compound according to claim 1 and a dopant, wherein the dopant is selected from lithium, a lithium organic complex, or metal Yb,
wherein each of the first lamination layer and the second lamination layer comprises a light-emitting layer, wherein the light-emitting layer of the first lamination layer comprises a first light-emitting layer formed between the anode and the charge generation layer, and the light-emitting layer of the second lamination layer comprises a second light-emitting layer formed between the cathode and the charge generation layer.

12. The display panel according to claim 11, wherein
the lithium organic complex is lithium 8-quinolinolate, and when lithium 8-quinolinolate is doped as the dopant, lithium 8-quinolinolate is doped in mass ratio of 30%-70%, based on a total mass of the charge generation layer;
when lithium is doped as the dopant, lithium is doped in mass ratio of 1.4%-3.4%, based on a total mass of the charge generation layer; and
when the metal Yb is doped as the dopant, the metal Yb is doped in a mass ratio of 0.1%-10%, based on a total mass of the charge generation layer.

13. The display panel according to claim 11, wherein the first light-emitting layer and the second light-emitting layer are each independently selected from a mono-color light-emitting layer, or a composite light-emitting layer formed by stacking a plurality of mono-color light-emitting layers,
wherein the mono-color light-emitting layer is selected from a red light-emitting layer, a green light-emitting layer, a blue light-emitting layer, or a yellow light-emitting layer, and
wherein each mono-color light-emitting layer of the plurality of mono-color light-emitting layers is independently selected from a red light-emitting layer, a green light-emitting layer, a blue light-emitting layer, or a yellow light-emitting layer.

14. The display panel according to claim 11, wherein the first light-emitting layer and the second light-emitting layer are each independently selected from a fluorescent light-emitting layer or a phosphorescent light-emitting layer.

15. A display apparatus, comprising the display panel according to claim 8.

* * * * *